(12) United States Patent
Yatcilla et al.

(10) Patent No.: US 10,322,156 B2
(45) Date of Patent: Jun. 18, 2019

(54) METHODS OF TREATMENT USING PURIFIED (DECOLORIZED) ALOE VERA LEAF DRY JUICE

(71) Applicant: Herbalife International, Inc., Los Angeles, CA (US)

(72) Inventors: Michael Yatcilla, Los Angeles, CA (US); Wenjie Li, Mission Viejo, CA (US); Andrea Bertocco, Stanmore (GB); Joosang Park, Irvine, CA (US)

(73) Assignee: HERBALIFE INTERNATIONAL OF AMERICA, INC., Los Angeles, CA (US)

( * ) Notice: Subject to any disclaimer, the term of this patent is extended or adjusted under 35 U.S.C. 154(b) by 0 days.

(21) Appl. No.: 15/623,246

(22) Filed: Jun. 14, 2017

(65) Prior Publication Data

US 2018/0008661 A1  Jan. 11, 2018

Related U.S. Application Data

(60) Provisional application No. 62/488,497, filed on Apr. 21, 2017, provisional application No. 62/359,621, filed on Jul. 7, 2016.

(51) Int. Cl.

| | |
|---|---|
| *A61K 36/886* | (2006.01) |
| *A23L 2/02* | (2006.01) |
| *A23L 2/08* | (2006.01) |
| *A23L 2/39* | (2006.01) |
| *A23L 2/70* | (2006.01) |
| *A23L 2/72* | (2006.01) |
| *A23L 2/80* | (2006.01) |
| *A23L 29/20* | (2016.01) |
| *A23L 29/206* | (2016.01) |
| *A23L 29/212* | (2016.01) |
| *A23L 29/238* | (2016.01) |
| *A23L 29/25* | (2016.01) |
| *A23L 29/262* | (2016.01) |
| *A23L 29/275* | (2016.01) |
| *A23L 29/294* | (2016.01) |
| *A23L 19/00* | (2016.01) |
| *A23L 33/105* | (2016.01) |
| *A61K 31/7028* | (2006.01) |
| *A61K 31/736* | (2006.01) |
| *A23L 2/52* | (2006.01) |
| *A23L 2/56* | (2006.01) |
| *A23L 2/58* | (2006.01) |
| *A23L 2/68* | (2006.01) |

(52) U.S. Cl.
CPC ............ *A61K 36/886* (2013.01); *A23L 2/02* (2013.01); *A23L 2/08* (2013.01); *A23L 2/39* (2013.01); *A23L 2/70* (2013.01); *A23L 2/72* (2013.01); *A23L 2/80* (2013.01); *A23L 19/01* (2016.08); *A23L 29/20* (2016.08); *A23L 29/206* (2016.08); *A23L 29/212* (2016.08); *A23L 29/238* (2016.08); *A23L 29/25* (2016.08); *A23L 29/262* (2016.08); *A23L 29/275* (2016.08); *A23L 29/294* (2016.08); *A23L 33/105* (2016.08); *A61K 31/7028* (2013.01); *A61K 31/736* (2013.01); *A23L 2/52* (2013.01); *A23L 2/56* (2013.01); *A23L 2/58* (2013.01); *A23L 2/68* (2013.01); *A23V 2002/00* (2013.01); *A61K 2236/10* (2013.01)

(58) Field of Classification Search
None
See application file for complete search history.

(56) References Cited

U.S. PATENT DOCUMENTS

| | | | | |
|---|---|---|---|---|
| 4,966,892 | A | * | 10/1990 | McAnalley .......... A61K 31/715 424/744 |
| 2007/0286914 | A1 | | 12/2007 | Pasco et al. |
| 2010/0255130 | A1 | * | 10/2010 | DeBaun ............... A61K 36/886 424/744 |
| 2013/0337116 | A1 | | 12/2013 | Petralia |
| 2017/0014461 | A1 | * | 1/2017 | Jia ....................... A61K 36/282 |

FOREIGN PATENT DOCUMENTS

CN          102106502       * 10/2013

OTHER PUBLICATIONS

Gullon, B. et al. In vitro Assessment of the Prebiotic Potential of Ale vera Mucilage and its Impact on the Human Microbiota. Food & Function 6(2)525-531, 2015. (Year: 2015).*
Karaca K. et al. Nitric Oxide Production by Chicken Macrophages Activated by Acemannan . . . Int J Immunopharmacology 17(3)183-188, 1995. (Year: 1995).*
Vanisree M. et al. Modulation of Activated Murine Peritoneal Macrophages Functions by Emodin, Ale Emodin and Barbaloin . . . J of Food and Drug Analysis 14(1)7-11, 2006. (Year: 2006).*
Baruah A. et al. Aloe vera: A Multipurpose Industrial Crop. Industrial Crops and Products 94:951-963, Dec. 30, 2016. (Year: 2016).*
Leung, M. et al. Chemical and Biological Characterization of a Polysaccharide Biological Response Modifier from Aloe vera. Glycobiology 14(6)501-510, Jun. 2004. (Year: 2004).*
Tomasin R. et al. Oral Administration of Aloe vera and Honey Improves the Host Body Composition . . . J of Medicinal Food 18(10) 1128-1135, Oct. 2015. (Year: 2015).*
Pogribna M. et al. Effect of Aloe vera Whole Leaf Extract on Short Chain Fatty Acids Production . . . Letters in Applied Microbiology 46(5)575-580, May 2008. (Year: 2008).*
Yun, N. et al. Protective Effect of Aloe vera on Polymicrobial Sepsis in Mice. Food and Chemical Toxicology 47(6)1341-1348, 2009. (Year: 2009).*

(Continued)

*Primary Examiner* — Ralph J Gitomer
(74) *Attorney, Agent, or Firm* — Knobbe, Martens, Olson & Bear, LLP

(57) ABSTRACT

Disclosed herein is a method for improving the health of animal or human microflora using *aloe vera*. The method may induce the beneficial effect of activation of natural killer T cells. A method of purifying decolorized dried *aloe vera* leaf juice is also disclosed.

19 Claims, 60 Drawing Sheets

(56) References Cited

OTHER PUBLICATIONS

Paul S. et al. Curative and Protective Properties of Crude Gel of Aloe vera . . . Indian J of Traditional Knowledge 16(1)121-127, Jan. 2017. (Year: 2017).*
Anonymous: "Flavored Aloe Juices—Lily of the Desert" retrieved from the internet on Aug. 17, 2017: URL:http://web.archive.org/web/20160519145332/http://www.lilyofthedesert .com:80/product/flavored-aloe-vera-juices/ , May 19, 2016.
Anonymous : "Lily of the Desert—Aloe Mix n' Go" retrieved from the Internet on Aug. 17, 2017: URL:http://web.archive.org/web/20160605194 239/http://www.lilyofthedesert.com:80/product /aloe-mix-n-go/ , Jun. 5, 2016.
Anonymous: "Lily of the Desert—Proven Science, Proven Safe" retrieved from the Internet on Aug. 17, 2017: URL:http://web.archive.org/web/20160407120201/http://www.lilyofthedesert.com:80/about-lily/clinical-studies/proven-science-proven-safe/ , Apr. 7. 2016.
Anonymous : "Lily of the Desert—Digestive Health" retrieved from the Internet on Aug. 17, 2017: URL:http://web.archive.org/web/20160516202016/http://www.lilyofthedesert.com/about-lily/clinical-studies/digestive-health/ , May 16, 2016.
Anonymous: "Lily of the Desert Whole Leaf and Fillet Aloe Vera Juice Significantly Enhances Immune Function, Increases Antioxidant Ability and Decreases Toxins in Healthy Subjects" retrieved from the Internet Aug. 18, 2017: URL:http://web.archive.org/web/20150915065023if_/http://www.lilyofthedesert.com/wp-content/uploads/2012/09/Abstract.pdf , Sep. 15, 2015.
Anonymous: "Natural killer cell—Wikipedia", retrieved from the Internet Aug. 18, 2017: URL:https://en.wikipedia.org/w/index.php?title=Natural_killer_cell&oldid=723325334 , Jun. 2, 2016.
Pogribna, M., et al. "Effect of Aloe vera whole leaf extract on short chain fatty acids production by *Bacteroides fragilis, Bifidobacterium infantis* and *Eubacterium limosum*." Letters in applied microbiology vol. 46, No. 5 (Mar. 19, 2008): 575-580.
Tully, Lisa: "Peer Review of Clinical Research on Lily of the Desert Aloe Vera Demonstrati ng Inmune Enhancement, Increased Antioxidant Ability and Decrease in Toxins in Humans Conducted by Fenestra Research" retrieved from the Internet Aug. 18, 2017: URL:http://web.archive.org/web/20130606140619if /http://www.Lilyofthedesert.com , Jun. 9, 2008.
PCT Search Report and Written Opinion dated Aug. 31, 2017 in corresponding international application PCT/US2017/037779 filed Jun. 15, 2017.
Written Opinion of the International Preliminary Examining Authority dated Jun. 12, 2018 in Application No. PCT/US2017/037779, filed Jun. 15, 2017, which is related to the present application.
Marzorati et al., "Barcoded pyrosequencing analysis of the microbial community in a simulator of the human gastrointestinal tract showed a colon region-specific microbiota modulation for two plant-derived polysaccharide blends", Antonie van Leeuwenhoek, 2013, vol. 103, pp. 409-420.
Marzorati et al., "In vitro modulation of the human gastrointestinal microbial community by plant-derived polysaccharide-rich dietary supplements", International Journal of Food Microbiology, 2010, vol. 139, pp. 168-176.
Gullon et al., "In vitro assessment of the prebiotic potential of Aloe vera mucilage and its impact on the human microbiota", Food & Function, 2015, vol. 6, pp. 525-531.
Rodriguez et al., "Aloe vera as a Functional Ingredient in Foods", Critical Reviews in Food Science and Nutrition, 2010, vol. 50, pp. 305-326.
International Preliminary Report on Patentability dated Sep. 7, 2018 in Application No. PCT/US2017/037779, filed Jun. 15, 2017, which is related to the present application.

* cited by examiner

| Treatment | Permeability | | Immune markers | | | | | |
|---|---|---|---|---|---|---|---|---|
| | TEER | LY | IL-10 | IL-6 | IL-8 | TNF-a | NF-kB | |
| NaB | G | Y | G | G | G/Y | G/Y | G | PART I: fold-increase or decrease from control (gM or LPS - 1.0) |
| HC | | | R | R | Y/R | Y/R | Y/R | |
| gM | Y | Y | R | R | R | R | R | |
| LPS | | | Y | Y | Y | Y | Y | |
| Aloe 1 | G | Y | Y | Y/R | Y | Y/R | Y | |
| Aloe 2 | G | Y/R | Y/G | Y/R | Y | Y/R | Y | |
| Epicor | G | Y | Y | Y | Y | G | Y/R | |
| Aloe 1_PC_C | Y | Y | Y | Y | Y | Y | Y | PART II: fold-increase or decrease from respective control period (-1.0) |
| Aloe 1_PC_T | R | G | Y | Y | Y | Y/G | Y/G | |
| Aloe 1_DC_C | Y | Y | Y | Y | Y | Y | Y | |
| Aloe 1_DC_T | Y/R | Y/G | Y | Y | G | G | Y/R | |
| Aloe 2_PC_C | Y | Y | Y | Y | Y | Y | Y | |
| Aloe 2_PC_T | Y/G | G | Y/R | Y/R | G | G | Y/R | |
| Aloe 2_DC_C | Y | Y | Y | Y | Y | Y | Y | |
| Aloe 2_DC_T | G | Y | Y | Y | Y | Y/R | Y | |
| EpiCor_PC_C | Y | Y | Y | Y | Y | Y | Y | |
| EpiCor_PC_T | Y/G | Y/G | Y | Y | Y | R | Y | |
| EpiCor_DC_C | Y | Y | Y | Y | Y | Y | Y | |
| EpiCor_DC_T | Y | R | Y/R | Y/G | Y | Y/R | Y/G | |

FIG. 21

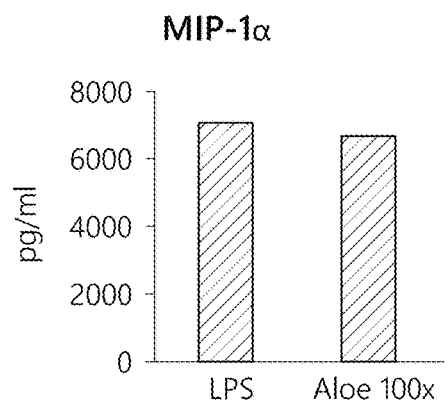
FIG. 33A (I)
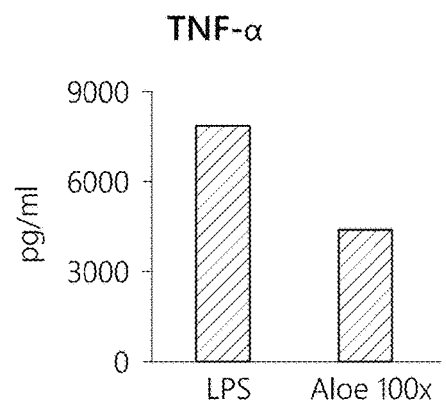
FIG. 33A (II)
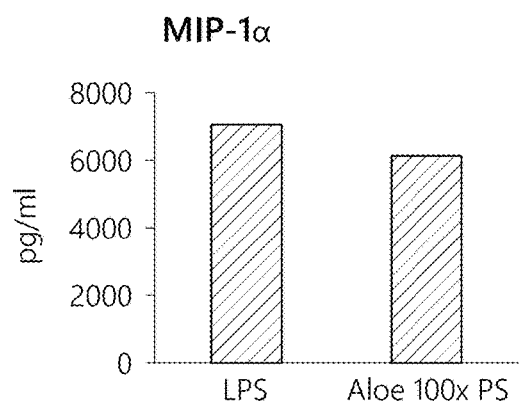
FIG. 33A (III)
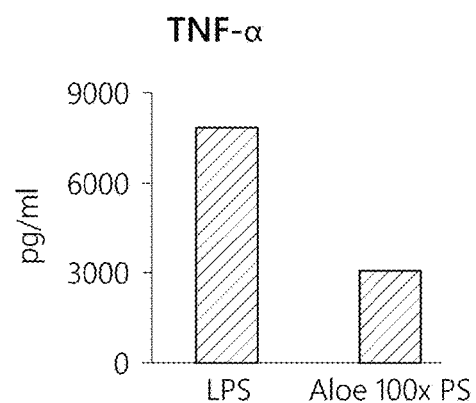
FIG. 33A (IV)

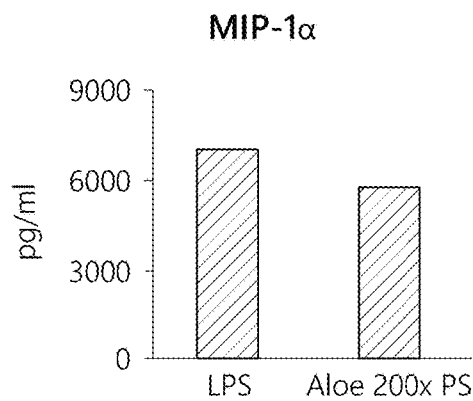
FIG. 33B (I)
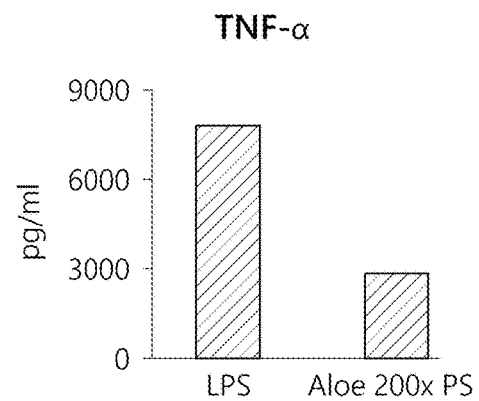
FIG. 33B (II)
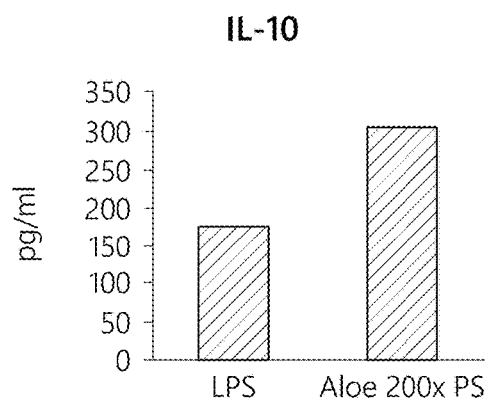
FIG. 33B (III)

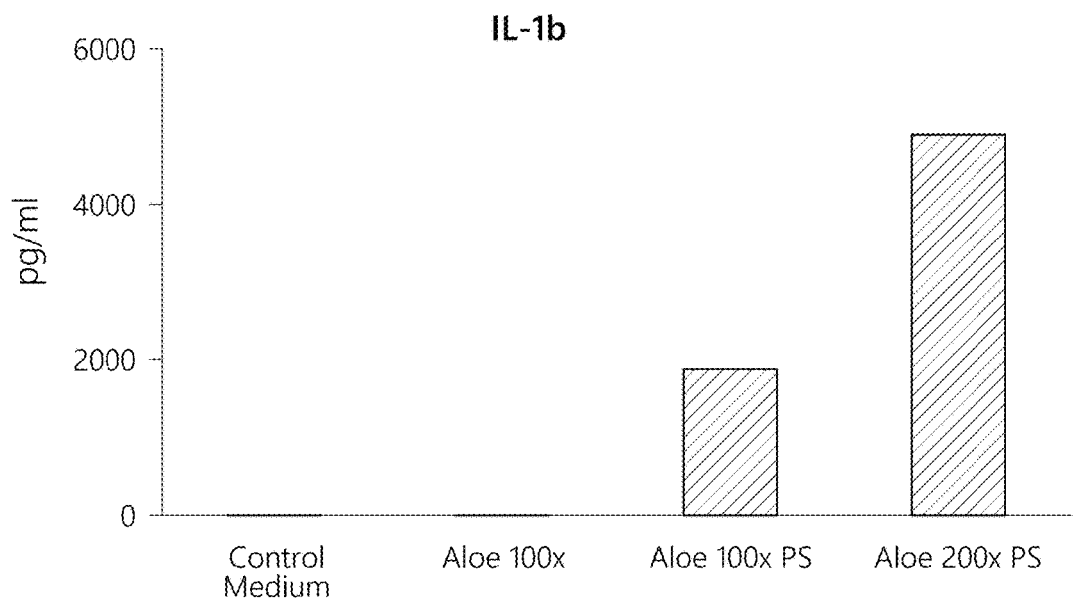
FIG. 33C (I)
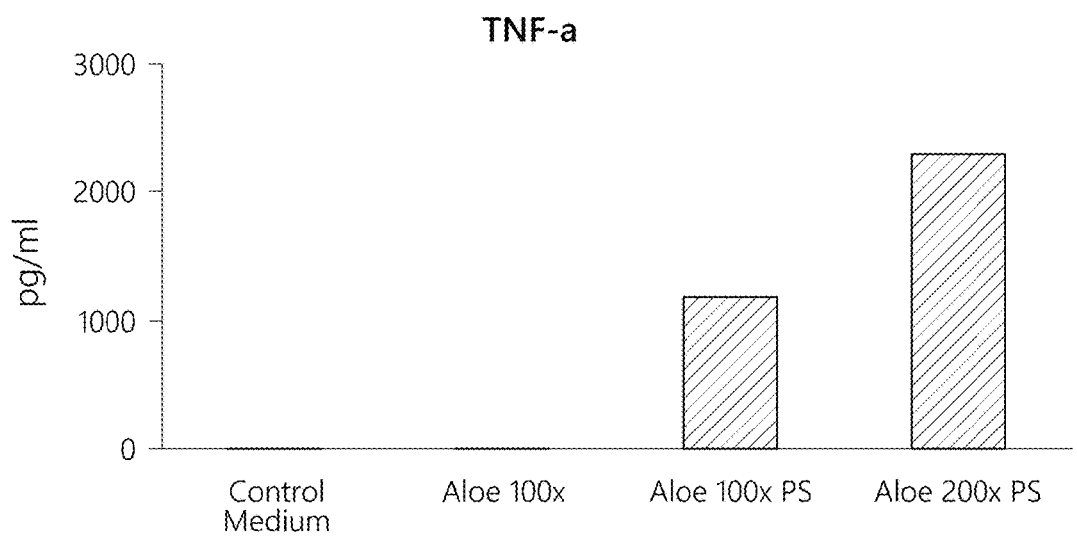
FIG. 33C (II)

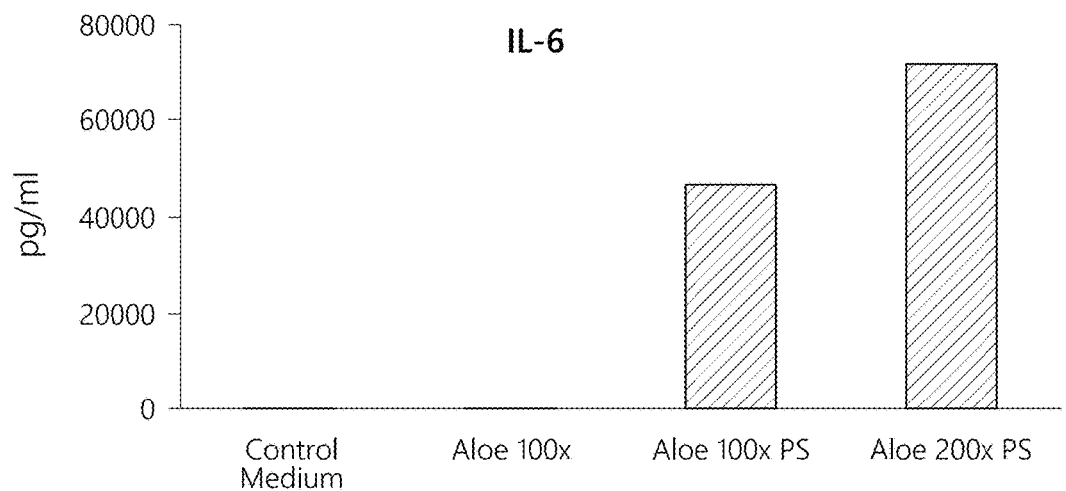
FIG. 33C (III)
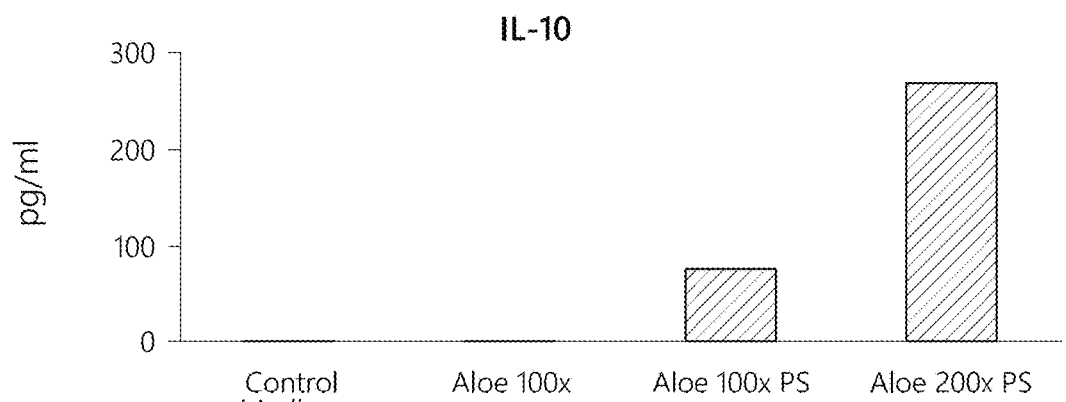
FIG. 33C (IV)
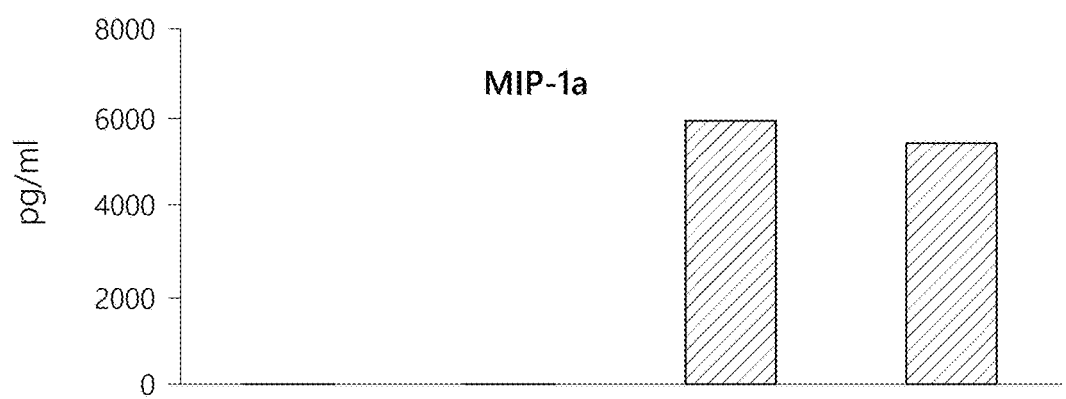
FIG. 33C (V)

METHODS OF TREATMENT USING PURIFIED (DECOLORIZED) ALOE VERA LEAF DRY JUICE

BACKGROUND

Field of the Disclosure

*Aloe vera* has been used as a traditional remedy for wound healing, supporting digestive health, and intestinal healing among other things. However, little is known about *aloe vera's* bioactivity and mechanism of action. As a natural ingredient, the composition varies with growing conditions as well as manufacturing process. Very limited information is available to correlate the chemical composition and bioactivity. This disclosure is the part of research effort to systematically evaluate *aloe vera's* composition, bioactivity and correlations between its structure and functionality.

The present disclosure is directed to the preferential growth of short chain fatty acids from bacterial fermentation of purified (decolorized) *aloe vera* leaf juice ingredient. It also discusses the effect on restoring microbiota communities in the intestine or stimulation of specific mucosal immune functions, thereby contributing to the treatment of specific conditions. The present disclosure further discusses the potential of biologically meaningful antioxidant protection and immune modulatory (i.e., both immune-enhancing and anti-inflammatory) activity of the composition disclosed.

The Simulator of the Human Intestinal Microbial Ecosystem (SHIME) is an in vitro continuous model and includes a succession of five reactors simulating the different parts of the human gastrointestinal tract. The SHIMS has been extensively used for more than 15 years for both scientific and industrial projects and has been validated with in vivo parameters. Upon stabilization of the microbial community in the different regions of the colon, a representative microbial community is established in the three colon compartments, which differs both in composition and functionally in the different colon regions. The present disclosure evaluates possible properties of daily repeated doses of *aloe vera*. The SHIMS model allows culturing of the complex intestinal microbial ecosystem over a comparatively long period and under representative conditions. The SHIIVIE also allows simulating repeated ingestion of the tested material.

SUMMARY OF CERTAIN INVENTIVE ASPECTS

In one aspect, a composition is disclosed that includes, for example, decolorized *aloe vera* juice, *aloe vera* concentrate and one or more excipients. In some embodiments, the composition further includes an acidity modifier. In some embodiments, the *aloe vera* concentrate is pure *aloe vera* juice, *aloe vera* juice 2× concentrate, *aloe vera* juice 25× concentrate, *aloe vera* juice 50× concentrate, *aloe vera* juice 75× concentrate, *aloe vera* juice 100× concentrate, *aloe vera* juice 125× concentrate, *aloe vera* juice 150× concentrate, *aloe vera* juice 175× concentrate, or *aloe vera* juice 200× concentrate.

In some embodiments, the excipient is a preservative. In some embodiments, the preservative is sorbic acid, sorbic acid salt, benzoic acid, benzoic acid salt, lactic acid, lactic acid salt, citric acid, citric acid salt, malic acid, malic acid salt, acetic acid, acetic acid salt, tartaric acid, tartaric acid salt, rosemary extract, lovage extract, chitosan, sage essential oil, thymol oil or nisin. In some embodiments, the excipient has a concentration of 0.01-2%. In some embodiments, the excipient has a concentration of 0.01-0.5%. In some embodiments, the excipient is a flavorant. In some embodiments the flavorant is one or more of sugar, honey, fructose, dextrose, maltodextrin, or gums. In some embodiments, the flavorant has a concentration of 0.1-50%. In some embodiments, the flavorant has a concentration of 0.1-20%. In some embodiments, the excipient is cellulose powder, modified starch, microcrystalline cellulose, magnesium stearate, stearic acid, sodium croscarmellose, calcium carbonate, dicalcium phosphate, or silicon dioxide.

In some embodiments, the acidity modifier is citric acid, citric acid salt, malic acid, malic acid salt, acetic acid, acetic acid salt, lactic acid, lactic acid salt, tartaric acid, or tartaric acid salt. In some embodiments, the acidity modifier has a concentration of 0.1-10%. In some embodiments, the acidity modifier has a concentration of 0.2-5%.

In some embodiments, the *aloe vera* juice is liquid juice, juice concentrate, or dry juice concentrate. In some embodiments, the *aloe vera* juice is derived from *aloe vera* whole leaf. In some embodiments, the *aloe vera* juice is derived from *aloe vera* inner gel. In some embodiments, the *aloe vera* juice includes not more than 10 ppm aloin. In some embodiments, the *aloe vera* juice includes not more than 3 ppm aloin. In some embodiments, the *aloe vera* juice includes at least 5% acetylated acemannan. In some embodiments, the *aloe vera* juice includes acetylated acemannan with molecular weight of 50,000 Dalton to 10,000,000 Dalton. In some embodiments, the *aloe vera* juice includes acetylated acemannan with molecular weight of 100,000 to 5,000,000 Dalton.

In another aspect, a nutritional supplement is disclosed that includes, for example, decolorized *aloe vera* juice, *aloe vera* concentrate and one or more excipients. In some embodiments, the nutritional supplement is a tablet, a capsule, a softgel, a gummy, an oral dissolved tablet, a powder, or a liquid. In some embodiments, the amount of decolorized *aloe vera* juice is 1-500 g. In some embodiments, the amount of decolorized *aloe vera* juice is 5-300 g. In some embodiments, the amount of decolorized *aloe vera* dry juice concentrate is 10-500 mg. In some embodiments, the amount of decolorized *aloe vera* dry juice concentrate is 50-300 mg.

A method of improving health and quantity of the microbiome in a mammal is also disclosed herein. The method includes administering an effective amount of a composition including decolorized *aloe vera* juice, *aloe vera* concentrate and one or more excipients.

A method for inducing a beneficial effect on the human microbiome is also disclosed herein. The method includes administering a composition to a mammal, the composition including decolorized *aloe vera* juice, *aloe vera* concentrate and one or more excipients.

In some embodiments, the beneficial effect on the human microbiome is an increased production of short chain fatty acids. In some embodiments, the beneficial effect on the human microbiome is an increased total microbial population in the colon. In some embodiments, the beneficial effect on the human microbiome is an increased production of acetate in the proximal colon. In some embodiments, the beneficial effect on the human microbiome is an increased production of propionate in the proximal colon. In some embodiments, the beneficial effect on the human microbiome is an increased population of the total bacteria in the proximal colon. In some embodiments, the beneficial effect on the human microbiome is an increased population of the transient concentration of bifidobacteria in the proximal colon. In some embodiments, the beneficial effect on the human microbiome is a strong anti-inflammatory response in the intestine. In some embodiments, the beneficial effect on the human microbiome is a decreased gut-barrier permeability in a co-culture system of Coca-2 cells and THP1macrophages. In some embodiments, gut permeability is measured by paracellular transport of Lucifer Yellow in a co-culture system of Caco-2 cells and THP 1 macrophages. In some embodiments, the beneficial effect on the human microbiome is a gut soothing effect.

In another aspect, a method for inducing a beneficial effect on a mammal is also disclosed herein. The method includes administering a composition to a mammal, the composition including decolorized *aloe vera* juice, *aloe vera* concentrate and one or more excipients.

In some embodiments, the beneficial effect on the mammal is an antioxidant benefit. In some embodiments, the antioxidant benefit is biologically meaningful antioxidant protection under conditions of oxidative stress. In some embodiments, the antioxidant benefit is activating and inhibiting signals to immune cells. In some embodiments, the antioxidant benefit is induction of a bi-phasic response to immune cells. In some embodiments, anti-inflammatory compounds are only allowed to show a response at lower doses while immune activating substances are active at a different dose range. In some embodiments, the antioxidant benefit is a strong anti-inflammatory response in intestine.

In some embodiments, the beneficial effect on the mammal is an anti-inflammatory activity of decolorized *aloe vera* leaf juice concentrate, *aloe vera* inner leaf juice concentrate, and dry inner leaf gel. In some embodiments, the beneficial effect on the human immune system is a decreased production of inflammatory cytokines and chemokines from the peripheral blood mononuclear cells (PBMCs) when co-cultured with a pro-inflammatory stimulus such as lipopolysaccharide (LPS). In some embodiments, the beneficial effect on the mammal is an immune modulatory, i.e., both immune-enhancing and anti-inflammatory, activity of *aloe vera* inner leaf concentrate and polysaccharide (i.e., acemannan)-enriched fractions of decolorized *aloe vera* leaf juice concentrate and *aloe vera* inner leaf juice concentrate, respectively. In some embodiments, the beneficial effect on the human immune system is both an increased production of inflammatory cytokines and chemokines and an increased production of anti-inflammatory cytokines from the peripheral blood mononuclear cells (PBMCs), in the absence of any pro-inflammatory stimulus.

In some embodiments, the beneficial effect on the mammal is an immune-enhancing activity of decolorized *aloe vera* leaf juice. In some embodiments, the beneficial effect on the human immune system is the activation of immune cells that include natural killer (NK) cells, T lymphocytes, and natural killer T (NKT) lymphocytes, respectively.

In some embodiments, the beneficial effect on the mammal is anti-inflammatory activity of decolorized *aloe vera* leaf juice. In some embodiments, the beneficial effect on the murine immune system is an increase in the production of anti-inflammatory, Th2-type cytokines such as IL-10 and IL-5 from the co-culture of dendritic cells (DCs) and CD4(+) T cells and also in a decrease in IFN-γ, a Th1-type cytokine. In some embodiment, the beneficial effect on the murine immune system is the promotion of the switching or polarization of inflammatory M1 macrophages into anti-inflammatory, M2 macrophages.

BRIEF DESCRIPTION OF THE DRAWINGS

FIG. 21 shows graphical summary of the effect of the test products on the host parameters. Yellow cells (Y) are =1.0, and depict the controls: gM or LPS for the non-digested products or for the samples collected in the control period for the SHIIVIE; Green (G) cells depict values >1, thus an increase relatively to the control; Red (R) cells depict values <1, thus a decrease relatively to the control. The extent of change from 1.0 is represented by color intensity. The boxes are filled with the letter Y, G, or R to depict Yellow, Red or Green. No indication means the box is white.

FIG. 33A(I) is a graphical depiction of a cytokine assay using human PBMC cells from a healthy donor. The bar graph shows the average concentration of MIP-1α, a chemokine that is secreted from PBMCs into the culture medium 24 hours after the cells were treated with 100 ug/ml of decolorized aloe vera leaf dry juice in the presence of 50 pg/ml of lipopolysaccharide (LPS), an inflammatory stimulant. The average value from duplicates per each cytokine is given.

FIG. 33A(II) is a graphical depiction of a cytokine assay using human PBMC cells from a healthy donor. The bar graph shows the average concentration of TNF-α, a a chemokine that is secreted from PBMCs into the culture medium 24 hours after the cells were treated with 100 ug/ml of decolorized aloe vera leaf dry juice in the presence of 50 pg/ml of lipopolysaccharide (LPS), an inflammatory stimulant. The average value from duplicates per each cytokine is given.

FIG. 33A(III) is a graphical depiction of a cytokine assay using human PBMC cells from a healthy donor. The bar graph shows the average concentration of MIP-1α, a cytokine that is secreted from PBMCs into the culture medium 24 hours after the cells were treated with 100 ug/ml of decolorized aloe vera leaf dry juice polysaccharide (PS)-enriched in the presence of 50 pg/ml of lipopolysaccharide (LPS), an inflammatory stimulant. The average value from duplicates per each cytokine is given.

FIG. 33A(IV) is a graphical depiction of a cytokine assay using human PBMC cells from a healthy donor. The bar graph shows the average concentration of TNF-α 24 hours after the cells were treated with 100 ug/ml of decolorized aloe vera leaf dry juice polysaccharide (PS)-enriched in the presence of 50 pg/ml of lipopolysaccharide (LPS), an inflammatory stimulant. The average value from duplicates per each cytokine is given.

FIG. 33B(I) is a graphical depiction of a cytokine assay using human PBMC cells from a healthy donor. The bar graph shows the average concentration of MIP-1α, a cytokine that is secreted from PBMCs into the culture medium 24 hours after the cells were treated with 100 ug/ml of aloe vera inner leaf juice concentrate in the presence of 50 pg/ml of lipopolysaccharide (LPS), an inflammatory stimulant. The average value from duplicates per each cytokine is given.

FIG. 33B(II) is a graphical depiction of a cytokine assay using human PBMC cells from a healthy donor. The bar graph shows the average concentration of TNF-α, a chemokine that is secreted from PBMCs into the culture medium 24 hours after the cells were treated with 100 ug/ml of aloe vera inner leaf juice concentrate in the presence of 50 pg/ml of lipopolysaccharide (LPS), an inflammatory stimulant. The average value from duplicates per each cytokine is given.

FIG. 33B(III) is a graphical depiction of a cytokine assay using human PBMC cells from a healthy donor. The bar graph shows the average concentration of IL-10 24 hours after the cells were treated with 100 ug/ml of aloe vera inner leaf juice concentrate polysaccharide (PS)-enriched in the presence of 50 pg/ml of lipopolysaccharide (LPS), an inflammatory stimulant. The average value from duplicates per each cytokine is given.

FIG. 33C (I to V) is a graphical depiction of a cytokine assay using human PBMC cells from a healthy donor. The bar graph shows the average concentration of cytokines and chemokines[IL-1β (I), TNF-α (II), IL-6 (III), IL-10 (IV), and MIP-1α (V)] that are secreted from PBMCs into the culture medium 24 hours after the cells were treated with 100 ug/ml of aloe vera inner leaf juice concentrate in the absence of an inflammatory stimulant. The average value from duplicates per each cytokine is given.

DETAILED DESCRIPTION OF CERTAIN PREFERRED EMBODIMENTS

I. Introduction

Figure 1:
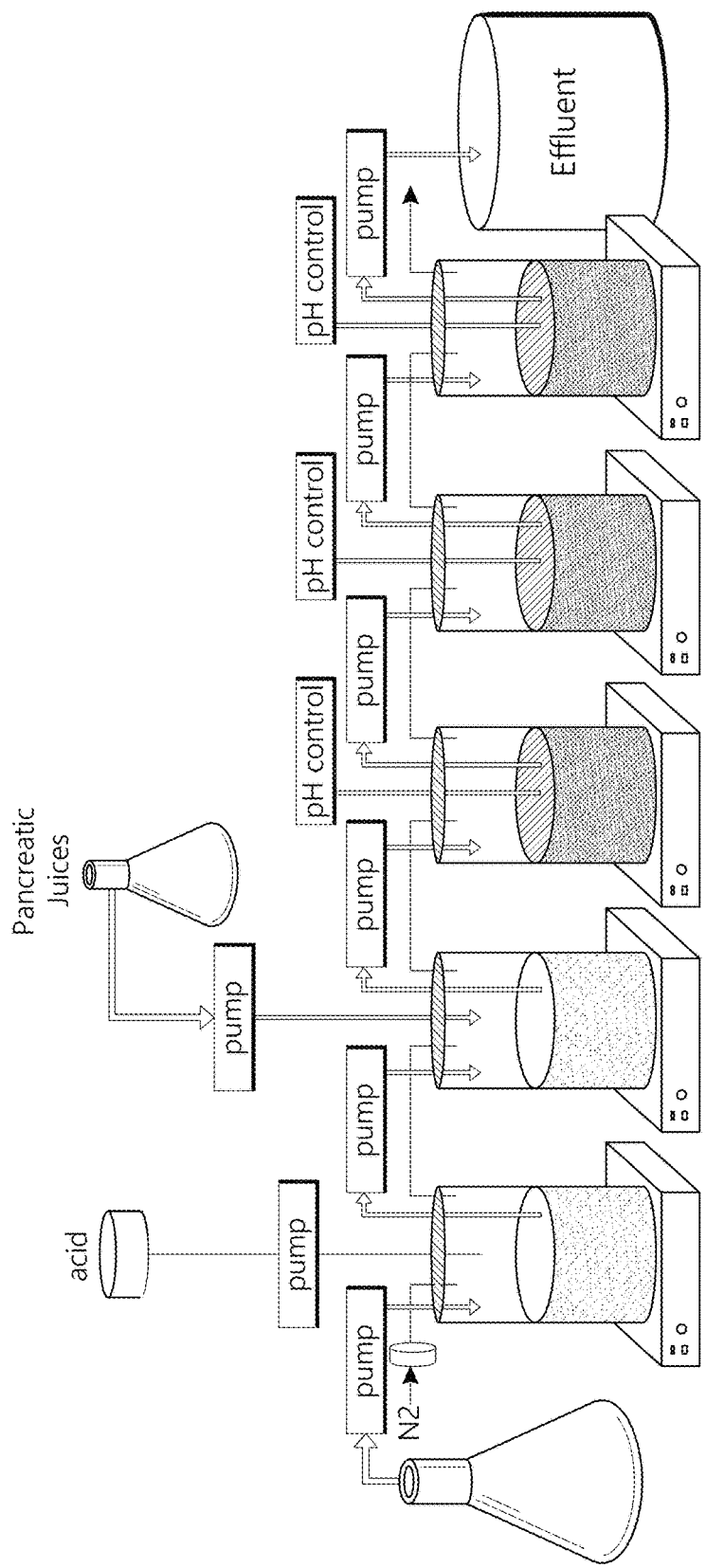
FIG. 1 shows a standard setup of the (SHIME), having 5 sequential reactors which simulate the different regions of the human intestinal tract.

In vitro approaches to study the gastrointestinal (GI) tract and intestinal microbial processes offer an excellent experimental setup to study possible properties of selected food ingredients. The application of well-designed continuous models allows the in-depth study of the biological activity of selected molecules in the gut under representative environmental conditions. Furthermore, recent advances in in vitro modeling also allows combining the study of bacteria-host interactions with the continuous model, thereby further increasing both the scientific output and commercial relevance.

Leaky Gut is studied nowadays because it is supposed to be involved in some serious health troubles or diseases, such as chronic fatigue syndrome, IBS, metabolic disorders, inflammatory bowel diseases, type 1 diabetes, allergies, asthma, and autoimmune disease. In fact, Leaky Gut identifies the association between disrupted intestinal barrier function and the development of autoimmune and inflammatory diseases. The epithelium maintains its selective barrier function through the formation of complex protein-protein networks that mechanically link adjacent cells and seal the intercellular space. An improper functioning or regulation of the tight junctions may be responsible to larger intercellular spaces with luminal element passage through the barrier, with a consecutive local and systemic inflammation.

Chronic inflammation is a pathological condition characterized by continued active inflammation response and tissue destruction. Many studies suggest that chronic inflammation could have a serious role in a wide variety of age-related diseases including diabetes, cardiovascular and autoimmune diseases. Inflammatory processes induce oxidative stress and reduce cellular antioxidant capacity. Overproduced free radicals react with cell membrane fatty acids and proteins, impairing their function permanently. In addition, free radicals can lead to mutation and DNA damage that can be a predisposing factor for cancer and age-related disorders.

Many of the immune cells including macrophages, neutrophils and eosinophils are involved directly or by production of inflammatory cytokine production in pathology of chronic inflammation. The direct immune modulating effects and regulation of immune and inflammatory process by *aloe vera* can be measured by direct cellular activation of NK cells, NKT cells, T lymphocytes, monocytes, and macrophages.

The present disclosure evaluates possible properties of daily repeated doses of *aloe vera*. The SHIME model allows an approximation and culturing of the complex intestinal microbial ecosystem over a long period and under representative conditions. The SHIME also allows simulating repeated ingestion of the tested material. In the present disclosure, the microbial community composition and activity by repeated dosing of *aloe vera* and effect on the gut barrier permeability and inflammation were evaluated. The Felin-Ciocalteo assay method is a method to measure the total phenolic content in a material, which is the indicator of anti-oxidant capacity of the material. To assess the antioxidant potential, a cell-based antioxidant protection assay may be performed. In this test, only the antioxidants that are able to cross the lipid bilayer cell membrane, enter the cells and provide biologically meaningful antioxidant protection under conditions of oxidative stress are measured.

The composition disclosed herein includes several advantages. One advantage is short chain fatty acid production. Compositions of the present disclosure show a linear dose response with both the total and individual short chain fatty acid production. Further, administered (or ingested) purified (decolorized) *aloe vera* leaf dry juice lead to a higher acetate and propionate production in the proximal colon. Another advantage of the composition presently disclosed is its impact on the gut microbial composition. At a 0.507 g/L concentration, the test sample led to a slight increase of total bacteria in the proximal colon mainly associated to an increase in bacteroidetes. The concentration of bifidobacteria showed a transient peak after two weeks of treatment. At a 1.014 g/L concentration, purified (decolorized) *aloe vera* leaf dry juice leads to an increase of total bacteria (Bacteroidetes and Firmicutes), and a transient concentration of bifidobacteria. Yet another advantage of the presently disclosed composition is its positive effect on Caco-2 barrier integrity. At a 1.014 g/L concentration, unfermented purified (decolorized) *aloe vera* leaf dry juice can maintain the trans-epithelial electrical resistance (TEER) by protecting the Caco-2 cells from damage induced by THP1 cells, thereby having a positive effect on Caco-2 barrier integrity. Another advantage of the compositions disclosed herein includes its positive effect on IL-10 levels, IL-6 levels, IL-8 levels, and TNF-α levels. At a 1.014 g/L concentration, unfermented purified (decolorized) *aloe vera* leaf dry juice is able to increase LPS-induced IL-10 levels (a bona fide anti-inflammatory cytokine), to maintain IL-6 levels and to decrease both LPS-induced IL-8 and TNF-α levels. Yet another advantage of the presently disclosed composition is that it provides a biologically meaningful antioxidant protection under conditions of oxidative stress.

The present disclosure further evaluates the anti-inflammatory and immune modulatory properties of the composition disclosed herein, as measured in a cytokine release assay employing a population of immune cells called peripheral blood mononuclear cells (PBMCs). The cells were cultured in the presence of lipopolysaccharide (LPS) or polyinosinic:polycytidylic (poly I:C) acid, potent inflammatory stimulants mimicking bacterial infection and viral insult respectively, and treated with aloe test material. The concentration of cytokine or chemokine secreted from PBMCs was measured via Enzyme-Linked Immunosorbent Assay (ELISA). The PBMC-based immunological assay revealed the following advantages of the aloe composition. First, in the range of concentrations between 10 ug/ml and 100 ug/ml, *aloe vera* leaf juice concentrate that contained the 4.3 to 55.9 percent of polysaccharides demonstrated an anti-inflammatory and/or an immune modulatory activity (both immune-enhancing and anti-inflammatory), as it decreased the LPS-stimulated expression of MIP-1α and/or TNF-α from PBMCs. Second, in the range of concentrations between 0.1 ug/ml and 100 ug/ml, *aloe vera* inner leaf juice concentrate that contained the 8.8 to 82 percent of polysaccharides showed an anti-inflammatory and/or an immune modulatory activity (both immune-enhancing and anti-inflammatory), as it decreased the LPS-stimulated expression of TNF-α and MIP-1α from PBMCs while increasing IL-10 if the content of polysaccharide was higher.

Figure 34A:
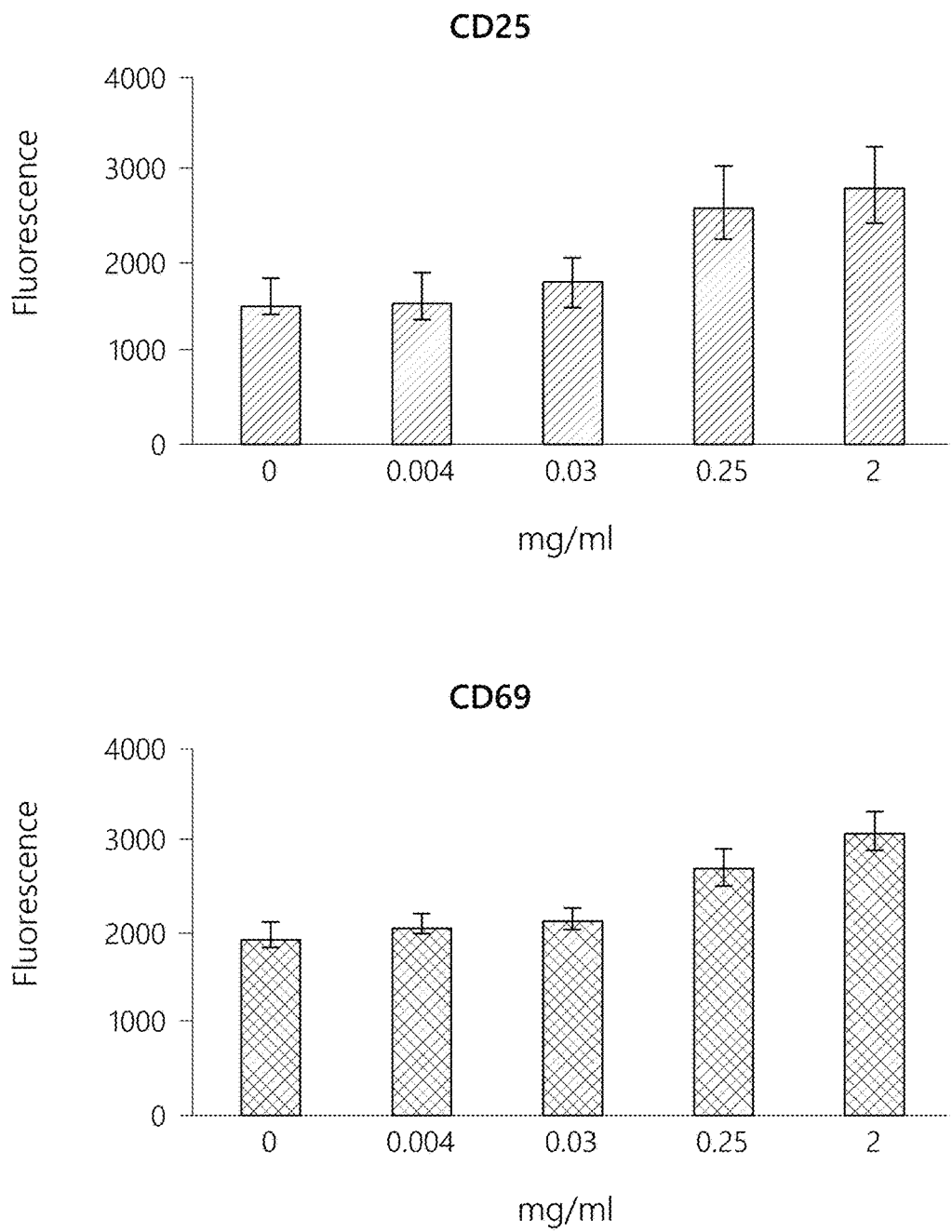
FIG. 34A is a graphical depiction of multi-parameter flow cytometry employing fluorescent monoclonal antibodies specific for the cell surface markers CD3, CD25, CD56, and CD69, respectively. Anti-CD3 and anti-CD56 monoclonal antibodies were used to differentiate CD3(−)CD56(+) NK cells in the PBMCs of a healthy donor, while anti-CD25 and anti-CD69 antibodies were used to monitor the activation status. The mean value from the three replicates per each concentration was plotted.
Figure 34B:
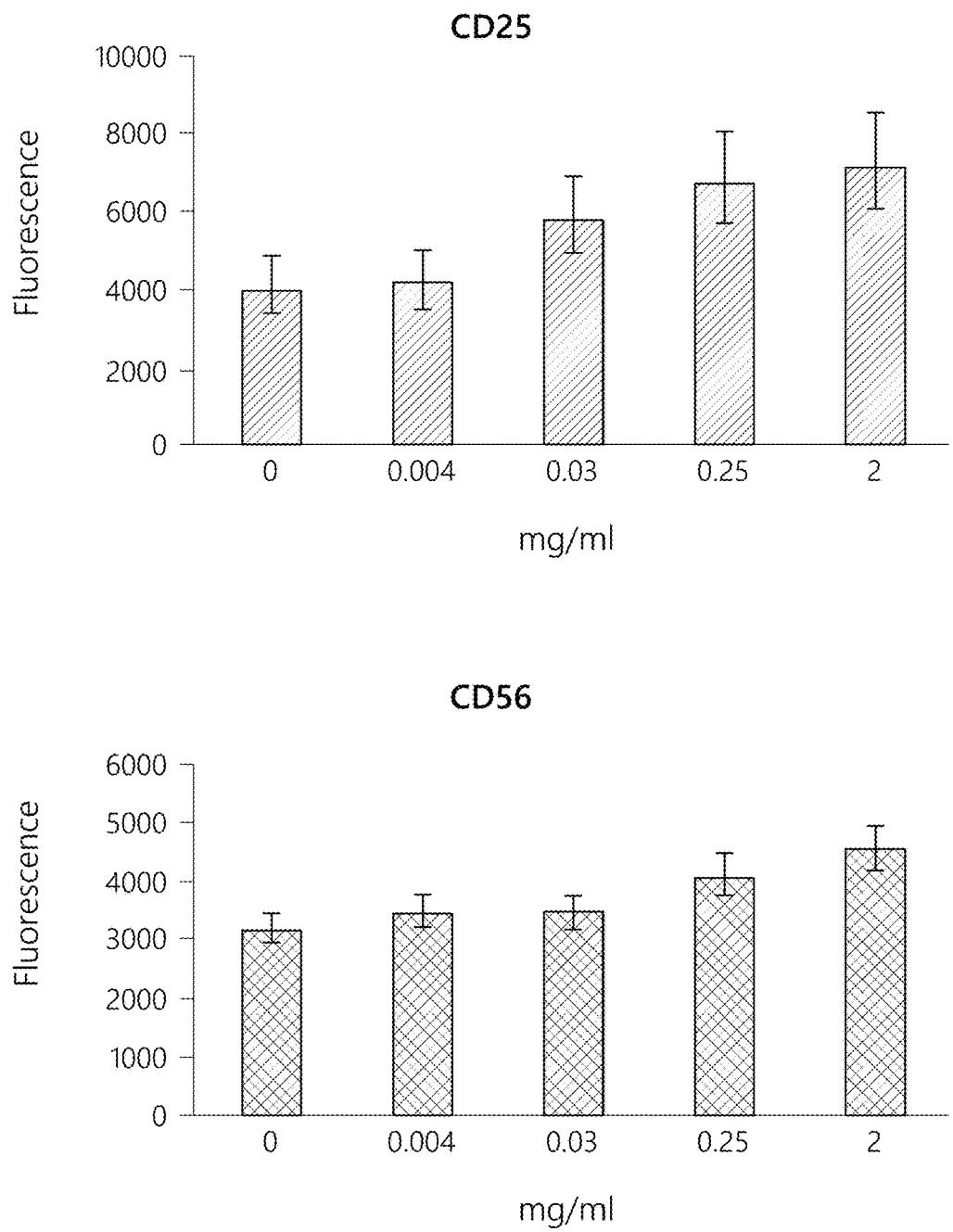
FIG. 34B is a graphical depiction of multi-parameter flow cytometry assay employing fluorescent monoclonal antibodies specific for the cell surface markers CD3, CD25, CD56, and CD69, respectively. Anti-CD3 and anti-CD56 monoclonal antibodies were used to differentiate CD3(+)CD56(+) NKT cells in the PBMCs of a healthy donor, while anti-CD25 and anti-CD69 antibodies were used to monitor the activation status. The mean value from the three replicates per each concentration was plotted.

The immune modulatory activities of the composition disclosed herein were further assessed by multi-parameter flow cytometry to determine the nature of immune cells and their activation status (FIGS. 34A-34B). PBMCs derived from a healthy donor were cultured with 0.004 mg/ml to 2 mg/ml of *aloe vera* leaf juice concentrate. In order to detect natural killer cells, [NK, CD3(−)/CD56(+)] and NKT [CD3

(+)/CD56(+)] (which were essential not only for innate but also for adaptive immune responses), anti-CD3 and anti-CD56 monoclonal antibodies were used. On the other hand, anti-CD25 and anti-69 monoclonal antibodies were used to determine whether these immune cells could be directly activated by *aloe vera* leaf juice concentrate. The flow cytometry revealed the following advantages of the aloe composition. First, *aloe vera* leaf juice concentrate directly activated NK cells, which are essential for the primary defense against pathogenic microorganisms and abnormal cells such as cancer cells arising in the body. Second, the aloe composition directly activated NKT cells, which play an important role in regulating autoimmune diseases, atherosclerosis, and cancers.

Figure 35A:
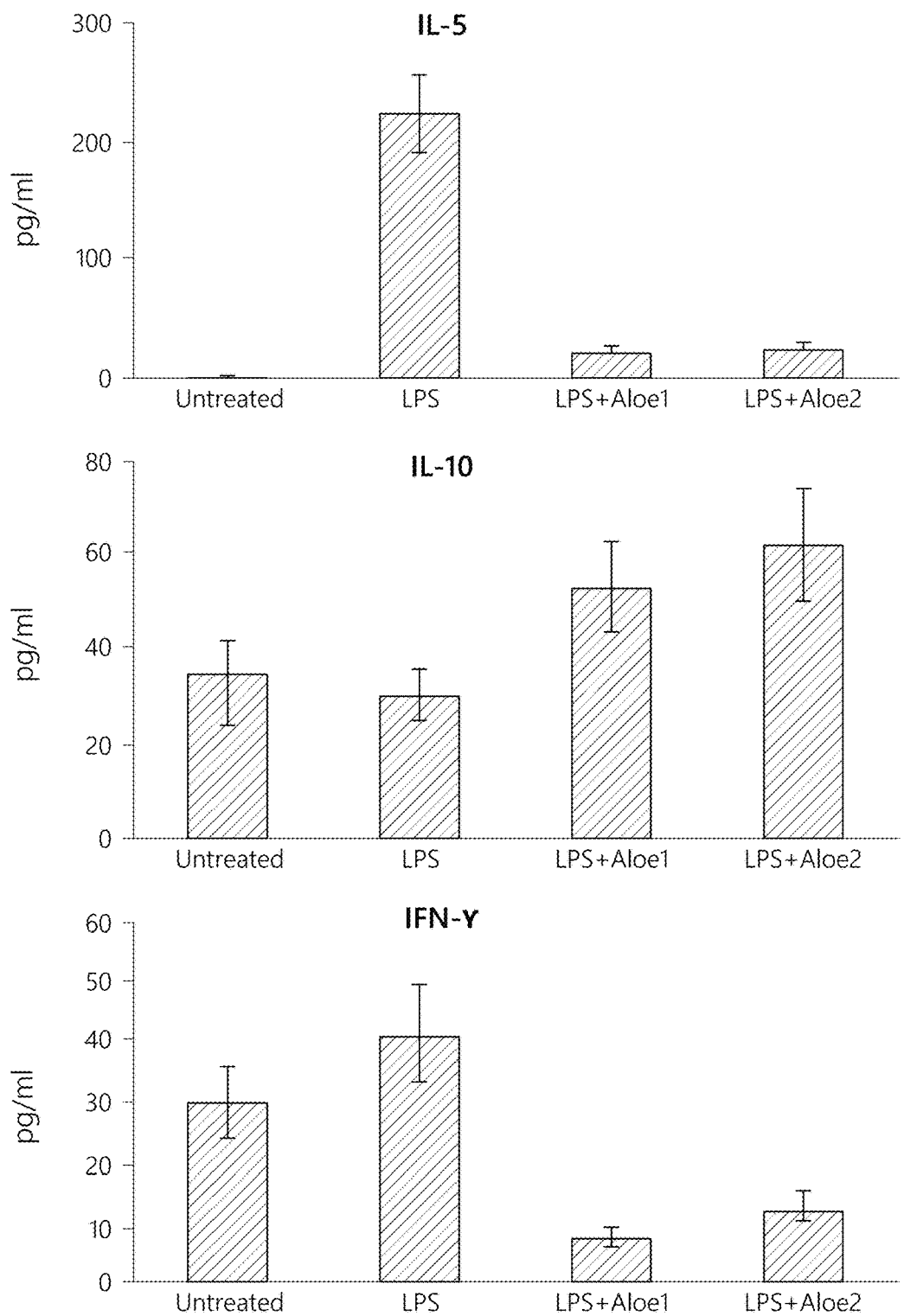
FIG. 35A is a graphical depiction of a cytokine assay to measure the production of Th1 (IFN-γ) and Th2-type (IL-5 and IL-10) cytokines from co-cultures of CD4 T lymphocytes with murine, bone marrow-derived DCs activated by LPS in the absence or presence of aloe vera leaf juice (Aloe1 or Aloe2) composition. The bar graph shows the average concentration from triplicates per each cytokine secreted from the co-cultures into the medium for 24 hours.
Figure 35B:
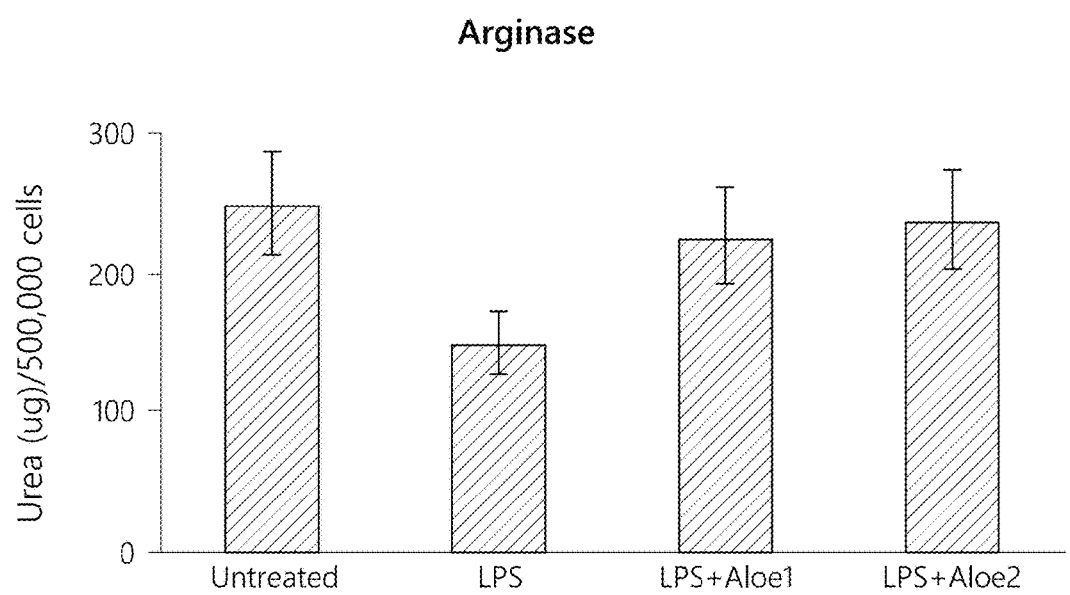
FIG. 35B is a graphical depiction of arginase activity assay to measure the polarization and function of murine, bone marrow-derived macrophages activated by LPS in the absence or presence of aloe vera leaf juice (Aloe1 or Aloe2) composition. The bar graph shows the average production of urea (ug/500,000 cells) from triplicates per each assay.

Anti-inflammatory activity of the composition disclosed herein was further assessed by Th1- and Th2-type cytokine production from CD4 T cells co-cultured with dendritic cells (DCs) activated by LPS in the absence or presence of *aloe vera* leaf juice concentrate (0.507 mg/ml) (FIG. 35A). The cytokine assay revealed the following advantages of the aloe composition. First, the aloe composition significantly elevated the production of anti-inflammatory Th2-type cytokines such as IL-10 and IL-5. Second, the aloe composition significantly reduced the production of inflammatory Th1-type cytokine such as IFN-γ. Third, the aloe composition led to the differentiation of anti-inflammatory tolerogenic DCs. On the other hand, anti-inflammatory activity of the composition disclosed herein was further evaluated by arginase activity assay which measured the production of urea (ug) from macrophages (500,000 cells) activated by LPS in the absence or presence of *aloe vera* leaf juice concentrate (0.507 mg/ml). The arginase assay revealed the following advantage of the aloe composition that it promoted the switching or polarization of inflammatory M1 macrophages into anti-inflammatory M2 macrophages.

II. Aloe Product

The aloe product disclosed herein include decolorized *aloe vera*, *aloe vera* juice concentrate, polysaccharide-enriched fractions of decolorized *aloe vera* and of *aloe vera* juice concentrate, *aloe vera* inner leaf, and one or more excipients.

The *aloe vera* juice may be liquid juice, juice concentrate, or dry juice concentrate. In some embodiments, the *aloe vera* juice may include not more than 3 ppm aloin. In some embodiments, the *aloe vera* juice may include not more than about 10 ppm aloin. In some embodiments, the *aloe vera* juice may include not more than about 1 ppm, 2 ppm, 4 ppm, 5 ppm, 6 ppm, 7 ppm, 8 ppm, or 9 ppm aloin.

The *aloe vera* juice may include at least 5% acetylated acemannan. In some embodiments, the molecular weight of the acetylated acemannan may be 50,000 Dalton to 10,000,000 Dalton. In some embodiments, the molecular weight of the acetylated acemannan may be 100,000 to 5,000,000 Dalton. In some embodiments, the molecular weight of the acetylated acemannan may be 50,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 1,050,000, 1,100,000, 1,150,000, 1,200,000, 1,250,000, 1,300,000, 1,350,000, 1,400,000, 1,450,000, 1,500,000, 1,550,000, 1,600,000, 1,650,000, 1,700,000, 1,750,000, 1,800,000, 1,850,000, 1,900,000, 1,950,000, 1,000,000, 2,000,000, 2,050,000, 2,100,000, 2,150,000, 2,200,000, 2,250,000, 2,300,000, 2,350,000, 2,400,000, 2,450,000, 2,500,000, 2,550,000, 2,600,000, 2,650,000, 2,700,000, 2,750,000, 2,800,000, 2,850,000, 2,900,000, 2,950,000, 3,000,000, 3,050,000, 3,100,000, 3,150,000, 3,200,000, 3,250,000, 3,300,000, 3,350,000, 3,400,000, 3,450,000, 3,500,000, 3,550,000, 3,600,000, 3,650,000, 3,700,000, 3,750,000, 3,800,000, 3,850,000, 3,900,000, 3,950,000, 4,000,000, 4,050,000, 4,100,000, 4,150,000, 4,200,000, 4,250,000, 4,300,000, 4,350,000, 4,400,000, 4,450,000, 4,500,000, 4,550,000, 4,600,000, 4,650,000, 4,700,000, 4,750,000, 4,800,000, 4,850,000, 4,900,000, 4,950,000, 5,000,000 Daltons or any number in between these values.

The *aloe vera* concentrate may be pure *aloe vera* juice. The *aloe vera* juice may be *aloe vera* juice 2× concentrate. The *aloe vera* juice may be *aloe vera* juice about 5×, 10×, 15×, 20×, 25×, 30×, 35×, 40×, 45×, 50×, 55×, 60×, 65×, 70×, 75×, 80×, 85×, 90×, 95×, 100×, 5×, 10×, 15×, 20×, 25×, 30×, 35×, 40×, 45×, 50×, 55×, 60×, 65×, 70×, 75×, 80×, 85×, 90×, 95×, 100×, 105×, 110×, 115×, 120×, 125×, 130×, 135×, 140×, 145×, 150×, 155×, 160×, 165×, 170×, 175×, 180×, 185×, 190×, 195×, 200× concentrate or any number in between these values.

The *aloe vera* product may also include an acidity modifier. The acidity modifier may be citric acid, citric acid salt, malic acid, malic acid salt, acetic acid, acetic acid salt, lactic acid, lactic acid salt, tartaric acid, or tartaric acid salt, formic acid and salt, propionic acid and salt, butyric acid and salt, valeric acid and salt, phosphoric acid and salt In one embodiment, the acidity modifier may have a concentration of 0.1-10%. In some embodiments, the acidity modifier may have a concentration of 0.2-5%. In another embodiment an acidity modifier may have a concentration of exactly or about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0% or any number in between these values.

In some embodiments, the concentration of the excipient is 0.01-2%. In some embodiments, the concentration of the excipient is 0.01-0.5%. In another embodiment an acidity modifier may have a concentration of exactly or about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0% or any number in between these values.

In some embodiments, the excipient in the *aloe vera* product is a preservative. The preservative may be sorbic acid, sorbic acid salt, benzoic acid, benzoic acid salt, lactic acid, lactic acid salt, citric acid, citric acid salt, malic acid, malic acid salt, acetic acid, acetic acid salt, tartaric acid, tartaric acid salt, rosemary extract, lovage extract, chitosan, sage essential oil, thymol oil, nisin, e-polylysine, grape seed extract, goji berry extract and or combination thereof.

In some embodiments, the excipient is cellulose powder, modified starch, microcrystalline cellulose, magnesium stearate, stearic acid, sodium croscarmellose, calcium carbonate, dicalcium phosphate, or silicon dioxide.

In some embodiments, the *aloe vera* product includes a flavorant. In some embodiments, the flavorant is one or more sugar, honey, fructose, dextrose, maltodextrin, or gums, natural and/or artificial flavors defined in 21 CFR 101.22(a)(3) and (EC) No 1334/2008.

In some embodiments, the concentration of the flavorant is 0.1-50%. In another embodiment a flavorant may have a concentration of exactly or about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 15.4%, 15.5%, 15.6%, 15.7%, 15.8%, 15.9%, 16.0%, 16.1%, 16.2%, 16.3%, 16.4%, 16.5%, 16.6%, 16.7%, 16.8%, 16.9%, 17.0%, 17.1%, 17.2%, 17.3%, 17.4%, 17.5%, 17.6%, 17.7%, 17.8%, 17.9%, 18.0%, 18.1%, 18.2%, 18.3%, 18.4%, 18.5%, 18.6%, 18.7%, 18.8%, 18.9%, 19.0%, 19.1%, 19.2%, 19.3%, 19.4%, 19.5%, 19.6%, 19.7%, 19.8%, 19.9%, 20.0%, 20.1%, 20.2%, 20.3%, 20.4%, 20.5%, 20.6%, 20.7%, 20.8%, 20.9%, 21.0%, 21.1%, 21.2%, 21.3%, 21.4%, 21.5%, 21.6%, 21.7%, 21.8%, 21.9%, 22.0%, 22.1%, 22.2%, 22.3%, 22.4%, 22.5%, 22.6%, 22.7%, 22.8%, 22.9%, 23.0%, 23.1%, 23.2%, 23.3%, 23.4%, 23.5%, 23.6%, 23.7%, 23.8%, 23.9%, 24.0%, 24.1%, 24.2%, 24.3%, 24.4%, 24.5%, 24.6%, 24.7%, 24.8%, 24.9%, 25.0%, 25.1%, 25.2%, 25.3%, 25.4%, 25.5%, 25.6%, 25.7%, 25.8%, 25.9%, 26.0%, 26.1%, 26.2%, 26.3%, 26.4%, 26.5%, 26.6%, 26.7%, 26.8%, 26.9%, 27.0%, 27.1%, 27.2%, 27.3%, 27.4%, 27.5%, 27.6%, 27.7%, 27.8%, 27.9%, 28.0%, 28.1%, 28.2%, 28.3%, 28.4%, 28.5%, 28.6%, 28.7%, 28.8%, 28.9%, 29.0%, 29.1%, 29.2%, 29.3%, 29.4%, 29.5%, 29.6%, 29.7%, 29.8%, 29.9%, 30.0%, 30.1%, 30.2%, 30.3%, 30.4%, 30.5%, 30.6%, 30.7%, 30.8%, 30.9%, 31.0%, 31.1%, 31.2%, 31.3%, 31.4%, 31.5%, 31.6%, 31.7%, 31.8%, 31.9%, 32.0%, 32.1%, 32.2%, 32.3%, 32.4%, 32.5%, 32.6%, 32.7%, 32.8%, 32.9%, 33.0%, 33.1%, 33.2%, 33.3%, 33.4%, 33.5%, 33.6%, 33.7%, 33.8%, 33.9%, 34.0%, 34.1%, 34.2%, 34.3%, 34.4%, 34.5%, 34.6%, 34.7%, 34.8%, 34.9%, 35.0%, 35.1%, 35.2%, 35.3%, 35.4%, 35.5%, 35.6%, 35.7%, 35.8%, 35.9%, 36.0%, 36.1%, 36.2%, 36.3%, 36.4%, 36.5%, 36.6%, 36.7%, 36.8%, 36.9%, 37.0%, 37.1%, 37.2%, 37.3%, 37.4%, 37.5%, 37.6%, 37.7%, 37.8%, 37.9%, 38.0%, 38.1%, 38.2%, 38.3%, 38.4%, 38.5%, 38.6%, 38.7%, 38.8%, 38.9%, 39.0%, 39.1%, 39.2%, 39.3%, 39.4%, 39.5%, 39.6%, 39.7%, 39.8%, 39.9%, 40.0%, 40.1%, 40.2%, 40.3%, 40.4%, 40.5%, 40.6%, 40.7%, 40.8%, 40.9%, 41.0%, 41.1%, 41.2%, 41.3%, 41.4%, 41.5%, 41.6%, 41.7%, 41.8%, 41.9%, 42.0%, 42.1%, 42.2%, 42.3%, 42.4%, 42.5%, 42.6%, 42.7%, 42.8%, 42.9%, 43.0%, 43.1%, 43.2%, 43.3%, 43.4%, 43.5%, 43.6%, 43.7%, 43.8%, 43.9%, 44.0%, 44.1%, 44.2%, 44.3%, 44.4%, 44.5%, 44.6%, 44.7%, 44.8%, 44.9%, 45.0%, 45.1%, 45.2%, 45.3%, 45.4%, 45.5%, 45.6%, 45.7%, 45.8%, 45.9%, 46.0%, 46.1%, 46.2%, 46.3%, 46.4%, 46.5%, 46.6%, 46.7%, 46.8%, 46.9%, 47.0%, 47.1%, 47.2%, 47.3%, 47.4%, 47.5%, 47.6%, 47.7%, 47.8%, 47.9%, 48.0%, 48.1%, 48.2%, 48.3%, 48.4%, 48.5%, 48.6%, 48.7%, 48.8%, 48.9%, 49.0%, 49.1%, 49.2%, 49.3%, 49.4%, 49.5%, 49.6%, 49.7%, 49.8%, 49.9%, 50.0% or any number in between these values.

The *aloe vera* composition may be used as part of a nutritional supplement. The nutritional supplement may be a tablet, a capsule, a softgel, a gummy, an oral dissolved tablet, a lozenge, a powder, or a liquid.

In some embodiments, the amount of decolorized *aloe vera* juice in the nutritional supplement is 1-500 g. In some embodiments, the amount of decolorized aloe vera juice in the nutritional supplement is 5-300 g. In some embodiments, the amount of decolorized *aloe vera* juice in the nutritional supplement is exactly or about 1g, 5 g, 10 g, 15 g, 20 g, 25 g, 30 g, 35 g, 40 g, 45 g, 50 g, 55 g, 60 g, 65 g, 70 g, 75 g, 80 g, 85 g, 90 g, 95 g, 100 g, 105 g, 110 g, 115 g, 120 g, 125 g, 130 g, 135 g, 140 g, 145 g, 150 g, 155 g, 160 g, 165 g, 170 g, 175 g, 180 g, 185 g, 190 g, 195 g, 200 g, 205 g, 210 g, 215 g, 220 g, 225 g, 230 g, 235 g, 240 g, 245 g, 250 g, 255 g, 260 g, 265 g, 270 g, 275 g, 280 g, 285 g, 290 g, 295 g, 300 g, 305 g, 310 g, 315 g, 320 g, 325 g, 330 g, 335 g, 340 g, 345 g, 350 g, 355 g, 360 g, 365 g, 370 g, 375 g, 380 g, 385 g, 390 g, 395 g, 400 g, 405 g, 410 g, 415 g, 420 g, 425 g, 430 g, 435 g, 440 g, 445 g, 450 g, 455 g, 460 g, 465 g, 470 g, 475 g, 480 g, 485 g, 490 g, 495 g, 500 g or any number in between these values.

In some embodiments, the amount of decolorized *aloe vera* juice in the nutritional supplement is 1-5 mg. In some embodiments, the amount of decolorized *aloe vera* juice in the nutritional supplement is 50-300 mg.

III. Preparation of the *aloe vera* Product

In one embodiment, the *aloe vera* product may be prepared in a large mixing tank, such as a 2000-gallon mixing tank. *aloe vera* juice and excipients may be added to the tank while the contents of the tank are mixed. One or more flavorants may then be added to tank. The final pH of the mixture may be about 2.9-3.4. The final pH of the mixture may be exactly or about 2.9, 3.0, 3.1, 3.2, 3.3, or 3.4 or any number in between these values. Water may be added to fill the mixing tank to capacity. The contents of the tank may then be processed through a heat exchanger at exactly or about 195° F. to form the product. The product may be cooled to ambient temperature before bottling.

In another embodiment, the *aloe vera* product may be prepared in a large mixing tank, such as a 40-gallon stainless steel mixing tank. *Aloe vera* juice and excipients may be added to the tank while the contents of the tank are mixed. While mixing, purified aloe vera dry juice powder and one or more flavorants may be added. Mixing may be continued until the *aloe vera* dry juice powder and one or more flavorants are completely dissolved. Additional flavorants and/or sweeteners may be added as well. Water may be added to fill the mixing tank to capacity. The contents of the tank may then be processed through a heat exchanger at exactly or about 195° F. to form the product and may be cooled to ambient temperature before bottling.

In another embodiment, the *aloe vera* product may be prepared in a blender. Dry *aloe vera* juice powder, maltodextrin, and sugar, may be added to the blender and mixed for exactly or about 5 minutes. Mixing may continue for exactly or about 6, 7, 8, 9, or 10 minutes. In a polyethylene bag or other suitable receptacle, excipients, anticaking agents, coloring agents and flavorants may be combined. The contents of the polyethylene bag may then be added to the blender. The contents of the blender may be mixed until homogenous to form the final product. The final product may be combined with exactly or about 4-8oz of water for consumption. In some embodiments, the final product may be combined with exactly or about 5, 6, or 7oz of water for consumption.

In one embodiment, the *aloe vera* product may be prepared in a v-blender. Purified dry *aloe vera* juice powder, excipients and anticaking agents may be added to the blender and mixed for exactly or about 10 minutes. The contents may be mixed for 1, 2, 3, 4, 5, 6, 7, 8, or 9 minutes or any number in between these values. Lubricant agents may be added to the blender, and the contents may be mixed for exactly or about 4 additional minutes to form a crude powder. The crude powder may then be encapsulated into a "0" hard shell capsule with a targeted fill weight of exactly or about 474 mg. The fill weight may range from exactly or about 450.3 mg to 497.7 mg. The fill weight may be exactly or about 450 mg, 455 mg, 460 mg, 465 mg, 470 mg, 475 mg, 480 mg, 485 mg, or 490 mg or any number in between these values. The final capsule may have a disintegration time of exactly or about no more than 30 minutes. The final capsule may have a disintegration time of exactly or about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes or any number in between these values.

In another embodiment, the *aloe vera* product may be prepared in a v-blender. Purified dry *aloe vera* juice powder, excipients, bulking agents and binding agents may be added to the blender and mixed for exactly or about 15 minutes. The contents may be mixed for 1, 2, 3, 4, 5, 6, 7, 8, 9, 10, 11, 12, 13, or 14 minutes or any number in between these values. Lubricant agents may be added to the blender, and the contents may be mixed for exactly or about 3 additional minutes to form a crude product. The crude product may be dropped into a portable container for tableting. Tableting may procced with a tableting press, operated under normal procedures. The press may be adjusted to have a target tablet weight of exactly or about 607 mg. The press may be adjusted to have a target tablet weight of exactly or about 576.7 mg to 637.4 mg. The press may be adjusted to have a target tablet weight of exactly or about 575 mg, 580 mg, 585 mg, 590 mg, 595 mg, 600 mg, 605 mg, 610 mg, 615 mg, 620 mg, 625 mg, 630 mg, 635 mg, or 640 mg or any number in between these values. The tablet hardness may be exactly or about 6-12 kp. The tablet hardness may be exactly or about 6 kp, 7 kp, 8 kp, 9 kp, 10 kp, 11 kp, or 12 kp or any kilopond (kp) between a range defined by any two aforementioned values. The tablet may have a disintegration time of exactly or about no more than 30 minutes. The tablet may have a disintegration time of exactly or about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes or any number in between these values.

In some embodiments, *aloe vera* whole leaf juice may be manufactured from mature *aloe vera* leaves. The mature *aloe vera* leaves may be harvested and transported to a processing plant within exactly or about 24 hours of harvest. The leaves may be washed and sanitized with chlorinated water. The tip and butt of the leaves may be mechanically removed. The remaining part of the leaf may then go through a grinder and then into a processing tank. At exactly or about 50-60° C., a suitable amount of an enzyme may be added into the tank. The temperature may be raised to exactly or about 85° C. after exactly or about 30 minutes. The raw juice may then be run through a finisher to remove cellular fiber. The juice may then be passed through activated charcoal to remove aloin to no more than exactly or about 0.1 ppm. The juice may then be used as-is. In some embodiments, the juice may be further concentrated via vacuum evaporation to *aloe vera* juice concentrate.

In some embodiments, *aloe vera* dry leaf juice may be manufactured from mature *aloe vera* leaves. The mature *aloe vera* leaves may be harvested and transported to a processing plant within exactly or about 24 hours of harvest. The leaves may be washed and sanitized with chlorinated water. The tip and butt of the leaves may be mechanically removed. The remaining part of the leaf may then go through a grinder and then into a processing tank. At exactly or about 50-60° C., a suitable amount of an enzyme may be added into the tank. The temperature may be raised to exactly or about 85° C. after exactly or about 30 minutes. The raw juice may then be run through a finisher to remove cellular fiber. The juice may then be passed through activated charcoal to remove aloin to no more than exactly or about 0.1 ppm. The juice may then be used as-is. The juice may be further processed to *aloe vera* dry juice powder by spray dry.

In some embodiments, *aloe vera* inner leaf juice may be manufactured from nature *aloe vera* leaves. The mature *aloe vera* leaves may be harvested and transported to a processing plant within exactly or about 24 hours of harvest. The leaves may be washed and sanitized with chlorinated water. The tip and butt of the leaves may be mechanically removed. The remaining part of the leaf may then go through a grinder and then into a processing tank. At exactly or about 50-60° C., a suitable amount of an enzyme may be added into the tank. The temperature may be raised to exactly or about 85° C. after exactly or about 30 minutes. The raw juice may then be run through a finisher to remove cellular fiber. The juice may then be passed through activated charcoal to remove aloin to no more than exactly or about 0.1 ppm. The juice may then be used as-is. In some embodiments, the juice may be further concentrated via vacuum evaporation to *aloe vera* juice concentrate.

In some embodiments, *aloe vera* inner leaf juice may be manufactured from nature *aloe vera* leaves. The mature *aloe vera* leaves may be harvested and transported to a processing plant within exactly or about 24 hours of harvest. The leaves may be washed and sanitized with chlorinated water. The tip and butt of the leaves may be mechanically removed. The remaining part of the leaf may then go through a grinder and then into a processing tank. At exactly or about 50-60° C., a suitable amount of an enzyme may be added into the tank. The temperature may be raised to exactly or about 85° C. after exactly or about 30 minutes. The raw juice may then be run through a finisher to remove cellular fiber. The juice may then be passed through activated charcoal to remove aloin to no more than exactly or about 0.1 ppm. The juice may then be used as-is. The juice may be further processed to *aloe vera* dry juice powder by spray dry.

In some embodiments, PS-enriched *aloe vera* fractions can be made by dissolving *aloe vera* dry juice in 85% ethyl alcohol. The solution can then be centrifuged and the supernatant is discarded and the ethanol-insoluble solid can be collected. The solid can be dried by appropriate drying methods such as freeze dry or reflectance window drying.

IV. Treatment

In some embodiments, the *aloe vera* composition described herein may be administered to a mammal to improve the health and quantity of the microbiome. In some embodiments, the mammal is a human.

In some embodiments, the *aloe vera* composition described herein may be administered to a mammal to induce beneficial effects on the human microbiome. Such beneficial effects on the human microbiome include, but are not limited to: an increased production of short chain fatty acids, an increased total microbial population in the colon, an increased production of acetate in the proximal colon, an increased production of propionate in the proximal colon, an increased population of the total bacteria in the proximal colon, an increased population of the transient concentration of bifidobacteria in the proximal colon, a strong anti-inflammatory response in the intestine, a decreased gut-barrier permeability in a co-culture system of Coca-2 cells and THP1 macrophages, or a gut soothing effect. Gut permeability may be measured by any suitable method known by a skilled artisan. In some embodiments, gut permeability may be measured by paracellular transport of Lucifer Yellow in a co-culture system of Caco-2 cells and THP1 macrophages.

In some embodiments, the *aloe vera* composition described herein may be administered to a mammal to induce a beneficial effect on a mammal. The beneficial effect may be an antioxidant benefit. Such antioxidant beneficial effects include but are not limited to: biologically meaningful antioxidant protection under conditions of oxidative stress, activating and inhibiting signals to immune cells, induction of a bi-phasic response to immune cells, wherein anti-inflammatory compounds are only allowed to show a response at lower doses while immune activating substances are active at a different dose range, and a strong anti-inflammatory response in intestine.

In some embodiments, the *aloe vera* composition disclosed herein may be used to treat leaky guy or other related indications.

In some embodiments, the *aloe vera* composition disclosed herein may be used to treat chronic inflammation, immune deficiency, immune disorders, or other related indications.

V. The SHIME® Experiment

In order to evaluate possible properties of daily repeated doses of the presently disclosed aloe product, a SHIME system may be used. The SHIME system is an in vitro continuous model, which allows culturing of the complex intestinal microbial ecosystem over a long period of time and under representative conditions. Moreover, the SHIME system allows for simulation of repeated ingestion of the test product. The reactor setup represents the gastrointestinal tract of the adult human.

The SHIME has a succession of five reactors simulating the different parts of the human gastrointestinal tract, as shown in FIG. 1. The first two reactors are of the fill-and-draw principle to simulate different steps in food uptake and digestion, with peristaltic pumps adding a defined amount of SHIME feed (140 mL 3×/day) and pancreatic and bile liquid (60 mL 3×/day), respectively to the stomach (V1) and duodenum (V2) compartment and emptying the respective reactors after specified intervals. The last three compartments are continuously stirred reactors with constant volume and pH control. Retention time and pH of the different vessels are chosen in order to resemble in vivo conditions in the different parts of the gastrointestinal tract. The overall residence time of the last three vessels, simulating the large intestine, is 72 h. Upon inoculation with fecal microbiota, these reactors simulate the ascending (V3), transverse (V4) and descending (V5) colon. Inoculum preparation, retention time, pH, temperature settings and reactor feed composition conditions are shown in the following table:

TABLE 1

Setup of the simulator of the human intestinal microbial ecosystem (SHIME) with reactor volumes and retention times listed

| Reactor | Volume (ml) | Residence time (h) | pH |
|---|---|---|---|
| R1: stomach | 200 | 4 | |
| R2: small intestine | 200 | 4 | |
| R3: ascending colon | 500 | 20 | 5.6-5.9 |
| R4: transverse colon | 800 | 32 | 6.1-6.4 |
| R5: descending colon | 600 | 24 | 6.6-6.9 |

The SHIME system has been extensively used for more than 15 years for both scientific and industrial projects and has been validated with in vivo parameters. Upon stabilization of the microbial community in the different regions of the colon, a representative microbial community is established in the three colon compartments, which differs both in composition and functionally in the different colon regions.

A. Analysis of the Microbial Community Composition and Activity

A number of microbial parameters may be monitored throughout the entire experiment. These measurements may be necessary to evaluate the performance of the model and allow monitoring of basic changes in the microbial community composition and activity due to the treatments as compared to the control period.

Short chain fatty acids (SCFA) samples may be taken 3×/week from all colon compartments to analyze the concentration of acetic acid, propionic acid, isobutyric acid, butyric acid, isovaleric acid, valeric acid, isocaproic acid and caproic acid. Moreover, samples from the stomach and the small intestine may be collected 3×/week to evaluate whether or not the SCFA stored in the products are released in the upper GIT.

Ammonium, is one of the markers for proteolysis. Samples may be taken 3×/week from all colon compartments to test for ammonium. As ammonium production is mainly the result of protein degradation and is associated with direct and indirect health detrimental effects, a reduction in ammonium production would therefore be considered as beneficial. Additionally, ammonium concentrations in the SHIME may also be seen as a marker for limited substrate availability for the bacteria during the treatment period or as a marker for a specific fermentation of the product itself.

The human intestine harbors both lactate-producing and lactate-utilizing bacteria. Lactate is produced by lactic acid bacteria and decreases the pH of the environment, acting also as an antimicrobial agent. It can also be rapidly converted to acetate, butyrate, and propionate by other microorganisms. Samples may be taken 1×/week from all colon compartments.

The consumption of acid and base may be recorded to evaluate the colonic acidification along the experiment Additional samples may be collected to analyze the host-bacteria interaction and the effect of the test products on the potential markers related to inflammation and gut permeability.

B. Microbial Community Composition

Quantitative PCR (qPCR) is a molecular technique which is based on the amplification of specific bacterial sequences (16S rRNA genes), combined with the quantification of the number of these specific sequences in the microbial ecosystem at different time points. qPCR is typically used to quantify the total bacterial community, specific bacterial groups or specific bacterial species. As this technique is not dependent on the (lack of) culturability of the bacteria, data generated with this method offer a more reliable overview on quantitative effects on the microbial community, due to the specific treatments.

Specific quantitative PCR (qPCR) protocols may be used to monitor total bacteria, Bifidobacteria, Lactobacilli, Firmicutes, and Bacteroidetes.

C. Host-Microbiota Interaction Analyses

Figure 4:
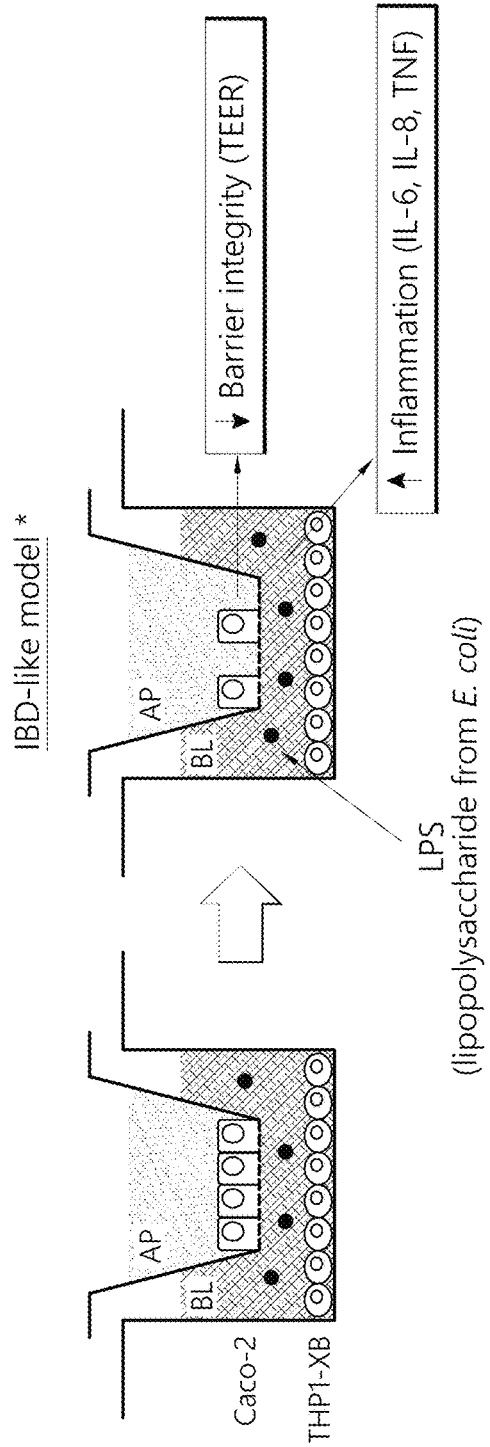
FIG. 4 shows a co-culture system of Caco-2 cells and THP1 macrophages composed of an apical (AP) and basolateral (BL) side.
Figure 5:
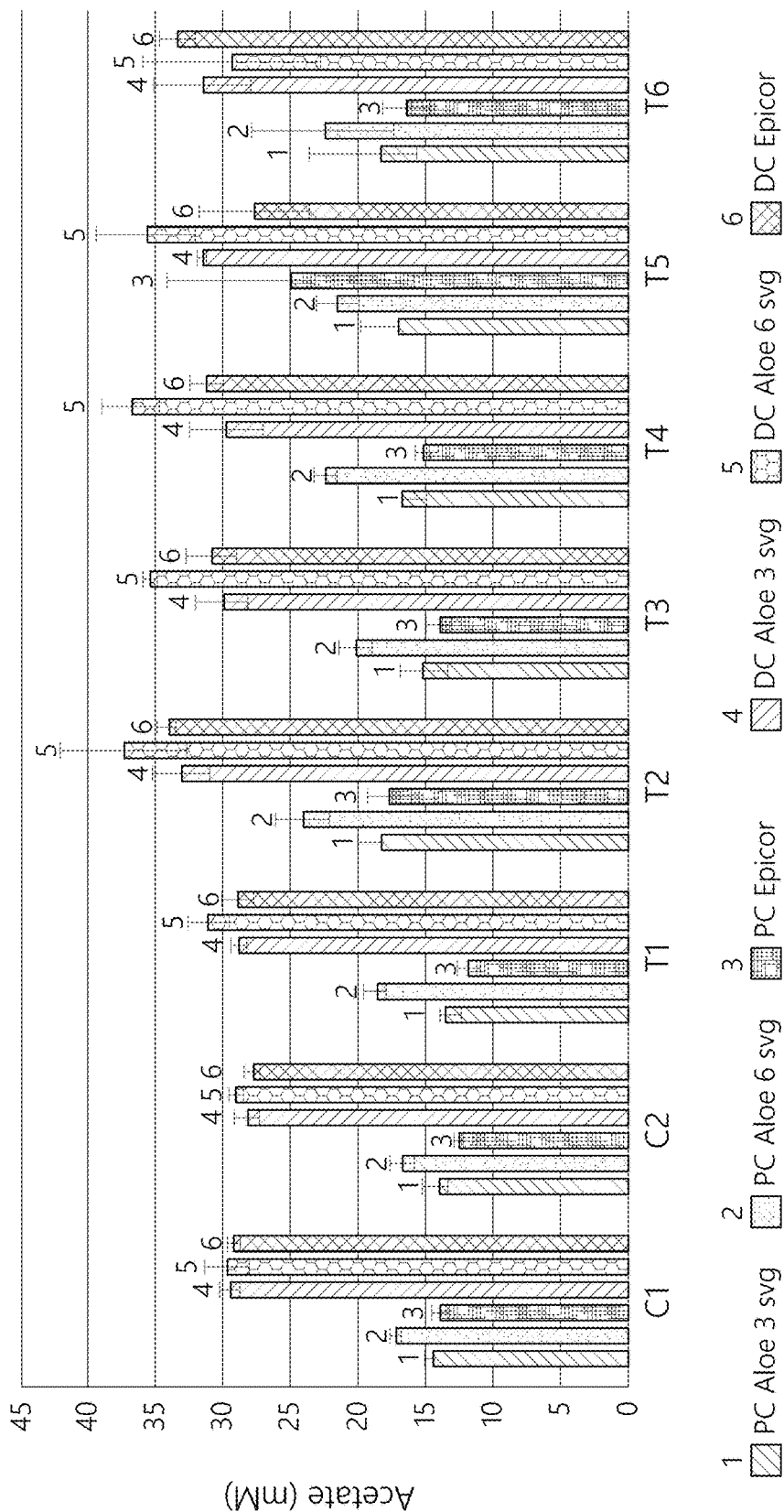
FIG. 5 shows the concentrations (mmol/L) of acetate in the proximal (PC) and distal (DC) colon of the SHIME treated with the test products. The data are presented per experiment week (average and standard dev; n=3). The bars of the bar graph are labeled numerically from 1-6 and correspond with the labels in the legend as shown. The bars on the graph are in in the order of 1) PC Aloe 3 svg; 2) PC Aloe 6 svg; 3) PC Epicor; 4) DC Aloe 3 svg; 5) DC Aloe 6 svg; and 6) DC Epicor.
Figure 6:
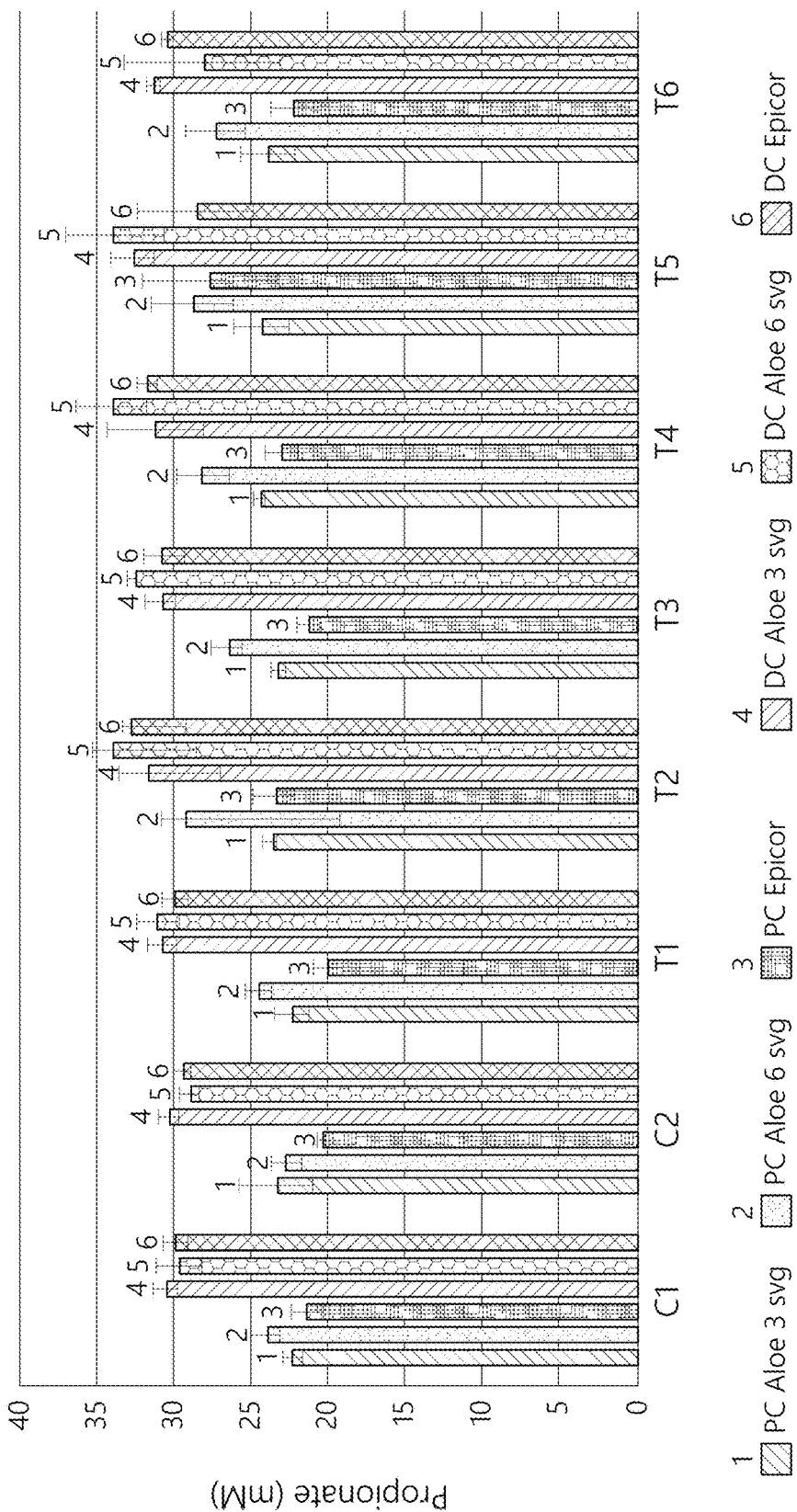
FIG. 6 shows the concentrations (mmol/L) of propionate in the proximal and distal colon of the SHIIVIE treated with the test products. The data are presented per experiment week (average and standard dev; n=3). The bars of the bar graph are labeled numerically from 1-6 and correspond with the labels in the legend as shown. The bars on the graph are in in the order of 1) PC Aloe 3 svg; 2) PC Aloe 6 svg; 3) PC Epicor; 4) DC Aloe 3 svg; 5) DC Aloe 6 svg; and 6) DC Epicor.
Figure 7:
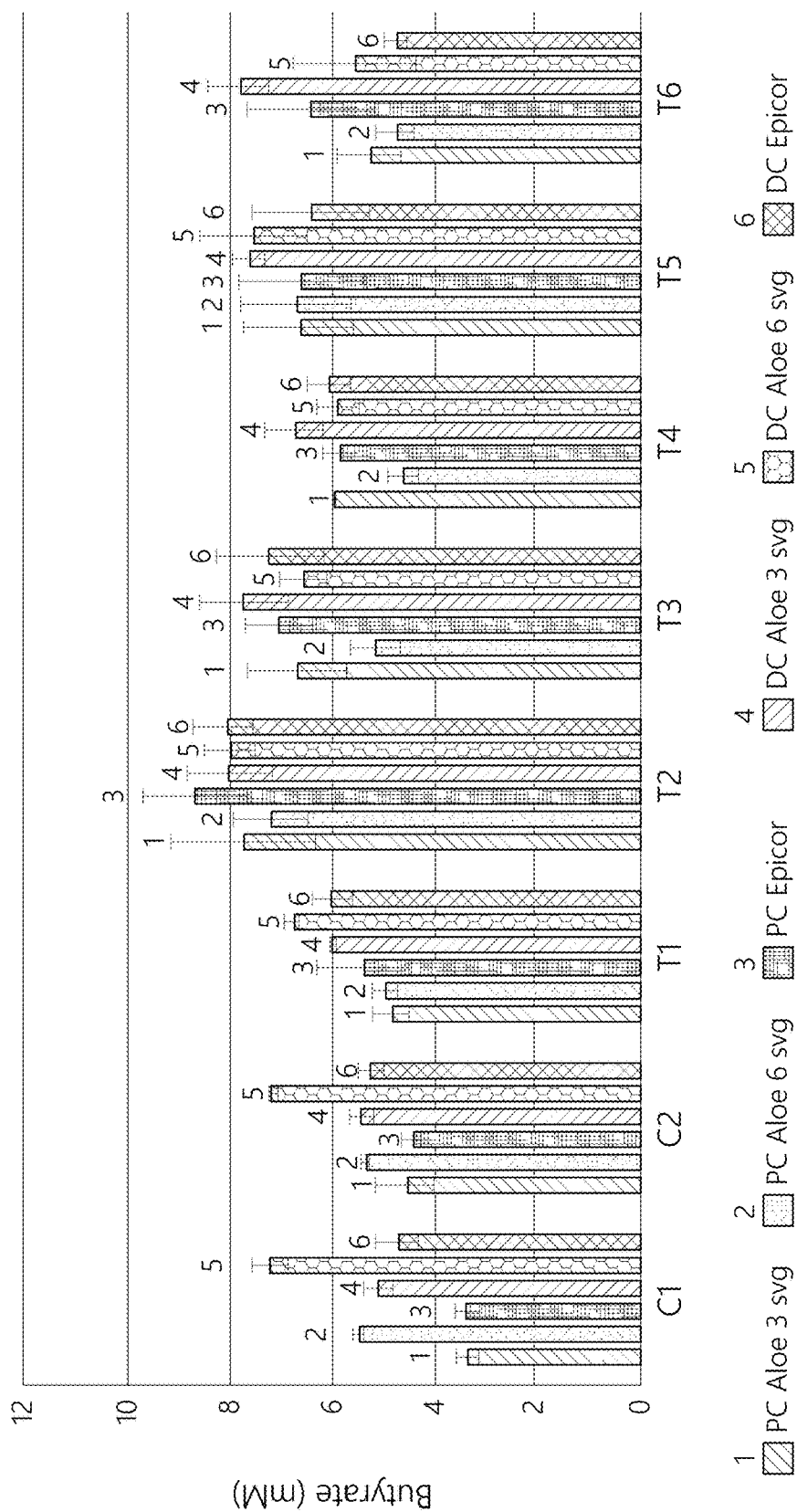
FIG. 7 shows the concentrations (mmol/L) of butyrate in the proximal and distal colon of the SHIIVIE treated with the test products. The data are presented per experiment week (average and standard dev; n=3). The bars of the bar graph are labeled numerically from 1-6 and correspond with the labels in the legend as shown. The bars on the graph are in in the order of 1) PC Aloe 3 svg; 2) PC Aloe 6 svg; 3) PC Epicor; 4) DC Aloe 3 svg; 5) DC Aloe 6 svg; and 6) DC Epicor.
Figure 8:
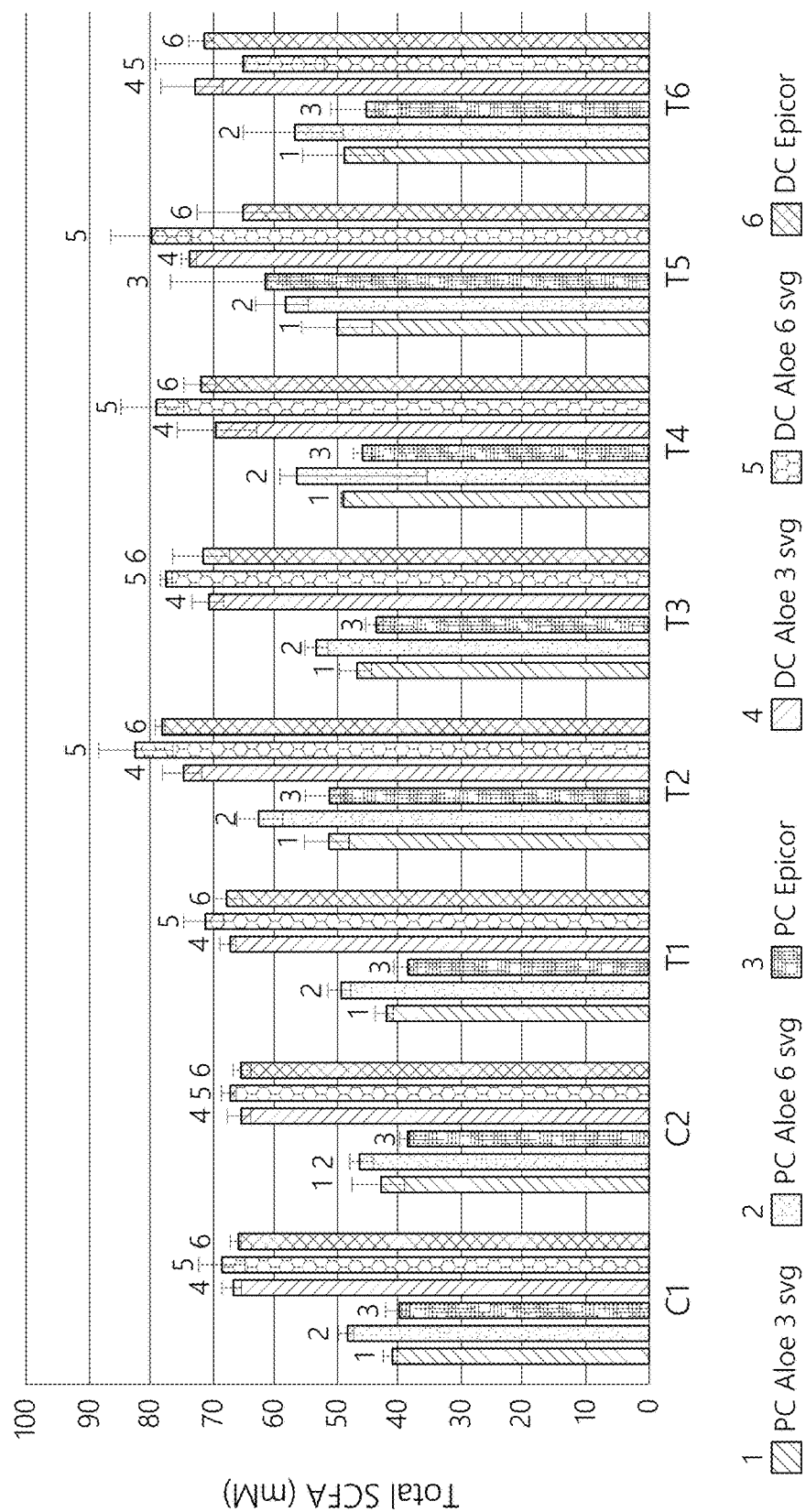
FIG. 8 shows the concentrations (mmol/L) of total SCFA in the proximal and distal colon of the SHIIVIE treated with the test products. The data are presented per experiment week (average and standard dev; n=3). The bars of the bar graph are labeled numerically from 1-6 and correspond with the labels in the legend as shown. The bars on the graph are in in the order of 1) PC Aloe 3 svg; 2) PC Aloe 6 svg; 3) PC Epicor; 4) DC Aloe 3 svg; 5) DC Aloe 6 svg; and 6) DC Epicor.

Samples collected from the different colonic areas of the SHIME systems have been used to evaluate the effect of the test products on the gut inflammation. For instance, FIG. 4 shows a co-culture model.

To set up the system, Caco-2 cells may be grown in semi-permeable inserts until enterocyte-like maturation. After 14 days a functional polarized monolayer may form and the inserts may be then be placed on top of activated THP-1-macrophages. The presence of THP1 may induce damage on the Caco-2 epithelia, thereby affecting barrier integrity (decrease in TEER). Finally, LPS may be added on the basolateral (BL) side to induce inflammation (increase in pro-inflammatory cytokine levels).

This IBD-like model may be used for testing the effect of substances that can protect intestinal epithelial barrier integrity (by inducing an increase in TEER) and can reduce the inflammation (by reducing pro-inflammatory cytokines and increasing anti-inflammatory cytokines). The tests may be conducted by bringing in contact the SHIME suspension with the cell layer. The unique aspect of this approach resides in the fact that it is possible to evaluate the effect induced by the product and its metabolites that are produced by the gut microbiota during the digestive steps (and not only the pure product alone). Tests performed may include:

Trans Epithelial Electric Resistance (TEER) measurements as an indication of the enterocyte monolayer membrane integrity and decreased permeability.

Evaluation of the Lucyfer yellow permeation in the BL compartment as an indication of the monolayer permeability.

Measurement of cytokines production in the BL compartment (IL-8, IL-6, TGF-$\beta$, IL-10) and NF-$\kappa$B activity following the contact with the SHIME suspension.

D. Short Chain Datty Acids (SCFA)

SCFA are the typical end products of mainly saccharolytic fermentation by the intestinal bacteria. SCFA profiles consist mainly of acetate, propionate and butyrate with small amounts of isobutyric, valeric, and isovaleric acid. Whereas acetate can be absorbed from the gut and used as an energy substrate by the host, butyrate acts as a main energy source for the gut epithelium and has proven protective effects against inflammation and colon cancer. Propionate finally, has similar local activity in the gut as compared to butyrate, yet it is also transported to the liver where it was shown to have positive cholesterol-lowering effects and effects on glycemic control. For this reason, butyrate and propionate are considered more health-beneficial for the host as compared to acetate and modulation of the microbial fermentation profiles in the gut towards increased butyrate and/or propionate production is considered beneficial.

E. Lactate Analysis

The human intestine harbors both lactate-producing and lactate-utilizing bacteria. Lactate is produced by lactic acid bacteria and decreases the pH of the environment acting also as an antimicrobial agent. It can also be rapidly converted to acetate, butyrate, and propionate by other microorganisms.

Lactate is a metabolic intermediate for the production of other SCFA and therefore its concentration is fluctuating in time. The transient build-up of lactate also depends on the metabolic capabilities of the microbial community in each colon reactor.

F. Online pH Variation

To make sure that optimal environmental conditions are maintained, the pH in a SHIIVIE system is controlled by pH controllers in the following ranges: 5.6-5.9 (PC); 6.5-6.8 (DC). However, upon stabilization of the microbial community in the different reactors (starting from 2 weeks after inoculation), the microbial community can auto-regulate itself and acid-base consumption is normally low.

During a treatment, when bacteria adapt to the test product and produce for instance increased amounts of SCFA, the environment in the reactors may acidify, which results in additional pH control by means of more administration of base to the respective reactors. In this context, the degree of acidification during the experiment can be used as a measure of the intensity of bacterial metabolism.

G. Analysis of the Microbial Community Composition qPCR is a molecular technique, which is based on the amplification of specific bacterial sequences (16S rRNA genes), combined with the quantification of the number of these specific sequences in the microbial ecosystem at different time points. As this technique is not dependent on the (lack of) culturability of the bacteria, data generated with this method offer a more reliable overview on quantitative effects on the microbial community.

H. Effect on the Gut Wall Modulation

1. Gut Barrier Permeability and Inflammation

Figure 16:
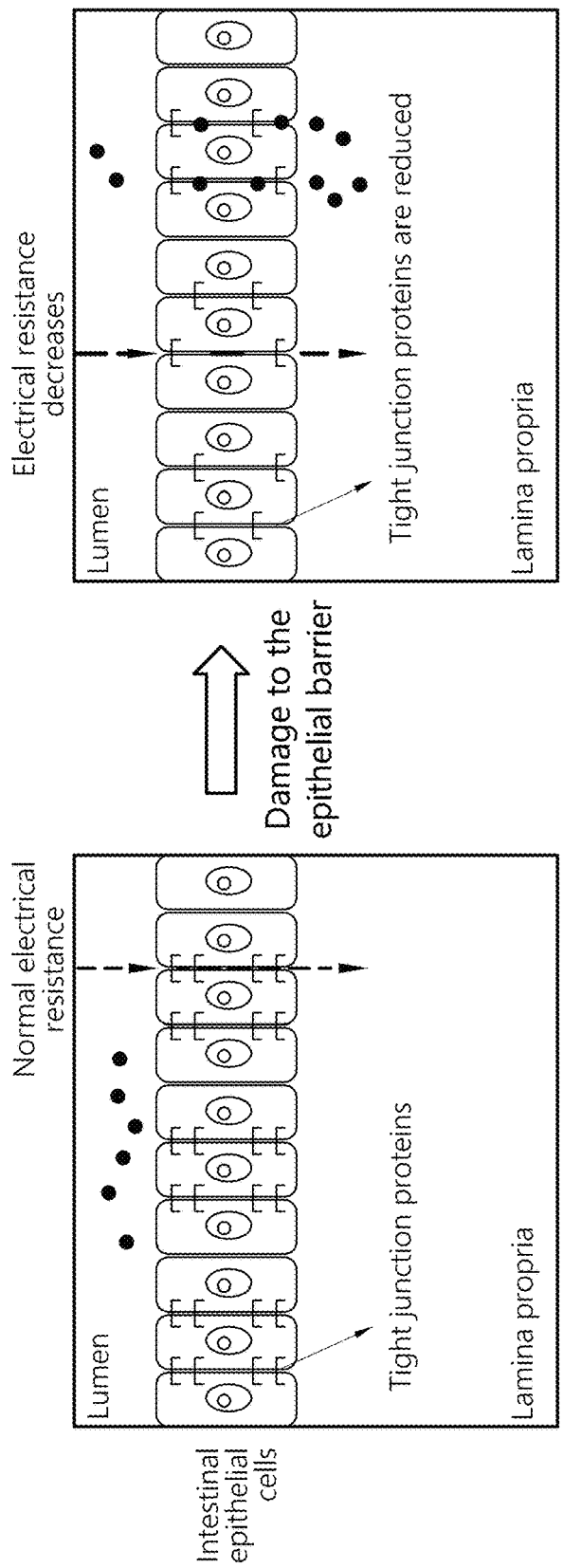
FIG. 16 shows the scheme of the TEER functionality.
Figure 17:
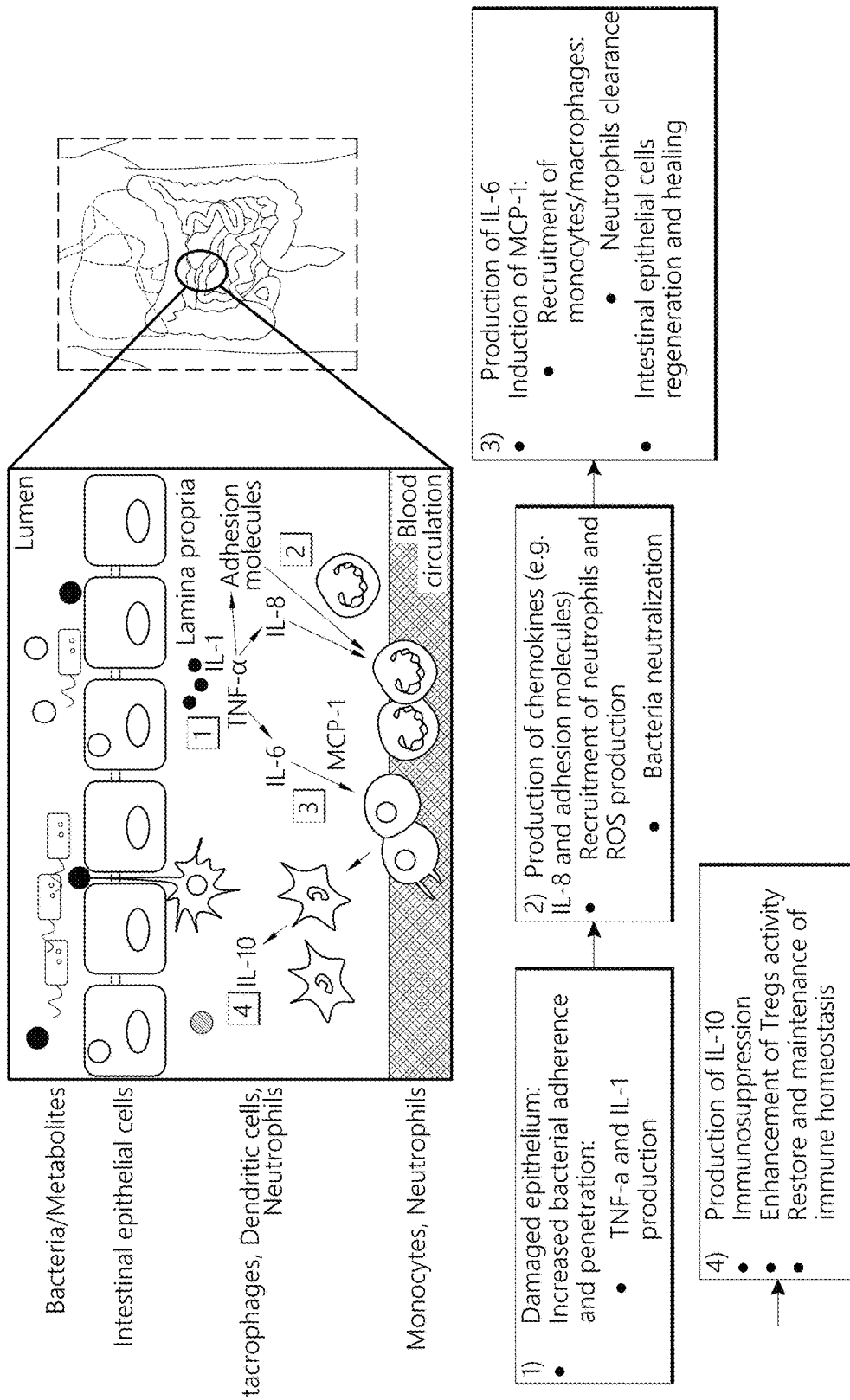
FIG. 17 shows the leaky gut syndrome and the inflammatory cascade.

Samples collected from the different compartments of the SHIME may be brought in contact with a monolayer of Caco-2 cells to evaluate the effect of the test product and its metabolites on gut permeability. This effect is normally evaluated at the level of the tight junctions. The latter are proteins that keep adjacent epithelial cells together, thereby forming a virtually impermeable barrier to fluids. The Trans-epithelial electrical resistance (TEER) allows measuring of the "tightness" of these structures, with high TEER corresponding to a tighter barrier. When damage occurs, these proteins are altered and barrier function is lost. In this case, the TEER is reduced and paracellular transport (between cells) of fluids may increase, as shown in FIG. 16. Moreover, the effect on the gut barrier permeability MAY be observed by analyzing the paracellular transport of lucifer yellow (LY). Chemical, mechanical or pathogen-triggered barrier disruption may lead to influx of bacteria from the lumen into the lamina propria, as shown in FIG. 17. This will activate the immune system, which will switch from a physiological "tolerogenic" inflammation into a detrimental pathological inflammation.

An inflammatory signaling cascade will initiate with the production of alarm molecules such as pro-inflammatory cytokines (e.g. TNF-$\alpha$ and IL-1). These will induce the production of chemokines (such as IL-8) and adhesion molecules, which in turn will lead to the recruitment of neutrophils and to the production of reactive oxygen species (ROS). These are necessary to kill the bacteria and to plug possible breaches in the epithelial wall; however, they may also cause tissue disruption and lead to inflammation.

Therefore, cytokines involved in the resolution of inflammation will be activated. Among these are IL-6 and IL-10:

IL-6, through activation of MCP-1, will lead to monocytes/macrophages recruitment that will promote clearance of neutrophils. IL-6 is also able to inhibit the production of pro-inflammatory cytokines such as IL-1. Moreover, IL-6 has a positive effect on the regeneration of the intestinal epithelium and wound healing.

IL-10 is able to suppress several cells from both innate and adaptive immune systems, to induce activation of anti-inflammatory molecules and to enhance T regulatory cell (Tregs) function which will in turn restore immune homeostasis.

Figure 18:
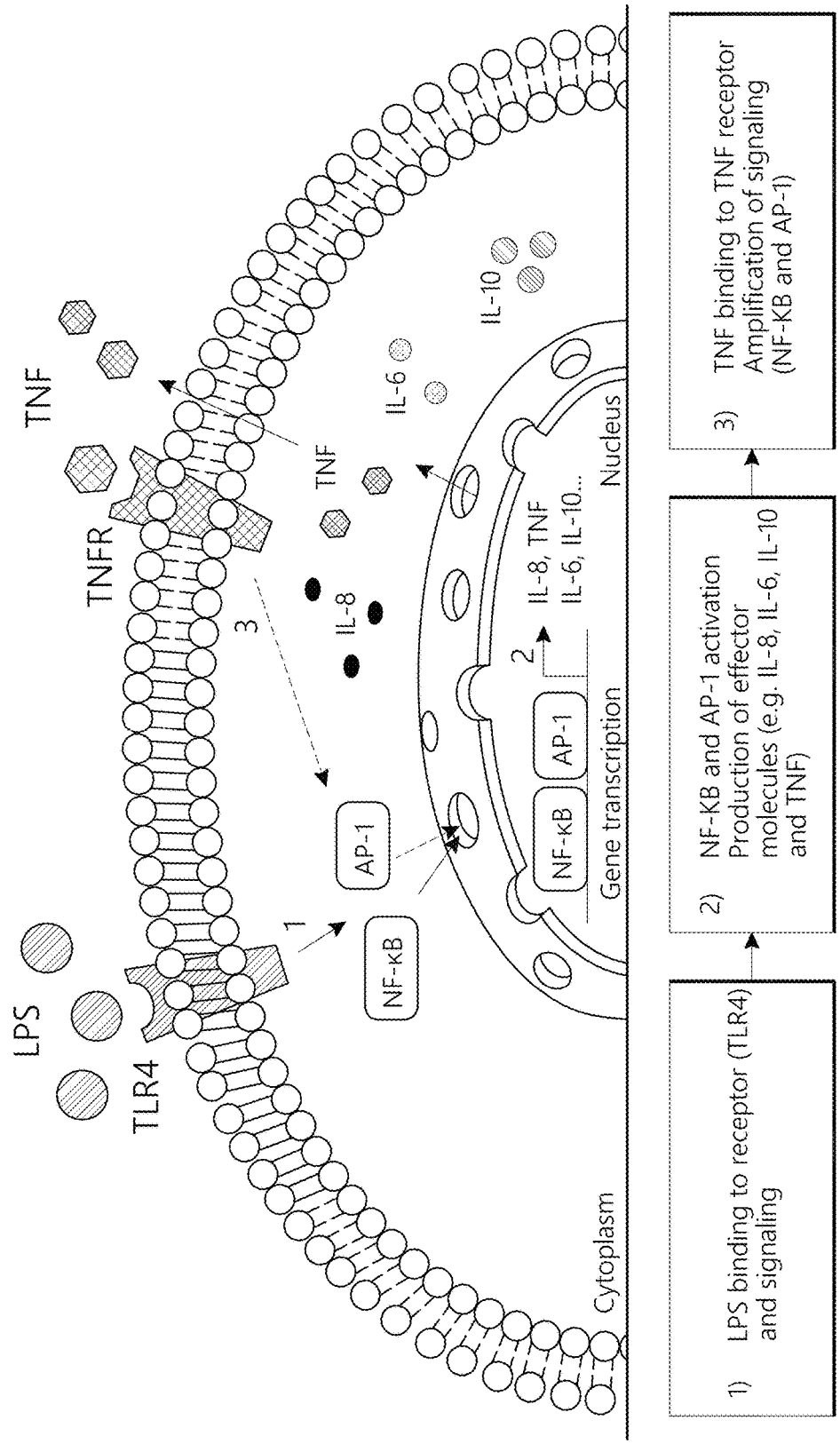
FIG. 18 shows TNF-α cascade of inflammation.

When these switch-off mechanisms are impaired and immune homeostasis cannot be restored, gut pathology can occur and this may result in chronic inflammation. In terms of inflammation, TNF-α is one of the most important and dangerous cytokines produced by the immune system as it is able to amplify inflammation, as shown in FIG. 18.

When not counteracted, TNF-α can lead to chronic inflammation and even death in cases of acute inflammation. For this reason, anti-TNF-α therapy is widely used in several chronic inflammatory conditions such as rheumatoid arthritis, ankylosing spondylitis, inflammatory bowel disease (IBD) and psoriasis. In IBD for example, anti-TNF-α therapy is commonly used to treat chronic inflammation. However, these have several side effects: long-term loss-of-response, higher susceptibility to infections and higher incidence of malignancy (as TNF-α is an anti-tumor molecule).

EXAMPLES

Example 1

To a 2000 gallon mixing tank, 7442.5 kg purified *aloe vera* juice was added. With the mixer on, 7.72 kg sodium benzoate and 7.72 kg potassium sorbate were added into the tank. Flavors were added to the batch. 23.2 kg sodium citrate and about 120-125 kg citric acid were added to have final pH between 2.9-3.4. Water is added to reach the designated volume to the final batch weight. A 2000 gallon finished product was produced. The blend then went through a heat exchanger at 195° F. and was cooled down to ambient temperature before bottling.

Example 2

110 kg purified water was pumped into a 40 gallon stainless steel mixing tank. With mixer on, 0.12 kg sodium benzoate, 0.12 kg potassium sorbate were added into the tank. With continuous mixing, 0.55 kg purified *aloe vera* dry juice powder and 2.66 kg citric acid were added and mixed until completely dissolved. Flavors and sweeteners were then added. 30 gallons of finished product was produced. The blend was then passed through a heat exchanger at 195° F. and cooled to ambient temperature before bottling.

Example 3

To a blender, 66.8 kg maltodextrin, 25 kg sugar, 5.63 kg purified dry aloe juice powder were added and mixed for 5-10 minutes. To a polyethylene bag, 0.53 kg malic acid, 0.25 kg beta carotene, silicon dioxide and flavors were combined and then added to the blender. The mixture was mixed until uniform. 4 g of the powder was mixed with 4-8 fl oz of water.

Example 4

To a v-blender, 383.6 kg cellulose powder, 72.3 kg purified dry *aloe vera* juice powder and 8.05 kg silicon dioxide were added and then mixed for 10 minutes. Then, 5.05 kg magnesium stearate was added into the blender and mixed for additional 4 minutes. The powder was dropped into a storage bin for encapsulation. The powder was encapsulated into "0" hard shell capsule with a targeted fill weight 474 mg (ranging from 450.3 mg to 497.7 mg). The capsule had a disintegration time no more than 30 minutes.

Example 5

To a V-blender, 433.3 kg microcrystalline cellulose, 72.3 kg purified dry *aloe vera* juice powder, 16 kg croscarmellose sodium and 79.8 kg calcium carbonate were added. The mixture was blended for 15 minutes. Then, 6 kg magnesium stearate was added into the blender and the mixture was mixed for an additional 3 minutes. The blended mixture was dropped into a portable container for tableting. The tableting press was operated following the normal procedure. The press was adjusted to have a target tablet weight of 607 mg with range of 576.7 mg to 637.4 mg. The tablet hardness was 6-12 kp with disintegration time no more than 30 minutes.

Example 6

*Aloe vera* whole leaf juice or *Aloe vera* dry whole leaf juice powder was manufactured as follows: mature leafs were harvested and transported to a processing plant within 24 hours of harvest. Leaves were washed and sanitized with chlorinated water. The tip and butt of a leaf were mechanically removed. The rest of leaf went through a grinder and then into a processing tank. At ambient temperature to 60° C., 0 to 500 g of enzyme was added into the tank. After removing cellulose material, the temperature of the juice was raised to 95° C. The juice was passed through an activated charcoal column to remove aloin to no more than 0.1 ppm. The juice could have been used as-is. However, it was further concentrated via vacuum evaporation to *aloe vera* juice concentrate. Alternatively, the juice could have been further processed to *aloe vera* dry juice powder by spray dry, freeze dry or refractance Window drying.

Example 7

*Aloe vera* inner leaf juice or *Aloe vera* dry inner leaf juice powder was manufactured as follows: mature leafs were harvested and transported to a processing plant within 24 hours of harvest. Leaves were washed and sanitized with chlorinated water. The tip, butt and outer skin of a leaf were mechanically removed. The fillet of leaf went through a grinder and then into a processing tank. At ambient temperature to 60° C., 0 to 100 g of enzyme was added into the tank. After removing cellulose material, the temperature of the juice was raised to 85° C. The juice was passed through a resin column to remove aloin to no more than 0.1 ppm. The juice could have been used as-is. However, it was further processed to *aloe vera* dry juice powder by spray drying.

Example 8

Evaluation of the Effect of an Aloe-based Product in the Human Gastrointestinal Tract Using the SHIMS® Technology Platform The purpose of this experiment was to compare:
Epicor (Embria, USA) at 1.5 g/L in the SHIME medium; the positive control that has shown immuno-modulatory/anti-inflammatory effects
Aloe material, 3 servings per day (=0.507 g/L in the SHIME medium), as defined by the batch cultures; and
Aloe material, ideally at 6 servings per day (=1.014 g/L in the SHIME medium), as defined by the batch cultures.

Figure 2:
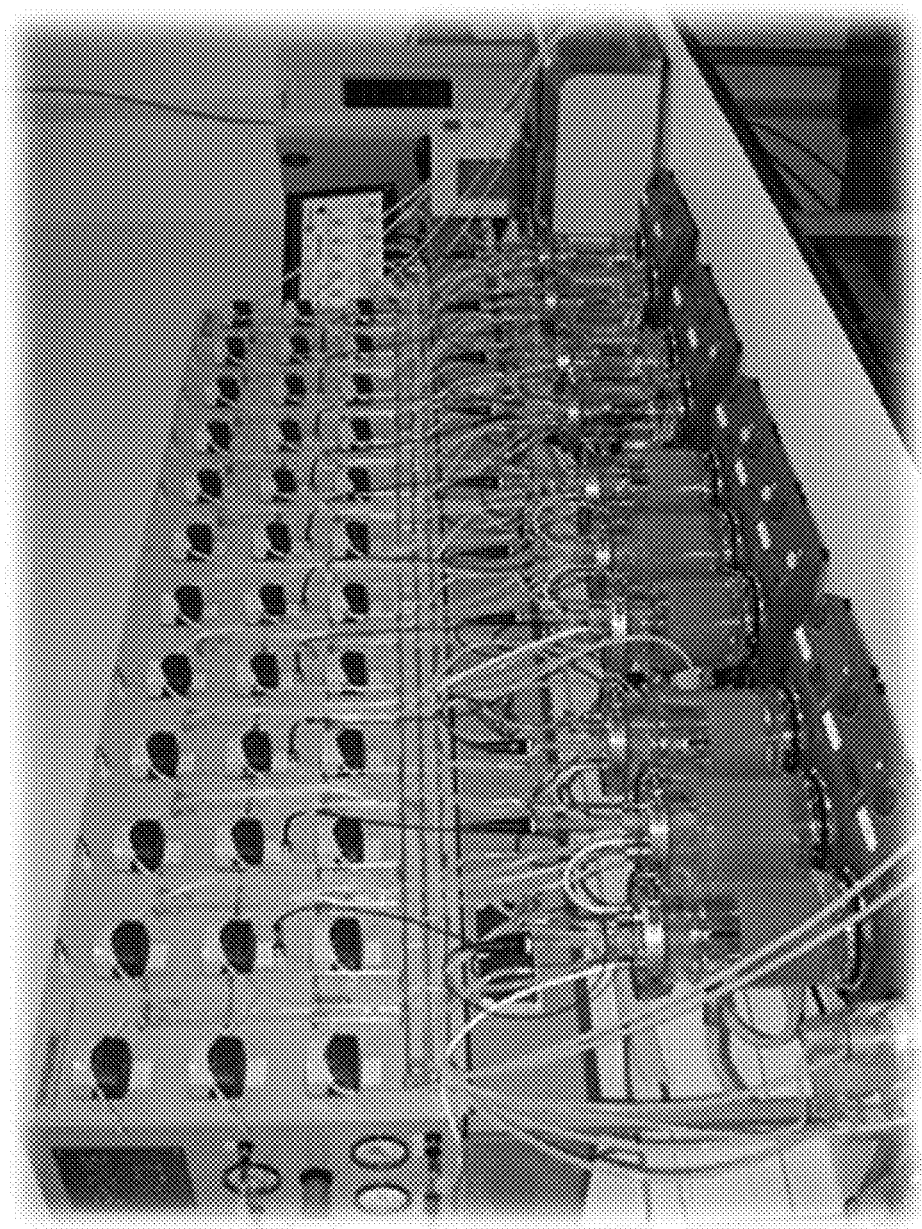
FIG. 2 shows an overview of a TWINSHIME setup, having two parallel SHIME systems. Each SHIME reactor contains 5 vessels simulating respectively the stomach, small intestine, ascending colon, transverse colon and descending colon.
Figure 3:
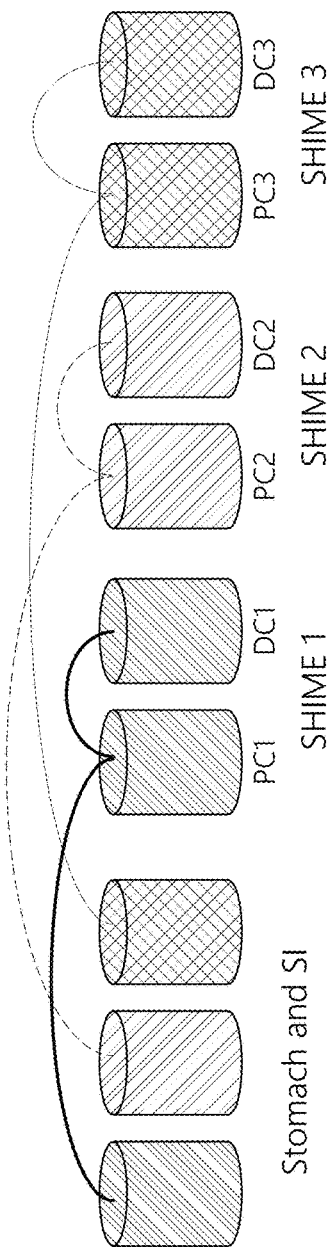
FIG. 3 shows a design of a TripleSHIME in which the normal setup of a TWINSHIME is modified in 3 proximal colons (PC) and 3 distal colons (DC) in order to compare 3 different arms in a single device.

A TWINSHIME, as shown in FIG. 2, was modified into a TripleSHIME for use in this experiment. In a TripleSHIME, the 6 colon compartments acted as a series of PC-DC, PC-DC and PC-DC (PC=proximal colon; DC=distal colon) in place of the classical series of ascending, transverse and descending colon, as shown in FIG. 3.

This SHIME experiment had 3 stages: start-up; control; and treatment. After inoculation of the colon reactors with an appropriate fecal sample (same donor used in the short-term batch experiment), a two-week start-up period allowed the microbial community to differentiate in the different reactors depending on the local environmental conditions. The experiment began during the control period, in which standard SHIME feed was dosed to the model for a period of 14 days. The typical basal medium was composed as follows: Arabinogalactan (1 g/L), Pectin (2 g/L), Xylan (1 g/L), Starch (4.2 g/L), Glucose (0.4 g/L), Yeast extract (3 g/L), Peptone (1 g/L), Mucin (4 g/L), Cysteine (0.5 g/L). Analysis of samples in this period allowed for determination of the baseline microbial community composition and activity in the different reactors, which was then used as the control to compare with the results from the treatment. In the experimental period, the SHIME reactor was operated under nominal conditions, but with a modified diet supplemented with the test products each day. Considering the low dosage of each serving, the SHIME treatment was provided for 6 weeks to maximize the chance of obtaining a clear overview of the effect of the product in the gastrointestinal tract.

FIG. 5, FIG. 6, FIG. 7, and FIG. 8 show the acetate, propionate, butyrate and total SCFA production per experiment week of the different SHIME compartments.

A Trans Epithelial Electric Resistance (TEER) measurement test was performed as an indication of the enterocyte monolayer membrane integrity and decreased permeability.

An evaluation of the Lucyfer yellow permeation in the BL compartment is an indication of the monolayer permeability. A measurement of cytokines production in the BL compartment (IL-8, IL-6, TGF-β, IL-10) and NF-κB activity following the contact with the SHIME suspension was evaluated.

Figure 22:
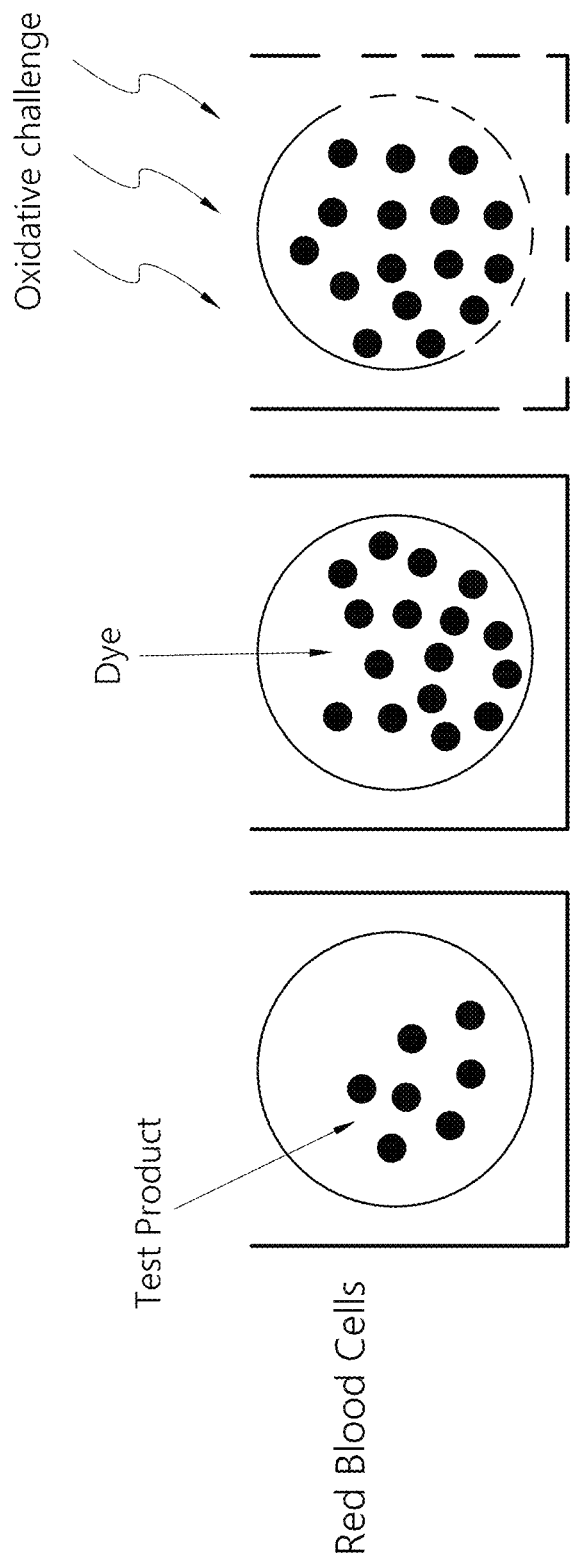
FIG. 22 is a diagram showing the cell-based antioxidant protection assay.

The data was compared by means of a T-test analyses, as shown in FIG. 22, to assess changes between control and treatment periods. Considering the possible delayed effect of the treatments due to the low dosages of the test products, the statistical comparison was performed between the control and either the full treatment period or the last 5, 4 or 3 weeks of treatment.

All products led to an increase in total SCFA production, even if this increase was statistically significant only in the PC for 6 servings of Aloe and in the distal colon for both 3 and 6 servings of Aloe.

The aloe product led to a higher acetate production in the proximal colon, with 6 servings having a stronger effect as compared to 3. In contrast, in presence of Epicor, no statistically significant changes were observed in acetate concentrations.

When considering propionate, the only product which led to a statistically significant increase was 6 servings of Aloe in the proximal colon.

Finally, the aloe product and Epicor, were further distinguished by their effects in terms of butyrate. In fact, while 3 servings of Aloe were effective in increasing the concentration of butyrate both in the proximal and in the distal colon, Epicor led to a statistically significant effect only in the DC. In contrast with what was observed with 3 servings, 6 servings of Aloe did not show any butyrogenic effect. When looking at the single weeks of treatment in FIG. 5, FIG. 6, FIG. 7, and FIG. 8, it seems that all the products could reach the maximum effect after 2 weeks of treatment and that, therefore, repeated doses of the products are needed to induce these effects.

Figure 9:
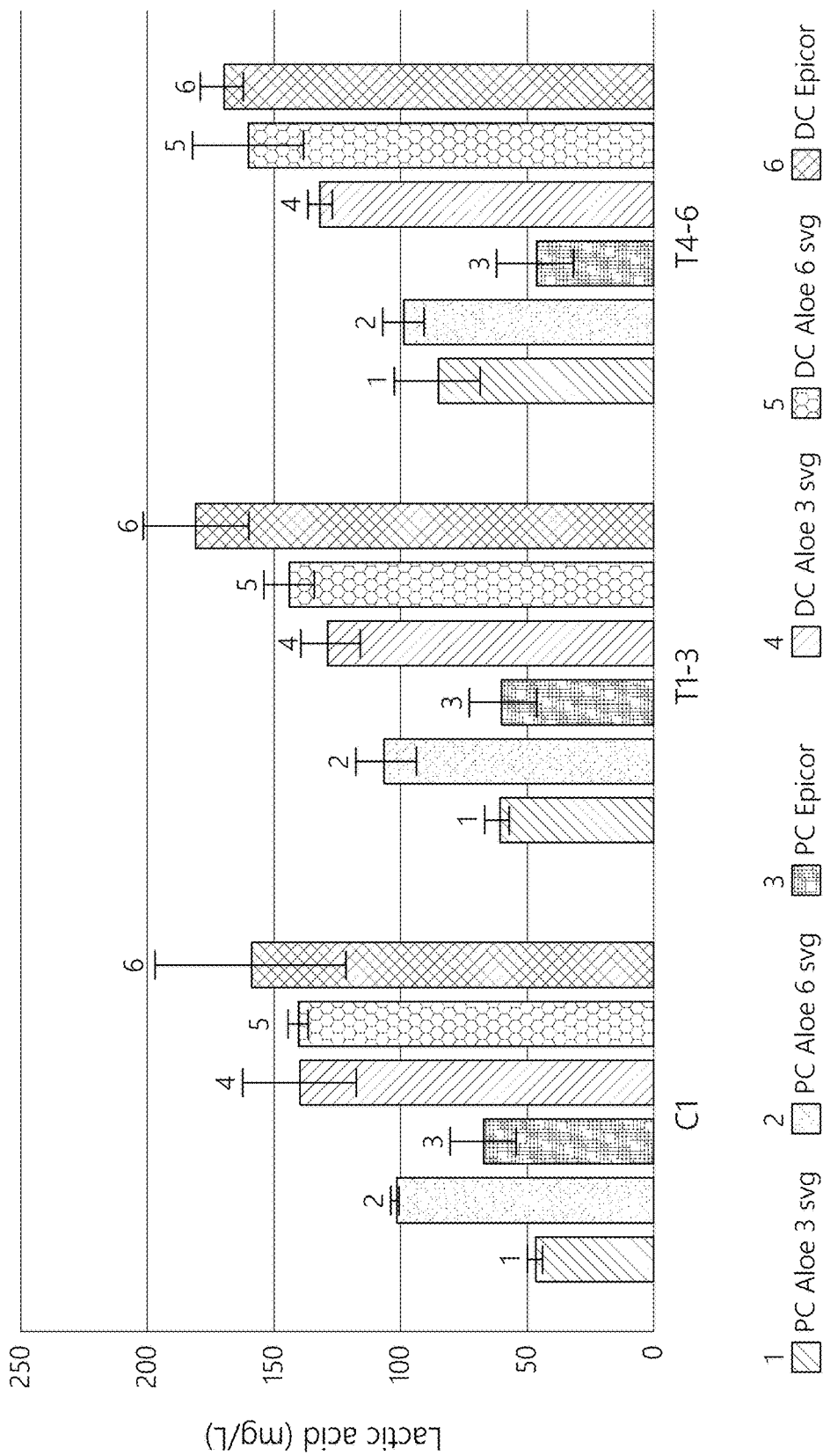
FIG. 9 shows lactate/lactic acid concentration in the proximal colon (PC) and distal colon (DC) of the SHIMEs treated with either the Aloe product or Epicor. The data are presented as average±std dev. of the control period, of the first 3 weeks of treatment and of the last 3 weeks of treatment. No significant differences in lactate production (CTRL vs TREAT) have been observed (P>0.05). The bars of the bar graph are labeled numerically from 1-6 and correspond with the labels in the legend as shown. The bars on the graph are in in the order of 1) PC Aloe 3 svg; 2) PC Aloe 6 svg; 3) PC Epicor; 4) DC Aloe 3 svg; 5) DC Aloe 6 svg; and 6) DC Epicor.

The analysis of lactate concentrations in the different colon regions throughout the course of the experiment are shown in FIG. 9. The administration of the test products to the TripleSHIME had no mayor impact on the lactate concentration in the different colon compartments.

Figure 10A:
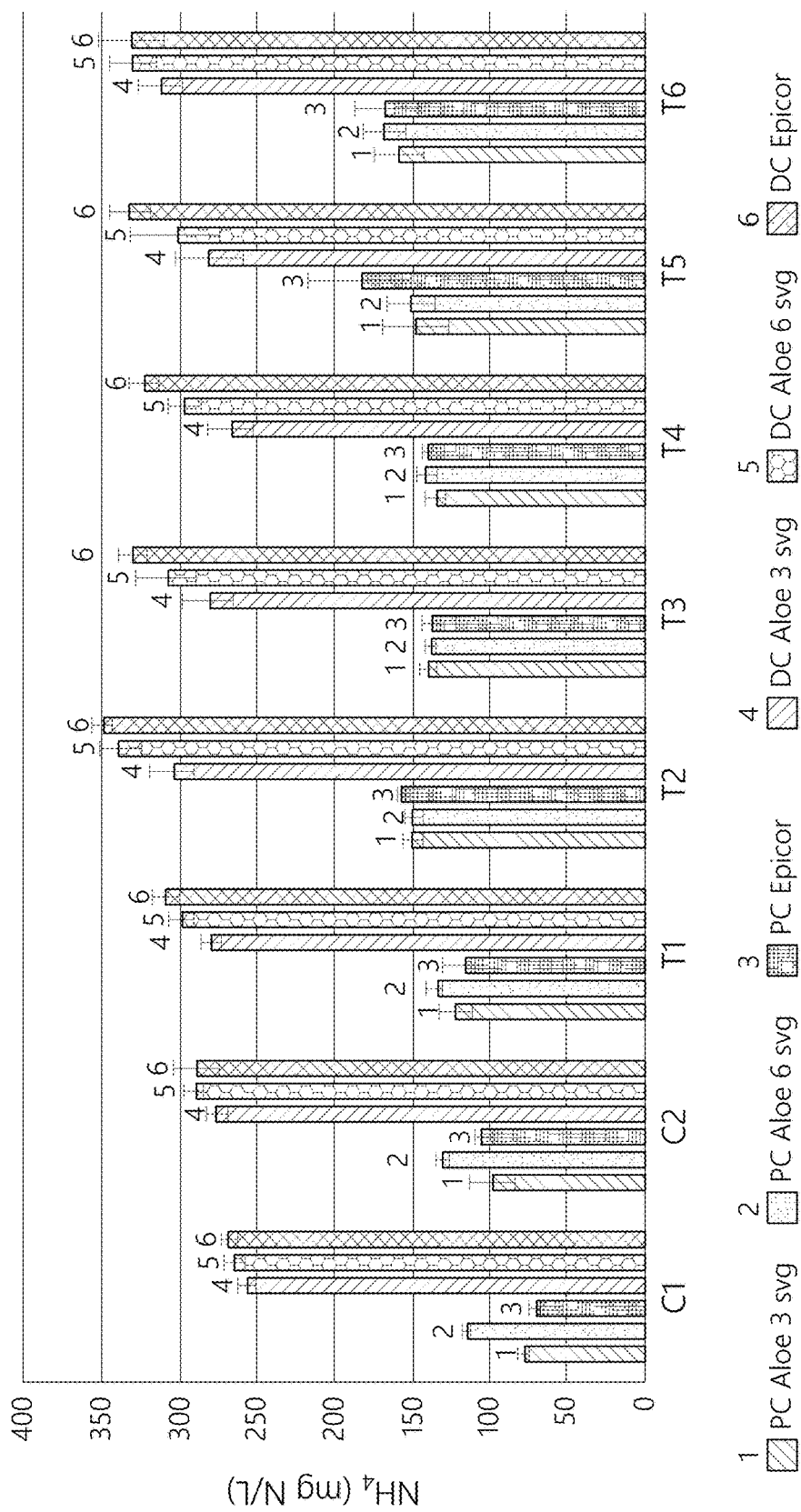
FIG. 10A shows ammonium concentrations (mg $NH_4^+$/L) in the proximal and distal colon of the TripleSHIME. The data are presented per experimental week. Significant differences in ammonium production (CTRL vs TREAT) are indicated with * for P<0.05. The bars of the bar graph are labeled numerically from 1-6 and correspond with the labels in the legend as shown. The bars on the graph are in in the order of 1) PC Aloe 3 svg; 2) PC Aloe 6 svg; 3) PC Epicor; 4) DC Aloe 3 svg; 5) DC Aloe 6 svg; and 6) DC Epicor.
Figure 10B:
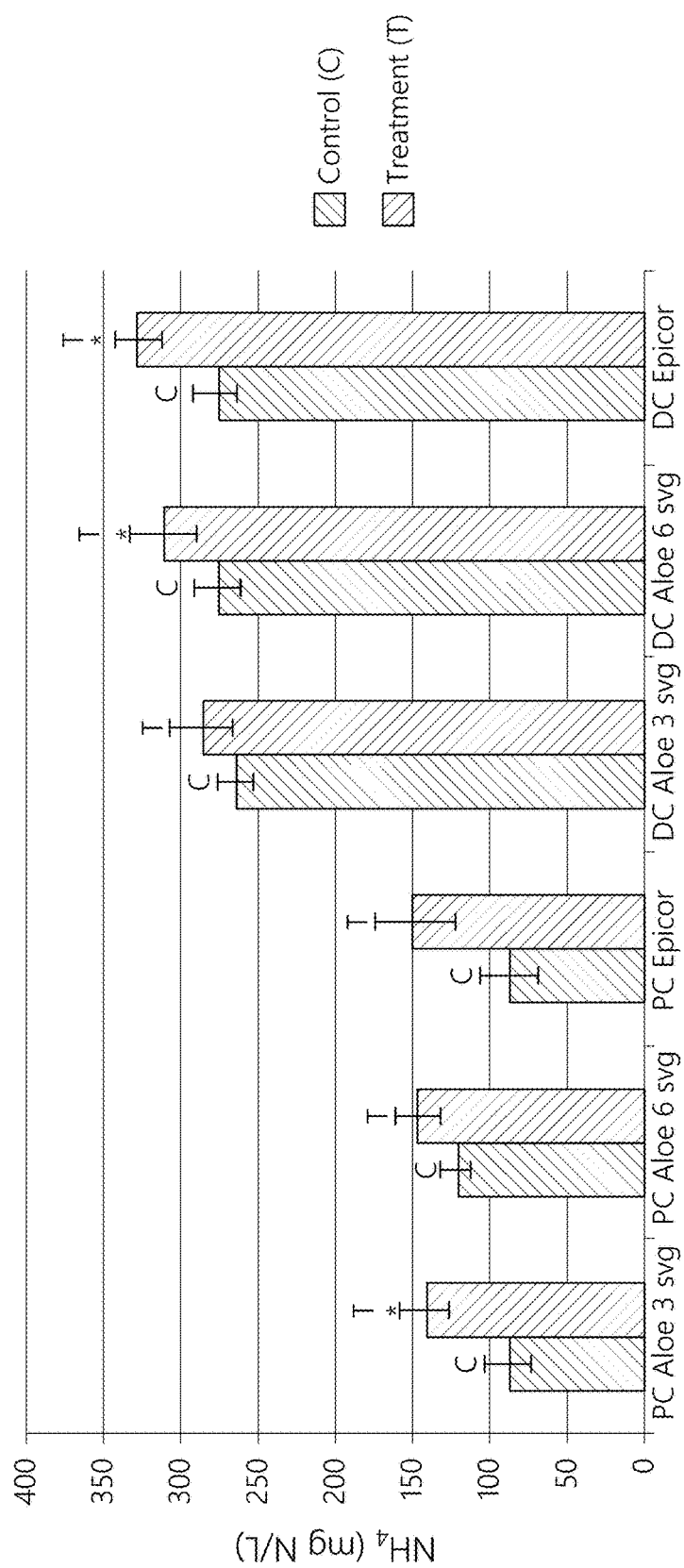
FIG. 10B shows ammonium concentrations (mg $NH_4^+/L$) in the proximal and distal colon of the TripleSHIME. The data are presented per experimental period. Significant differences in ammonium production (CTRL vs TREAT) are indicated with * for P<0.05. Control (C) and Treatment (T) are labeled above the bars in the bar graph.

The analysis of ammonium concentrations in the different simulated colon regions throughout the course of the experiments was shown in FIG. 10A and FIG. 10B, both for the experimental week and for the experimental period (CTRL vs. TREAT).

All the test products led to a similar increasing trend in ammonium production both in the proximal and the distal colon compartments. This increase was statistically significant for 3 servings of Aloe in the PC and for 6 servings of Aloe and Epicor in the DC.

Figure 11A:
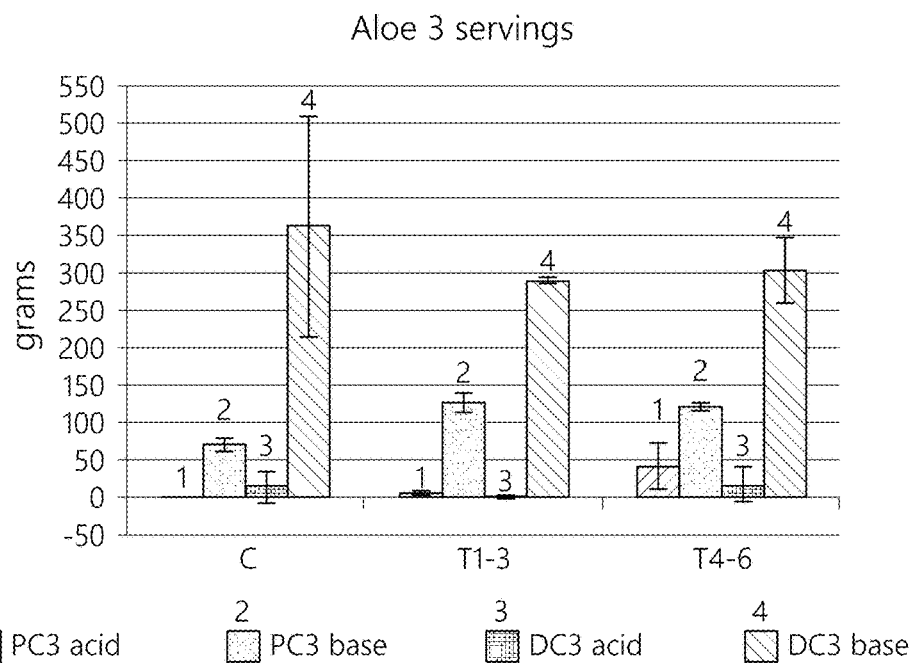
FIG. 11A shows acid-base consumption in the proximal (PC) and distal (DC) colon of the SHIMEs treated with 3 servings of aloe (PC3 or DC3). The data are presented as the average consumption during the control period (C), the first 3 weeks of treatment (T1-3) and the last 3 weeks of treatment (T4-6). As labeled: 1) PC3 acid; 2) PC3 base; 3) DC3 acid; and 4) DC3 base.
Figure 11B:
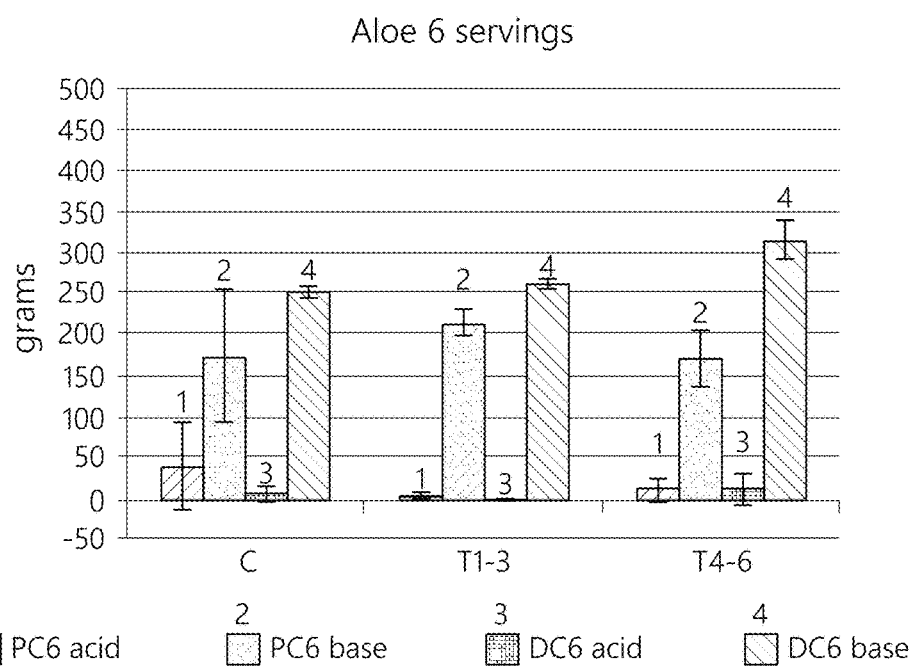
FIG. 11B shows acid-base consumption in the proximal (PC) and distal (DC) colon of the SHIMEs treated with 6 servings of Aloe (PC6 or DC6). The data are presented as the average consumption during the control period (C), the first 3 weeks of treatment (T1-3) and the last 3 weeks of treatment (T4-6). As labeled: 1) PC6 acid; 2) PC6 base; 3) DC6 acid; and 4) DC6 base.
Figure 11C:
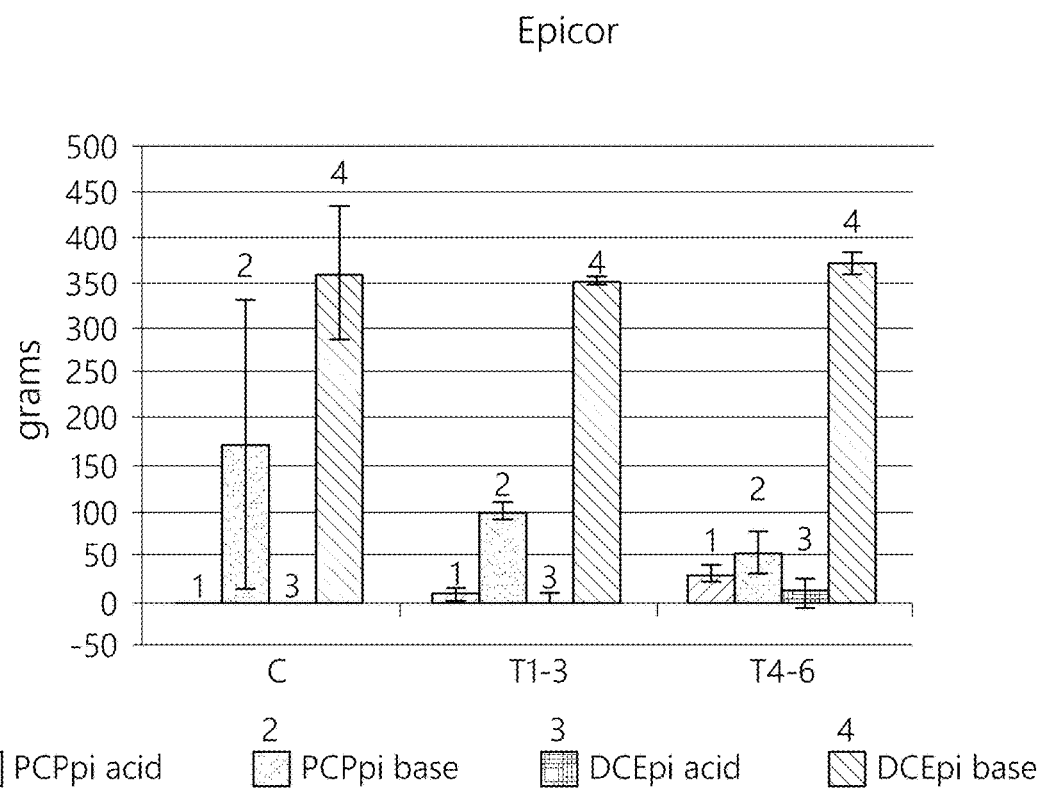
FIG. 11C shows acid-base consumption in the proximal (PC) and distal (DC) colon of the SHIMEs treated with Epicore (PCEpi or DCEpi). The data are presented as the average consumption during the control period (C), the first 3 weeks of treatment (T1-3) and the last 3 weeks of treatment (T4-6). As labeled: 1) PCPpi acid; 2) PCPpi base; 3) DCEpi acid; and 4) DCEpi base.
Figure 12A:
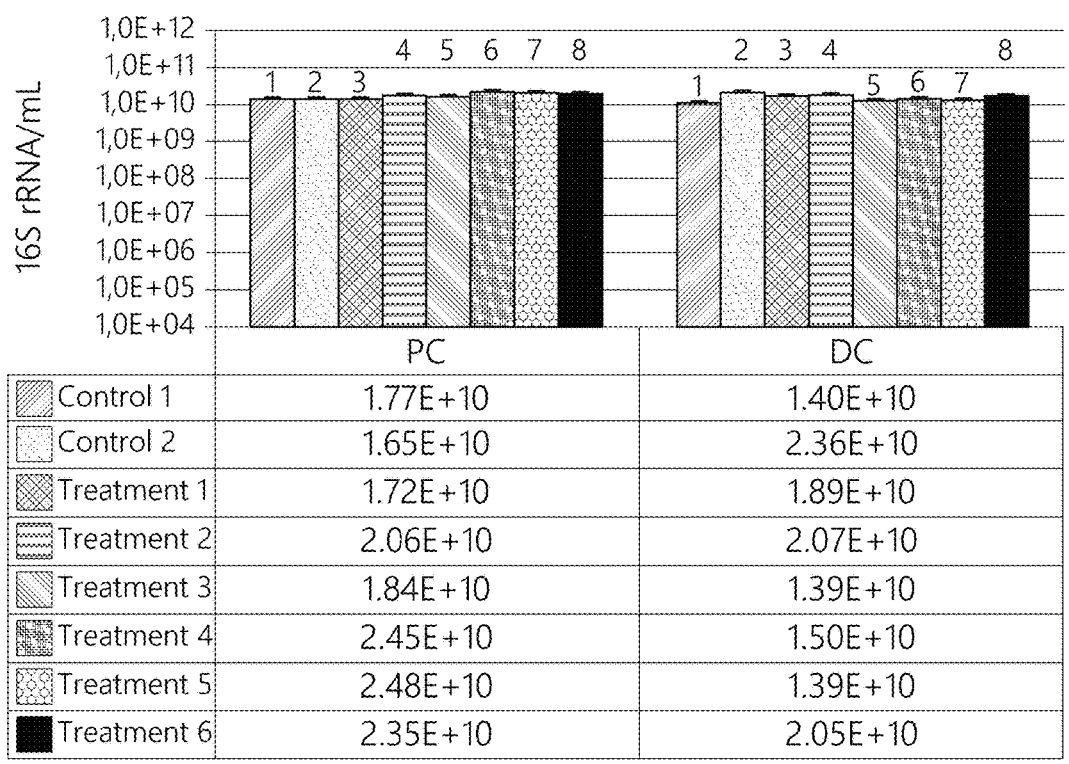
FIG. 12A shows qPCR data for luminal concentration of total bacteria in the arm of the TripleSHIME treated with 3 servings of Aloe. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 12B:
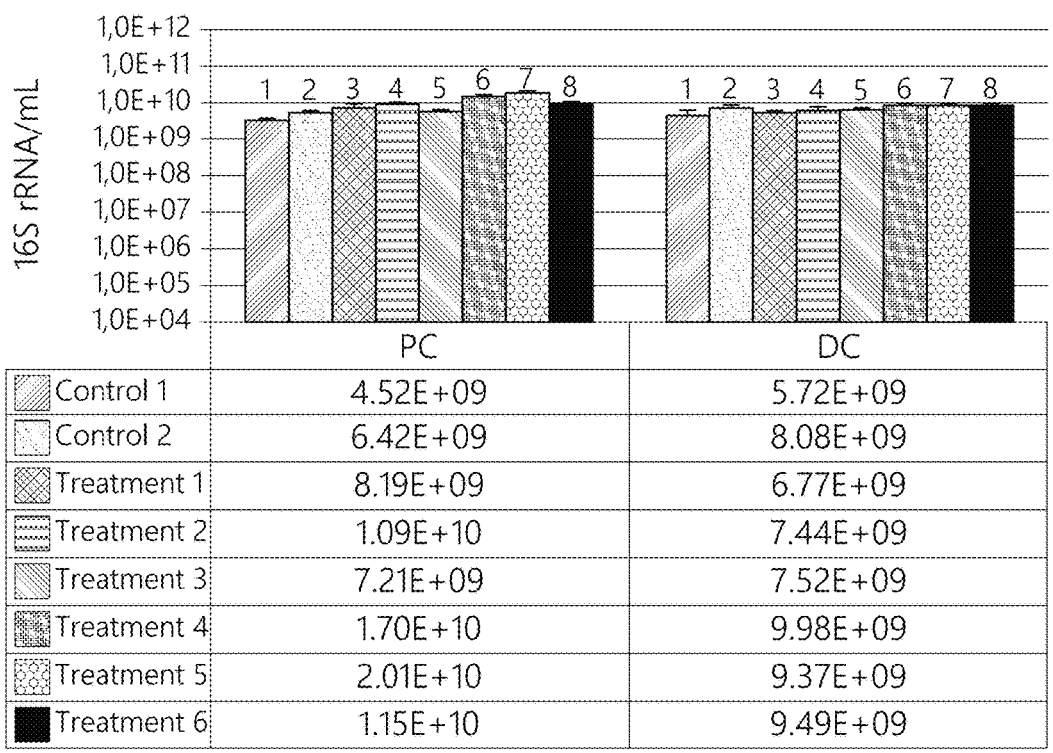
FIG. 12B shows qPCR data for luminal concentration of Bacteroidetes, in the arm of the TripleSHIME treated with 3 servings of Aloe. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 12C:
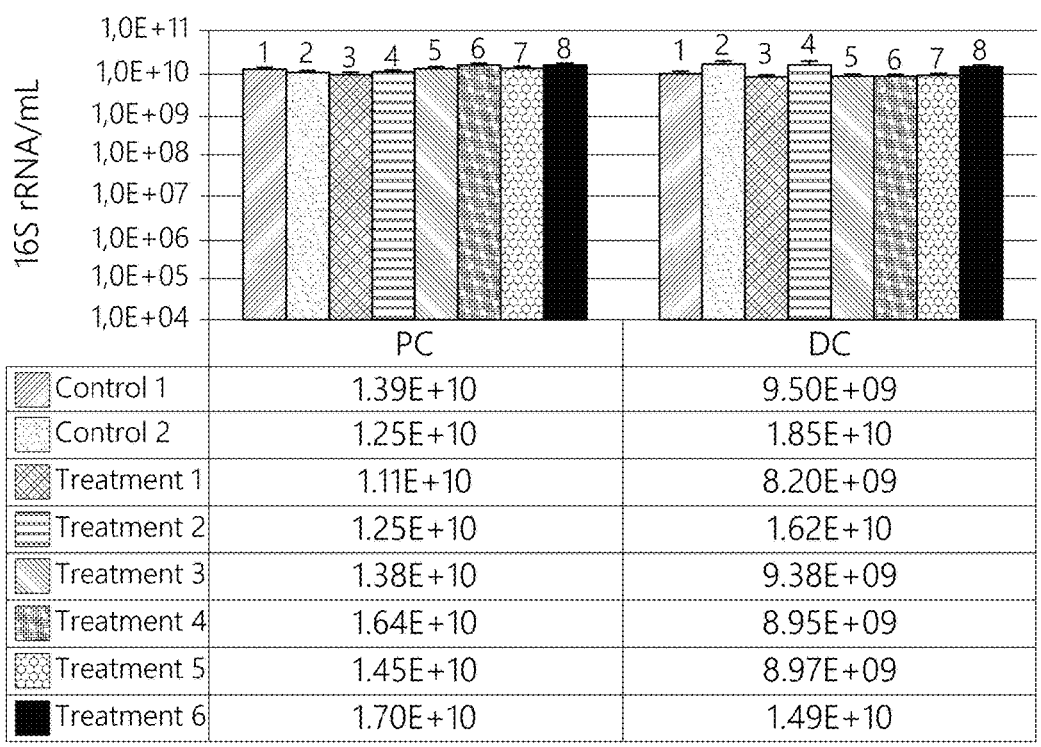
FIG. 12C shows qPCR data for luminal concentration of Firmicutes in the arm of the TripleSHIME treated with 3 servings of Aloe. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 12D:
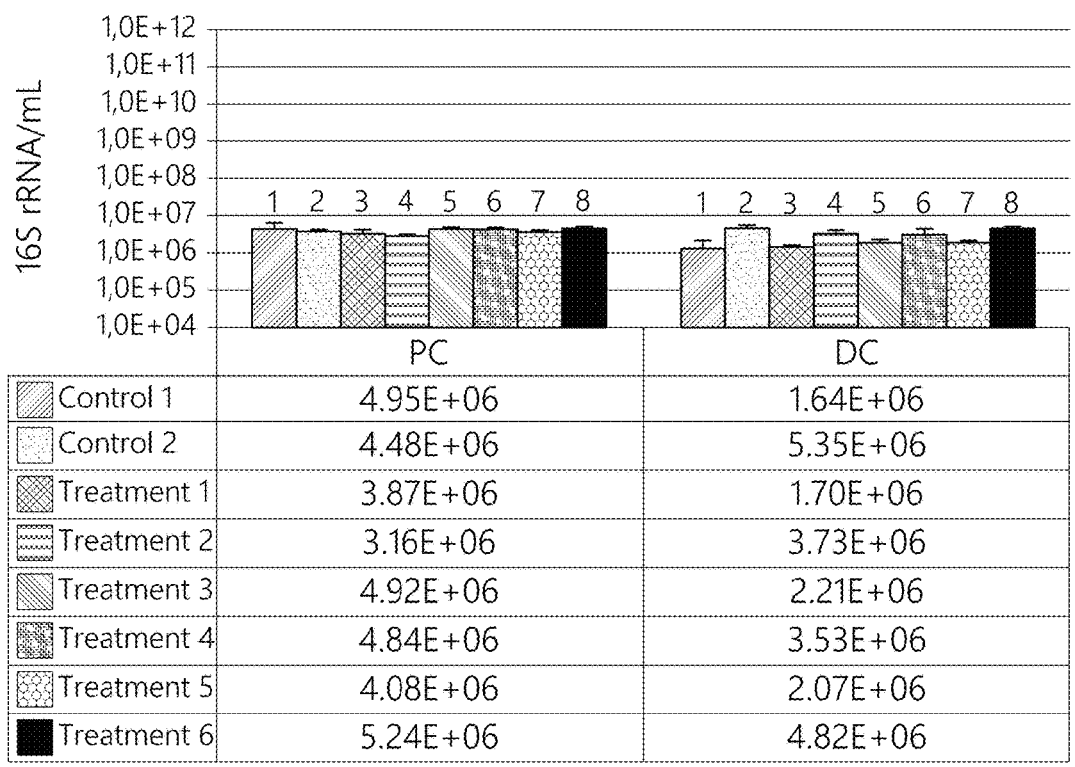
FIG. 12D shows qPCR data for luminal concentration of lactobacilli in the arm of the TripleSHIME treated with 3 servings of Aloe. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 12E:
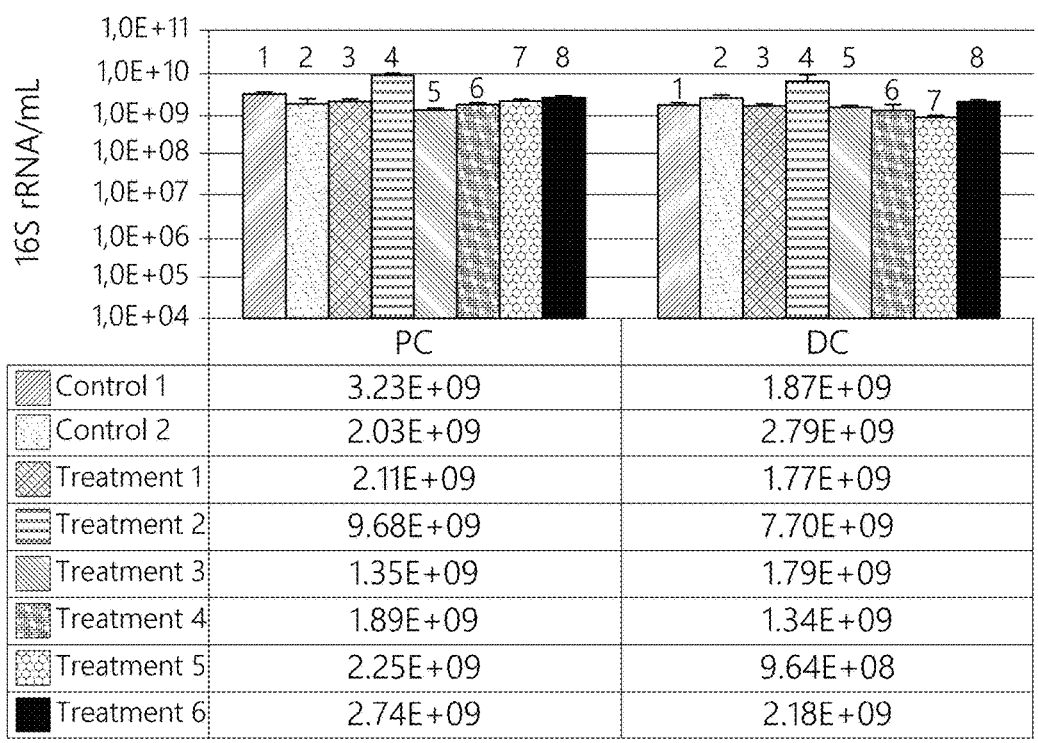
FIG. 12E shows qPCR data for luminal concentration of bifidobacteria in the arm of the TripleSHIME treated with 3 servings of Aloe. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 13A:
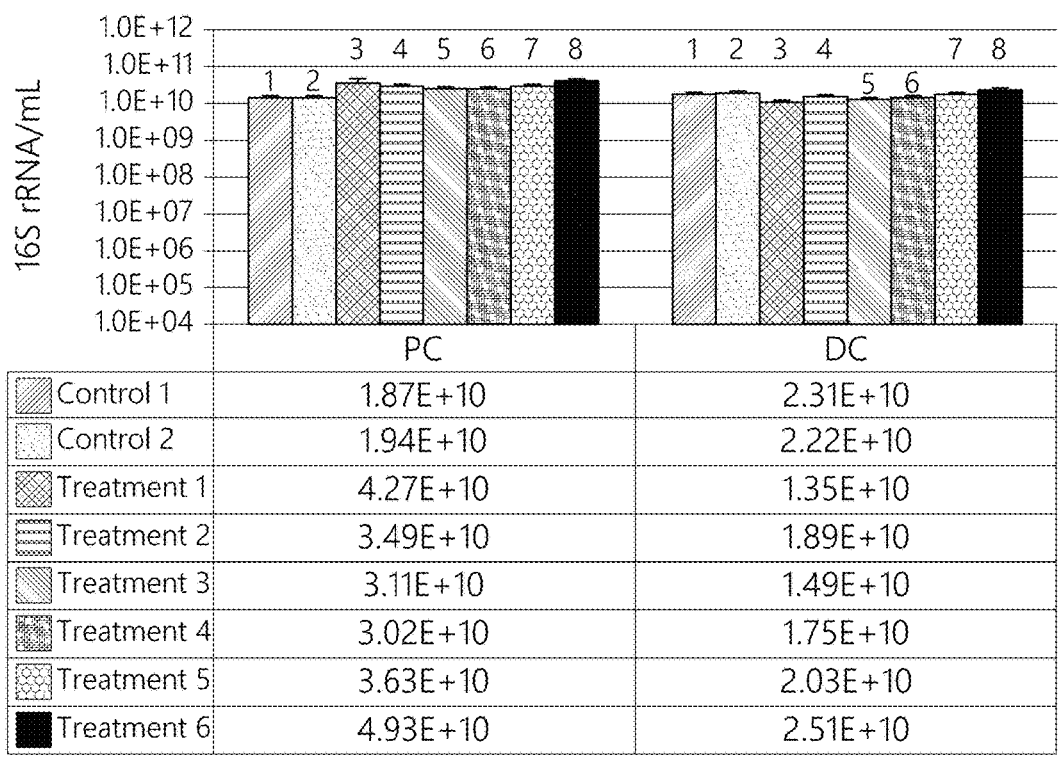
FIG. 13A shows qPCR data for luminal concentration of total bacteria in the arm of the TripleSHIME treated with 6 servings of Aloe. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 13B:
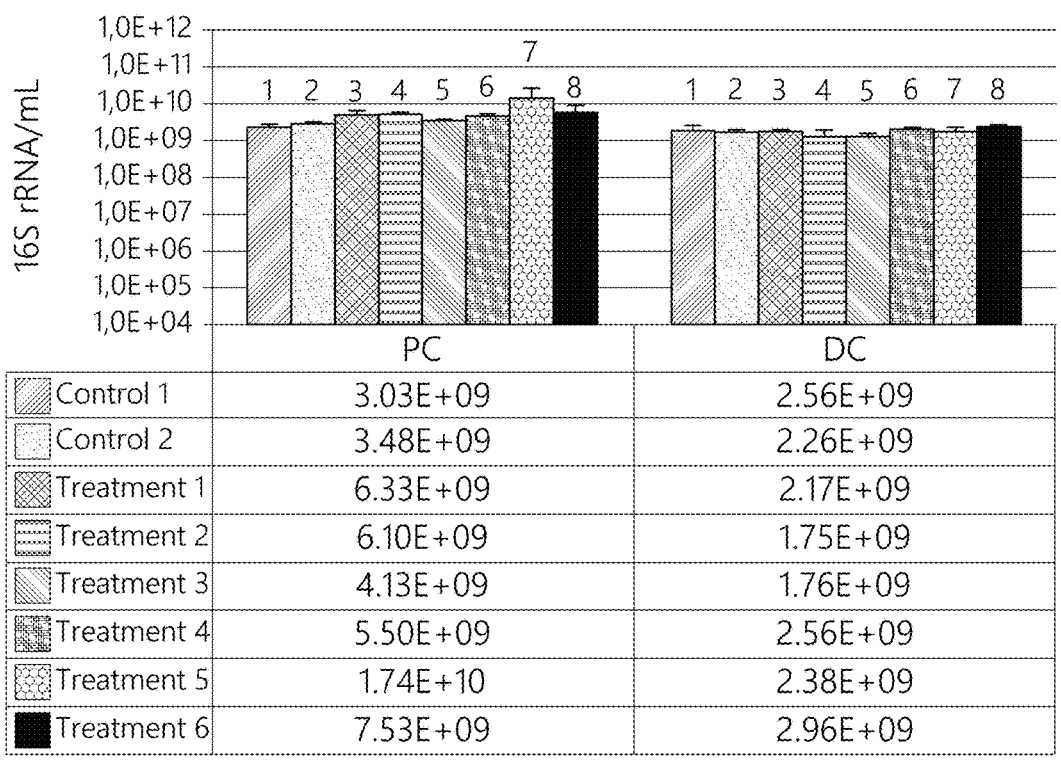
FIG. 13B shows qPCR data for luminal concentration of Bacteroidetes in the arm of the TripleSHIME treated with 6 servings of Aloe. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 13C:
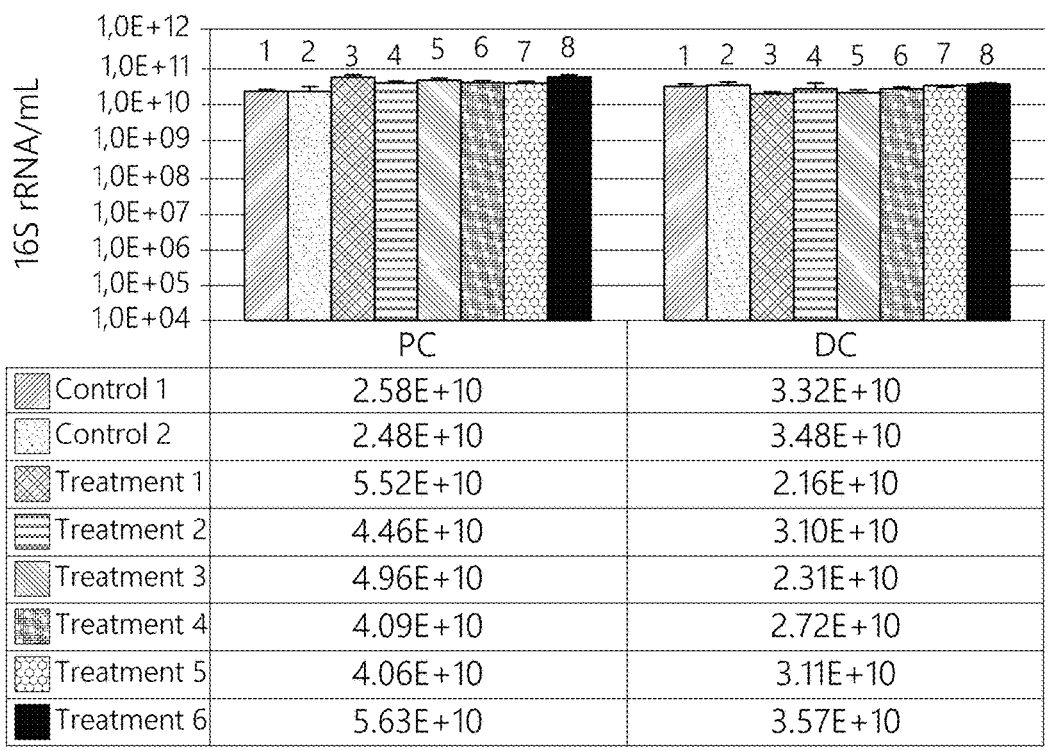
FIG. 13C shows qPCR data for luminal concentration of Firmicutes in the arm of the TripleSHIME treated with 6 servings of Aloe. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 13D:
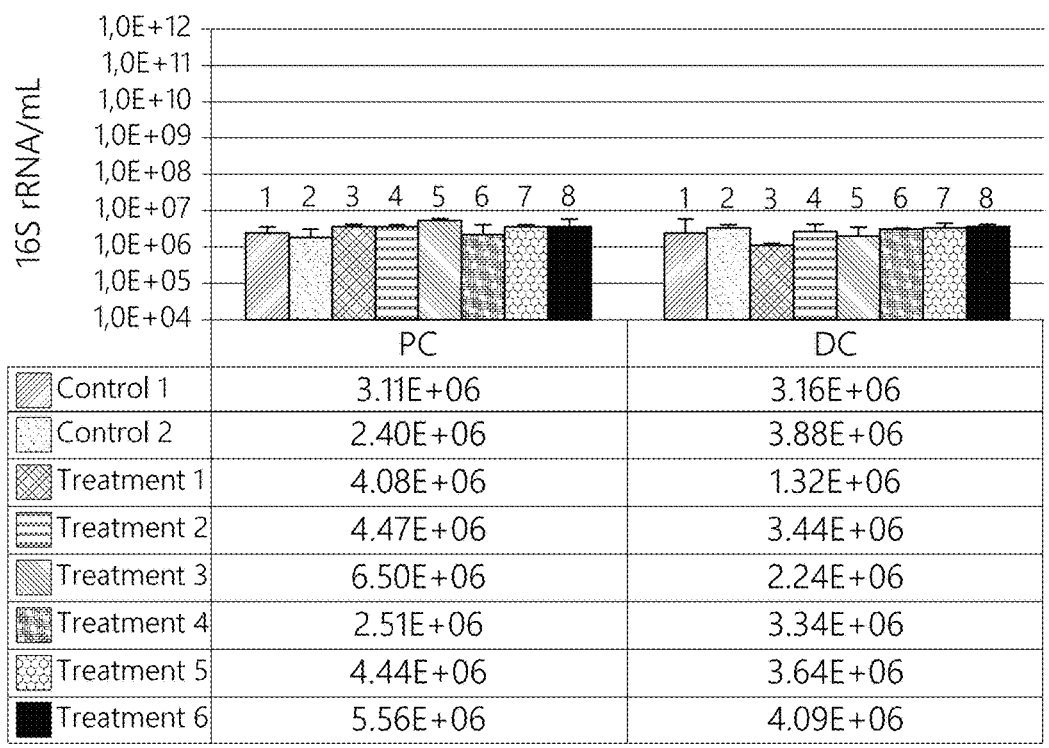
FIG. 13D shows qPCR data for luminal concentration of lactobacilli in the arm of the TripleSHIME treated with 6 servings of Aloe. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 13E:
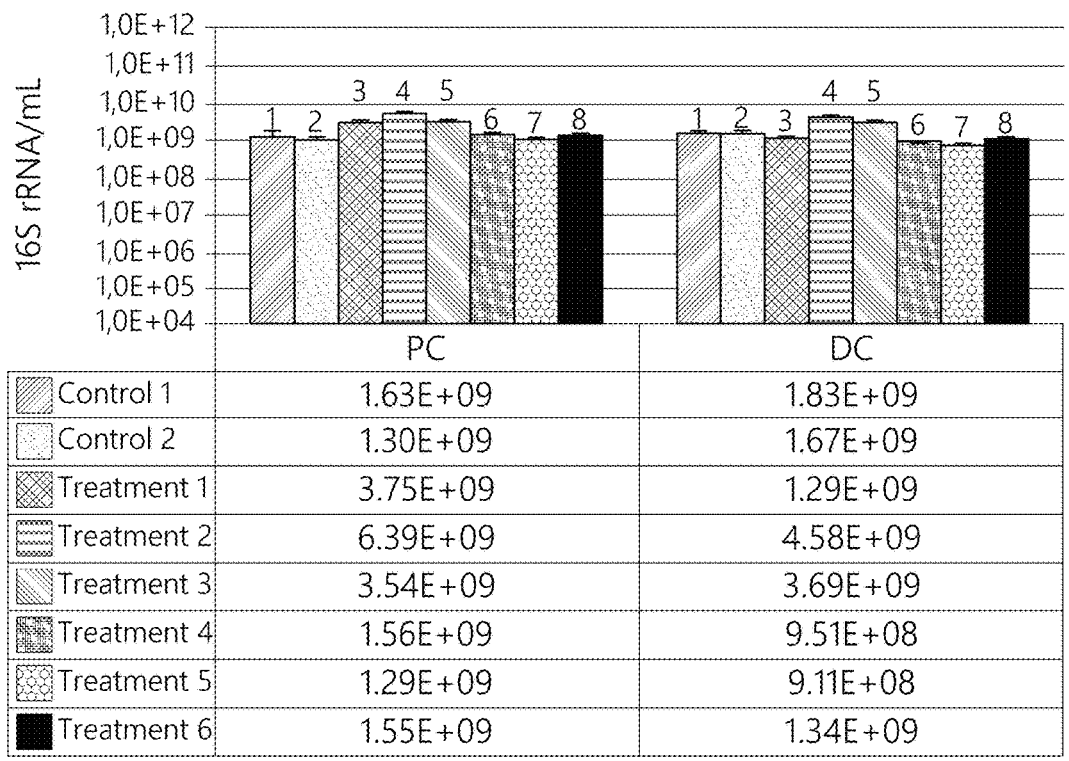
FIG. 13E shows qPCR data for luminal concentration of bifidobacteria in the arm of the TripleSHIME treated with 6 servings of Aloe. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 14A:
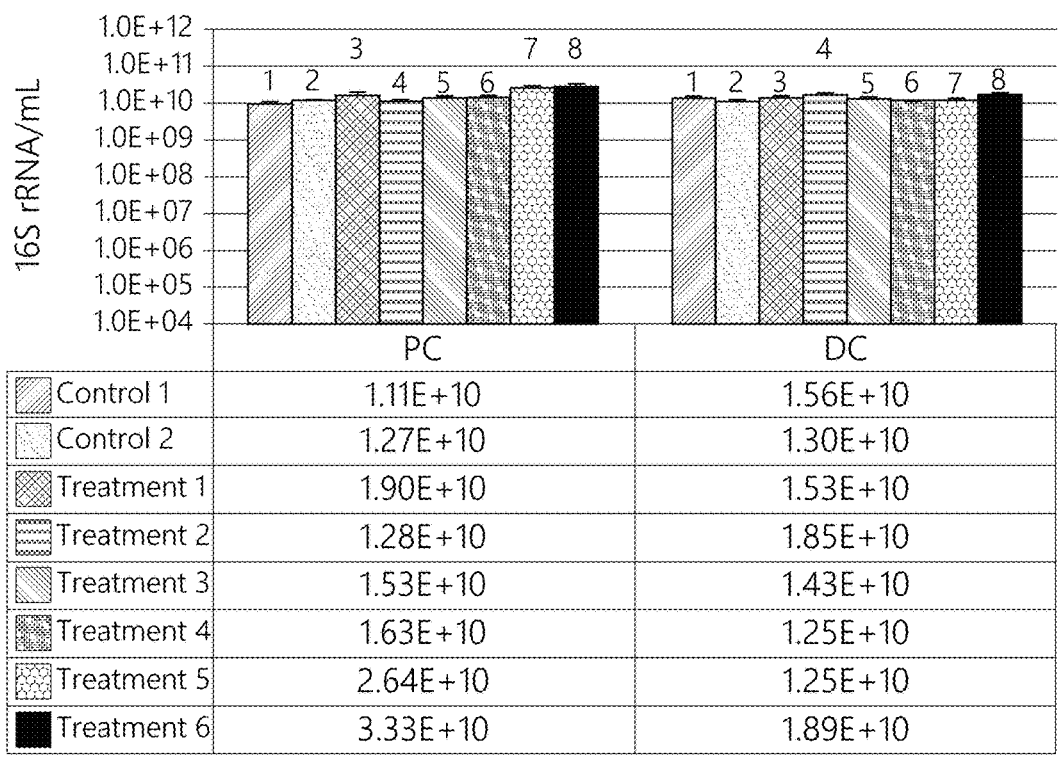
FIG. 14A shows qPCR data for luminal concentration of total bacteria in the arm of the TripleSHIME treated with Epicor. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 14B:
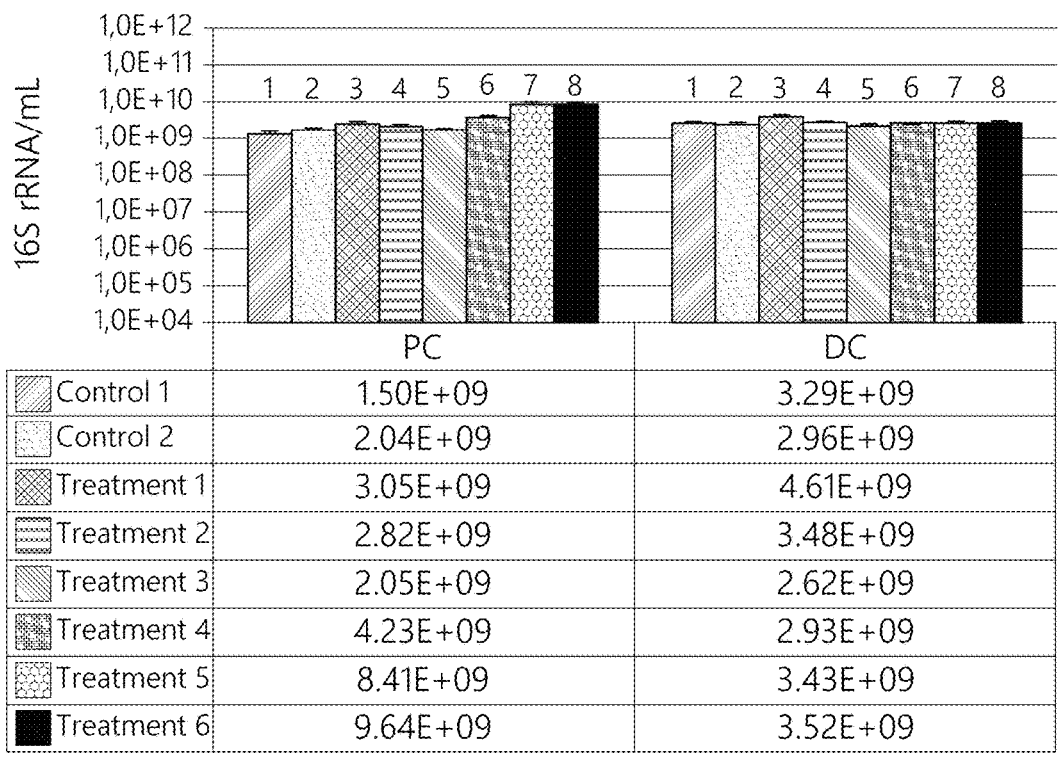
FIG. 14B shows qPCR data for luminal concentration of Bacteroidetes in the arm of the TripleSHIME treated with Epicor. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 14C:
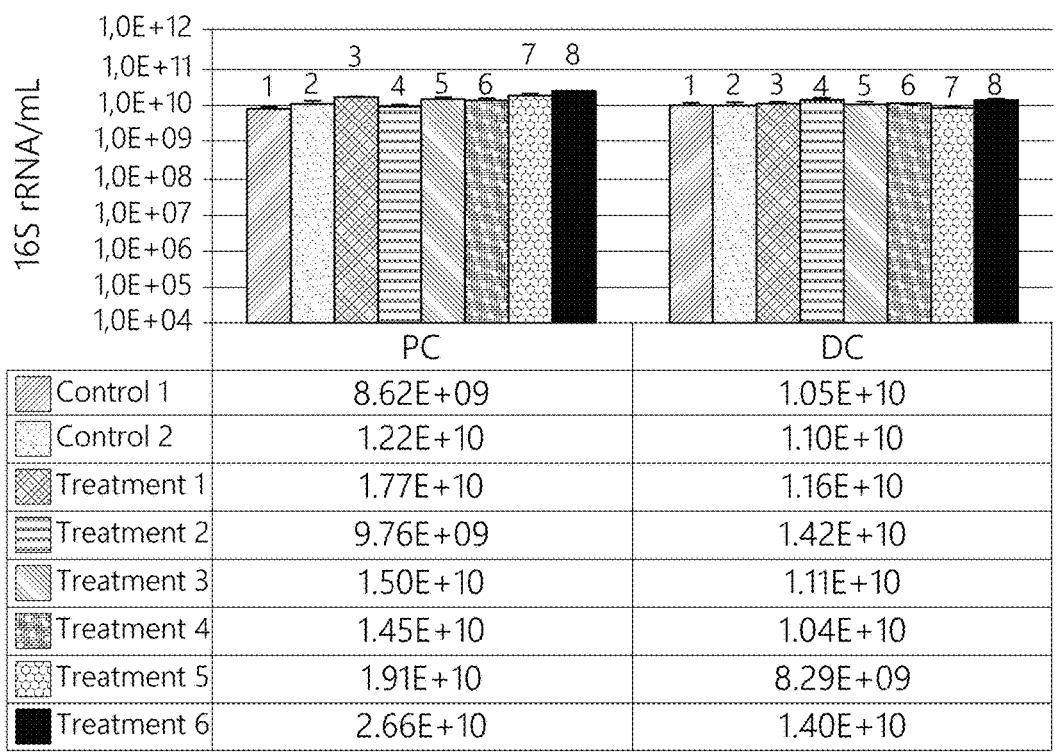
FIG. 14C shows qPCR data for luminal concentration of Firmicutes in the arm of the TripleSHIME treated with Epicor. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 14D:
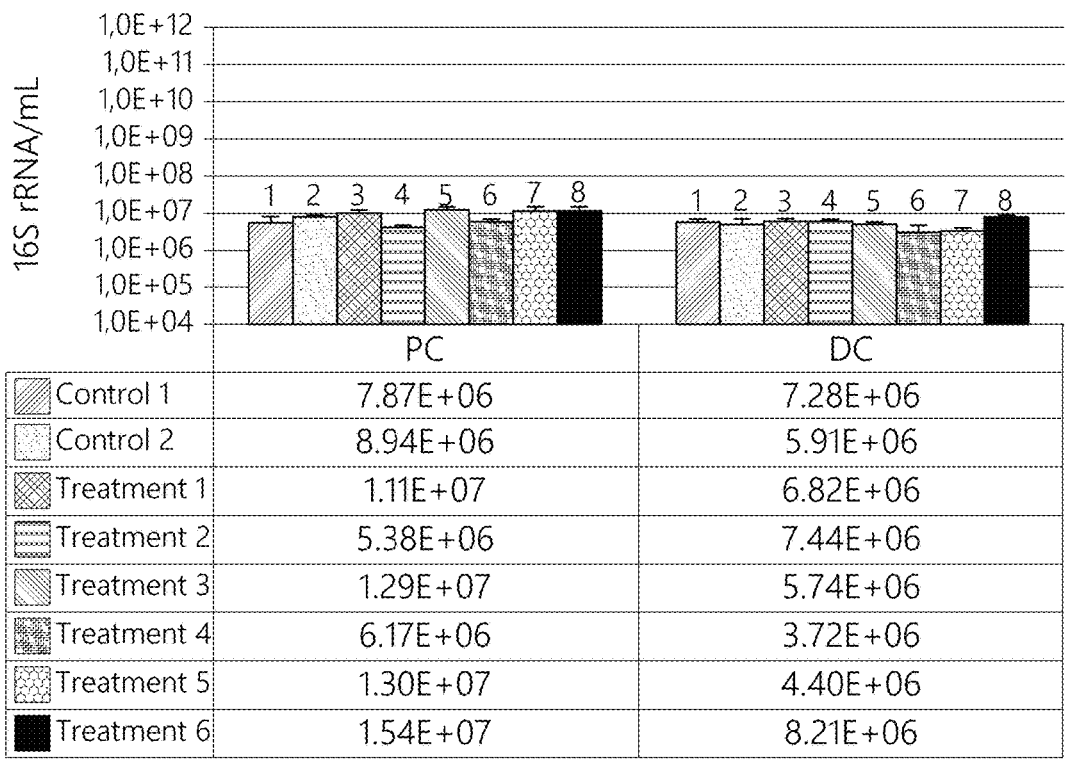
FIG. 14D shows qPCR data for luminal concentration of lactobacilli in the arm of the TripleSHIME treated with Epicor. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 14E:
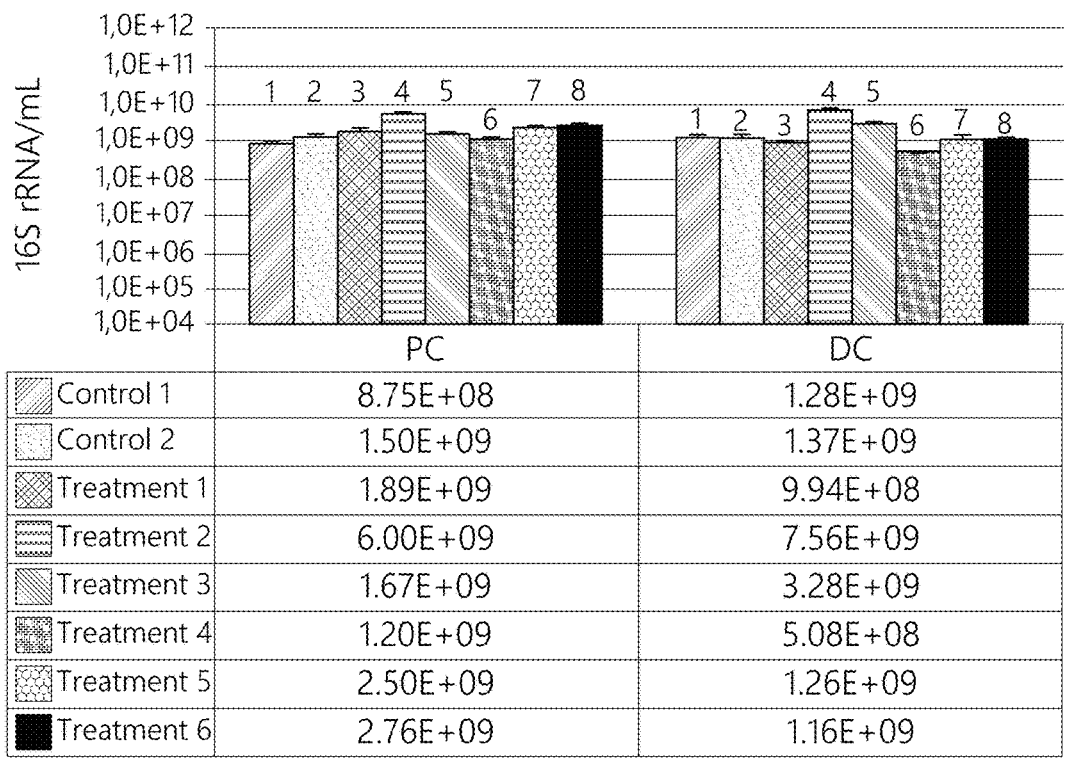
FIG. 14E shows qPCR data for luminal concentration of bifidobacteria in the arm of the TripleSHIME treated with Epicor. Data are presented per experimental week in each colon compartment. Treatments are labeled above the bars of the graph: 1) Control 1; 2) Control 2; 3) Treatment 1; 4) Treatment 2; 5) Treatment 3; 6) Treatment 4 7) Treatment 5; and 8) Treatment 6.
Figure 15:
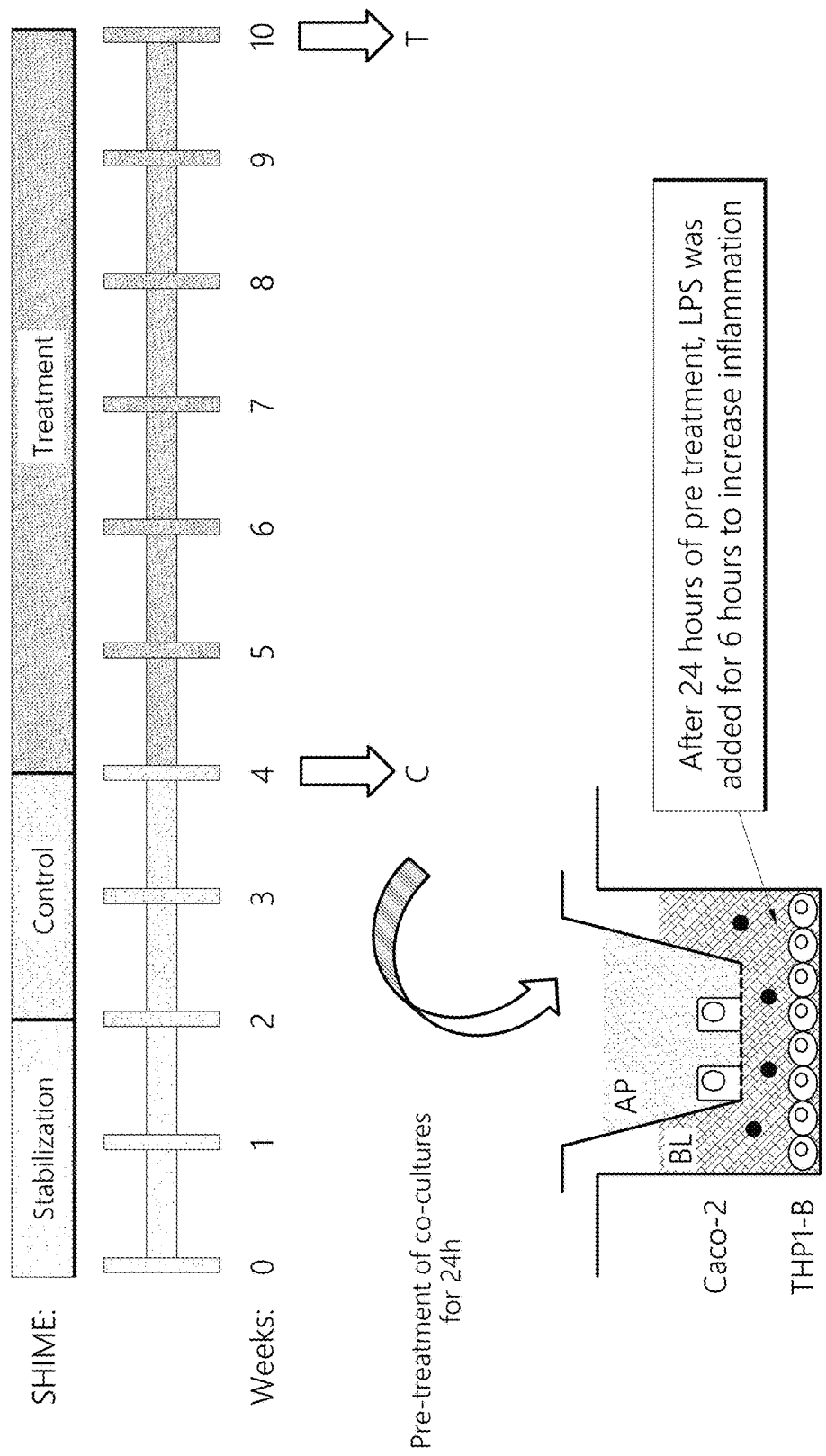
FIG. 15 shows the design of the sample analysis to measure: TEER (24 h), paracellular transport of Lucifer Yellow (24 h) and immune markers (after 6 h LPS) (i.e. IL-6, IL-8, IL-10, TNF-α and NF-κB activity).

The analysis of acid and base consumption in the different colon regions throughout the course of the experiment was shown in FIG. 11A, FIG. 11B, and as consumption of NaOH and HC1 for each of the arms of the TripleSHIME. The data was shown as the average consumption during the control period, the first 3 weeks of treatment, and the last 3 weeks of treatment.

In presence of all test products, the consumption of base was always higher as compared to the acid, indicating that metabolic processes linked to colonic acidification occurred.

However, as no major differences were observed between control and treatment, the changes induced by the test products did not lead to a strong imbalance of the microbial metabolism in the different colon sectors.

This is in line with the data previously presented in which, the increase in SCFA was balanced by the increased proteolytic activity.

Analysis of the Microbial Community Composition

Samples were collected once per week from each colon compartment of the SHIMEs to evaluate the effect of the treatments on the luminal microbial community composition by means of quantitative PCR (qPCR) for total bacteria, bacteroidetes, firmicutes, bifidobacteria, and lactobacilli. The luminal microbial community composition was analyzed using quantitative PCR analysis.

The data was presented per experimental week (2 weeks of control and 6 weeks of treatment) in FIGS. 12A-12E, FIGS. 13A-13E, and FIGS. 14A-14E. The analysis of the qPCR data presented in FIGS. 12A-12E, FIGS. 13A-13E, and FIGS. 14A-14E showed the following trends:

Aloe (3 servings) led to a slight increase of total bacteria in the PC while in the DC no changes were observed. The slight increase can be mainly associated with an increase in Bacteroidetes while Firmicutes were not affected. The product did not show any lactobacillogenic effect. The concentration of bifidobacteria showed a transient peak after 2 weeks of treatment.

Aloe (6 servings) led to an increase of total bacteria both in the PC and in the DC (+0.2 log). This increase may be primarily associated with an increase in Bacteroidetes and in Firmicutes. As for the 3 servings, the product did not show any lactobacillogenic effect. The concentration of bifidobacteria showed a transient increase both in the PC and DC. As compared to the 3 servings, in this case it is possible to observe an effect dose-dependent. In fact, with 6 servings, the concentration of bifidobacteria was higher (as compared to the baseline of the control period) during week 1, 2 and 3 of treatment in the PC and during week 2 and 3 in the DC.

Epicor led to a delayed effect on total bacteria in the PC (up to 0.2 log along week 4, 5 and 6 of treatment). This increase was linked to a higher concentration of both Bacteroidetes (+0.7 log) and Firmicutes. The product did not show any lactobacillogenic effect. As for the 3 servings of Aloe, the concentration of bifidobacteria showed a transient peak after 2 weeks of treatment both in the PC and in the DC.

Due to slight changes occurred in the amount of the different bacterial groups analyzed, a qualitative change may have also occurred (i.e. change of species). Possible qualitative changes may be studied by means of a fingerprinting technique (i.e. DGGE).

Effect on the Gut Wall Modulation—Gut Barrier Permeability and Inflammation

Figures 19A, 19B:
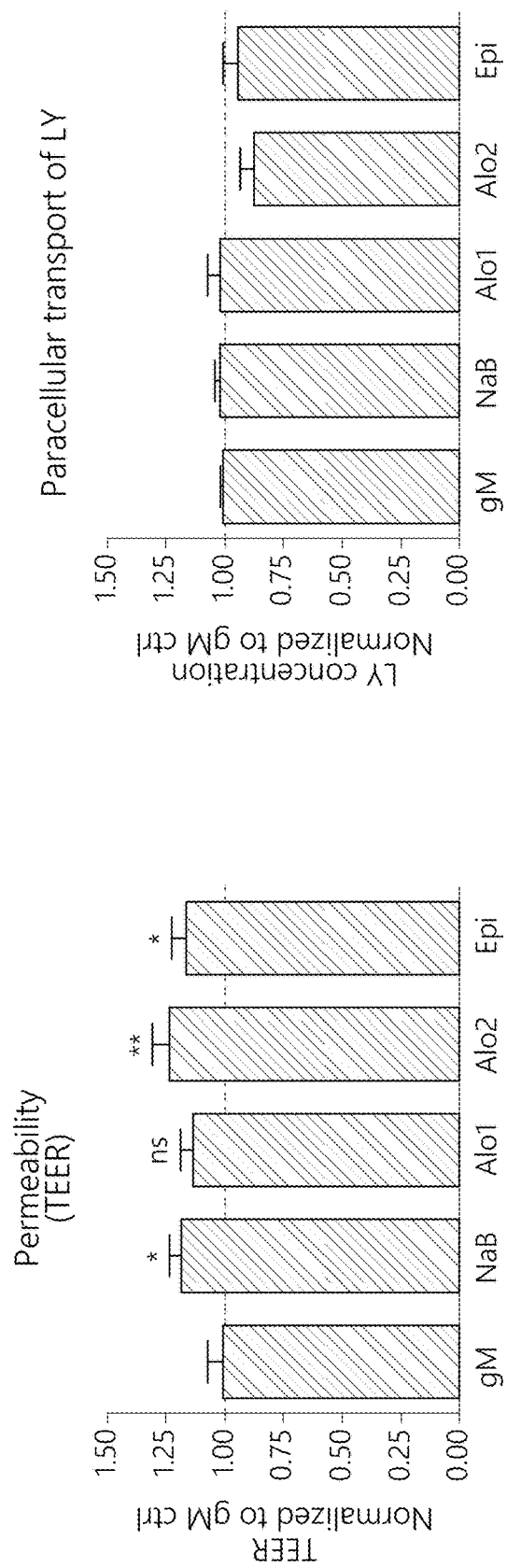
FIGS. 19A to 19B show (FIG. 19A) TEER and (FIG. 19B) Paracellular transport of Lucifer Yellow (LY) on the control tests (gM and NaB) and on the non-fermented study products—Aloe 1 (0.507 g/L), Aloe 2 (1.014 g/L) and EpiCor (1.5 g/L). The TEER and the LY transport were measured 24 h after pre-treatment of the co-cultures in two independent experiments; ns: not significant. No statistical significances were found for the transport of LY.
Figures 19C, 19D:
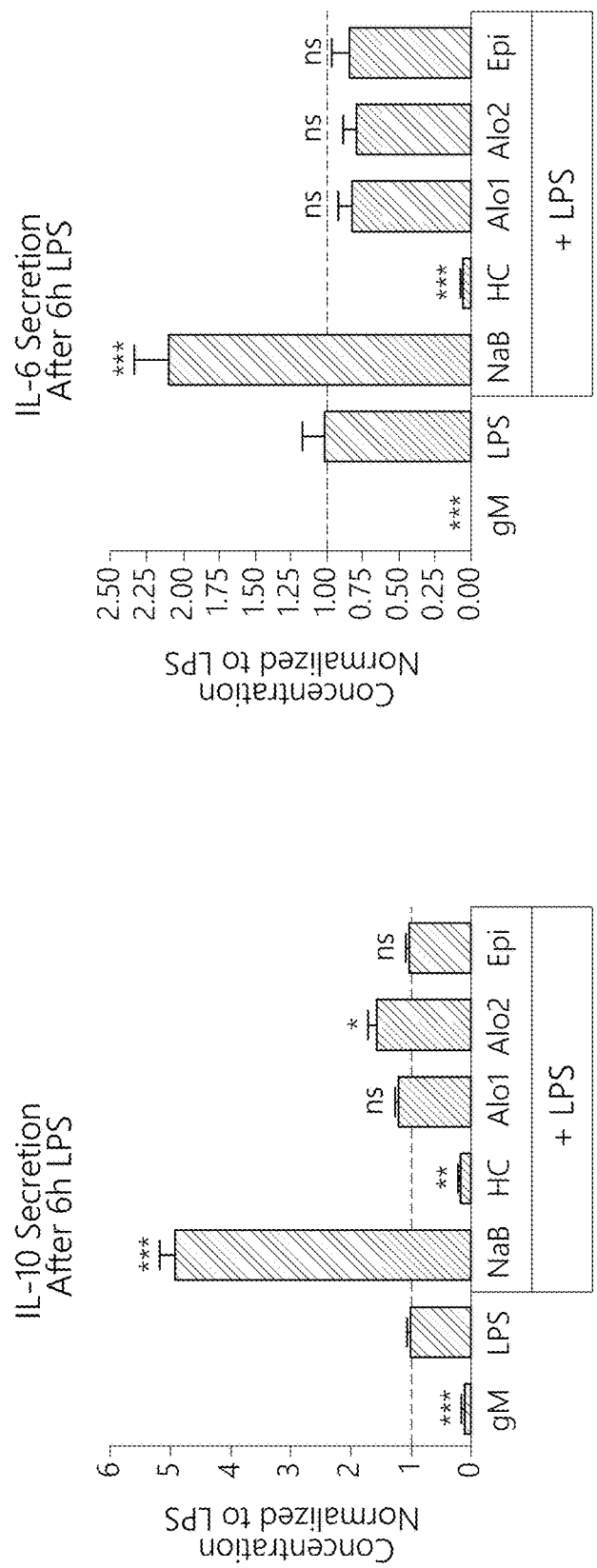
FIGS. 19C to 19F shows (FIG. 19C) IL-10, (FIGS. 19C and 19D) IL-6, (FIGS. 19C and 19E) IL-8 and (FIGS. 19C and 19F) TNF-α on the control tests (gM, LPS, NaB and HC) and on the non-fermented study products—Aloe 1 (0.507 g/L), Aloe 2 (1.014 g/L) and EpiCor (1.5 g/L). Cytokines were measured 6 h after LPS treatment of the co-cultures that were first pre-treated with the testing products for 24 h; ns: not significant.
Figures 19E, 19F:
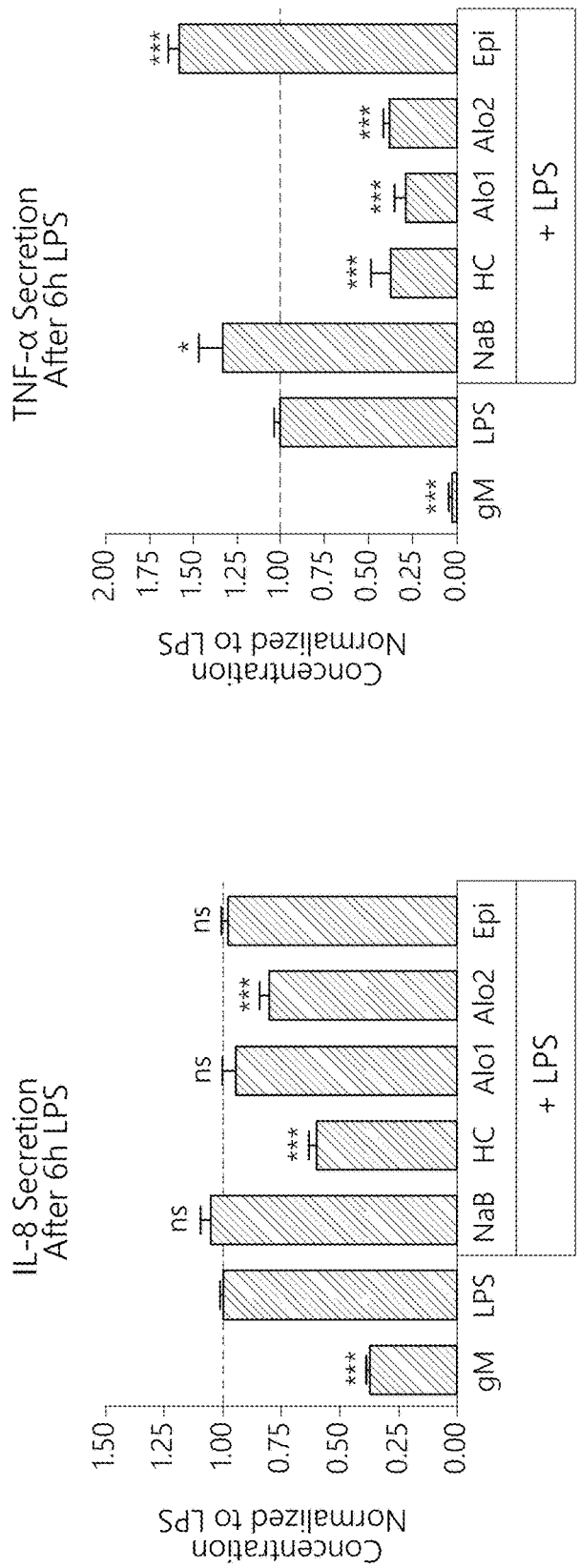
Figure 19G:
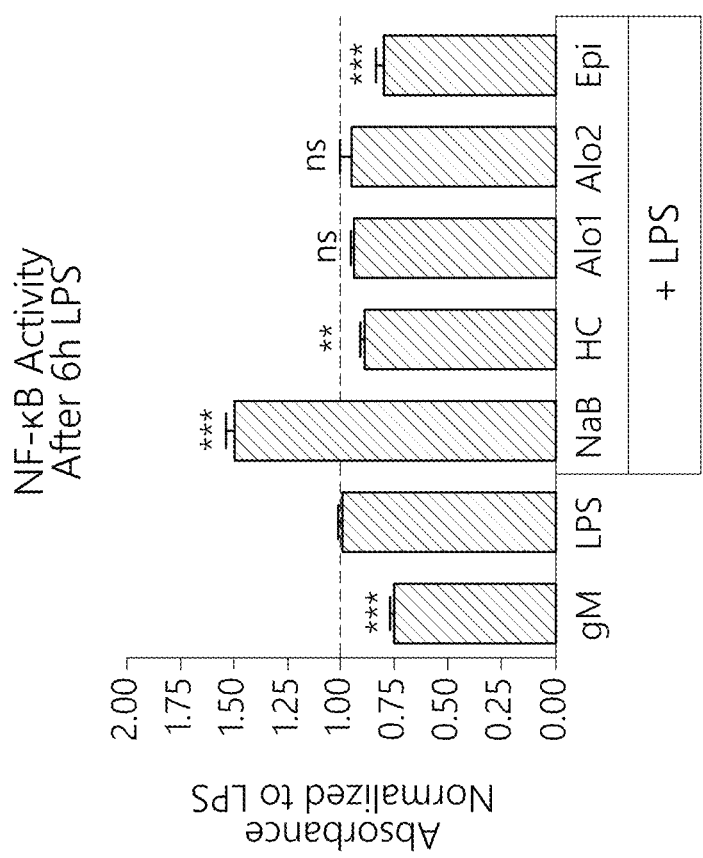
FIG. 19G shows NF-κB activity on the control tests (gM, LPS, NaB and HC) and on the non-fermented study products—Aloe 1 (0.507 g/L), Aloe 2 (1.014 g/L) and EpiCor (1.5 g/L). NF-κB activity was measured 6 h after LPS treatment of the co-cultures that were first pre-treated with the testing products for 24 h; ns: not significant.

The data is presented in the following manner:
1. A first set of graphs (FIGS. 19A-19G) depicts the experimental controls: growth media (gM), lipopolysaccharide (LPS), Sodium butyrate (NaB) and hydrocortisone (HC) and also the study products (Aloe and EpiCor) unprocessed (no digestion/fermentation):
    Two concentrations of Aloe were tested directly on the cells: 0.507 g/L (Alo1) and 1.014 g/L (Alo2)
    One concentration of EpiCor was tested directly on the cells: 1.5 g/L
    All products were freshly prepared in cell culture media and sterile-filtered
    In all graphs the results have been normalized to the control (gM for TEER and LY, and LPS for immune markers); in this manner, the controls are set to 1.0, and the tested conditions are shown as a fold-changes
    Statistical significances were tested by using One-way ANOVA with Dunnett's post-hoc test: *,  and * represent p<0.05, p<0.01 and p<0.001, respectively
2. A second set of graphs (FIGS. 19H-19N depicts the results obtained for the SHIME samples:
    All values have been normalized to the corresponding control period. Therefore, the control samples are set to 1.0, and the treatments are shown as fold-changes.
    Statistical significances were tested by using Student's t-test (C vs. T): *,  and * represent p<0.05, p<0.01 and p<0.001, respectively
    In all graphs: C: control period; T: treatment period; PC proximal colon; DC: distal colon As expected, the growth media control (gM) showed a nearly 20% decrease in the TEER after 24 h due to the damage induced by the activated THP1 cells on the Caco-2 cells (not shown). The Sodium butyrate (NaB; positive control) was able to protect the Caco-2 cells from this damage, and to maintain the TEER of the monolayer when given at low doses (p<0.05) (FIGS. 19A to 19N). As it is possible to see, all pure tested products—Aloe and EpiCor—were also able to protect the monolayer from this damage by maintaining the TEER (although this was only significant for Aloe 2 and EpiCor), both showing similar levels to the NaB.

However, the paracellular transport of small molecules such as LY was almost not affected by any of the tested products; nevertheless, Aloe 2 showed a mild decrease in the paracellular transport of LY, which is in agreement with the increase observed in the TEER.

As shown in FIGS. 19C to 19F, shows that NaB induced NF-κB activity (an effect which is mediated by the attenuation of histone deacetylase (HDAC) inhibitory activities on chromatin). This lead to an increase in acetylation of transcription factors such as NF-κB and consequently to an increase in transcriptional activity. The effects of NaB on cytokines and chemokines was cell line dependent, and had both pro- and anti-inflammatory effects. Here, NaB induced an increase in all cytokines, an effect possibly mediated by the increase in NF-κB-induced gene transcription.

The effects of Aloe and EpiCor seemed to be cytokine dependent. For instance, Aloe is known for its anti-inflammatory properties, and this was also evident here, particularly at the highest concentration tested (Aloe 2). On one hand, Aloe (2) was able to increase LPS-induced IL-10, and on the other hand, to slightly reduce LPS-induced IL-6 (albeit not being significant), IL-8 and TNF-α. Note however, that this did not seem to be dependent on the modulation of NF-αB activity, and may rather be mediated by a post-transcriptional or post-translational mechanism. EpiCor, as pure product, does not seemed to greatly affect LPS-induced cytokines at the dose tested, except for TNF-α, which seems to be highly induced. Finally, as expected, LPS (a bacteria-derived molecule) was able to increase the secretion of both pro- and anti-inflammatory cytokines and to induce NF-κB activity. In contrast, hydrocortisone (HC), being a corticosteroid, acted as an immunosuppressant by dampening the secretion of all LPS-induced immune markers (possibly by decreasing NF-κB activity), as shown in FIG. 19G.

Figures 19H, 19I:
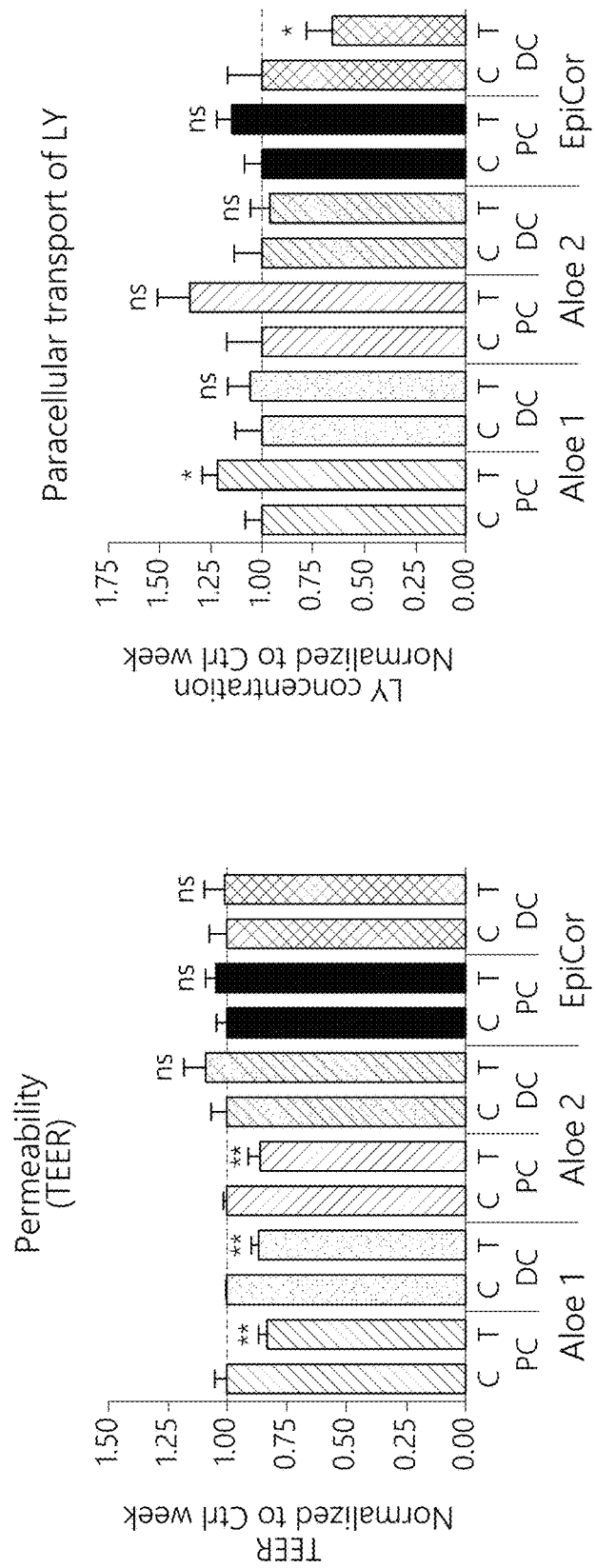
FIGS. 19H-19I shows (FIG. 19H) TEER and (FIG. 19I) Paracellular transport of Lucifer Yellow (LY) on the co-cultures treated with the samples collected from the SHIME fed on Aloe 1 (originally dosed at 0.507 g/L), Aloe 2 (originally dosed at 1.014 g/L) and EpiCor (originally dosed at 1.5 g/L). The TEER and the LY transport were measured 24 h after pre-treatment of the co-cultures in two independent experiments; ns: not significant.
Figure 19K:
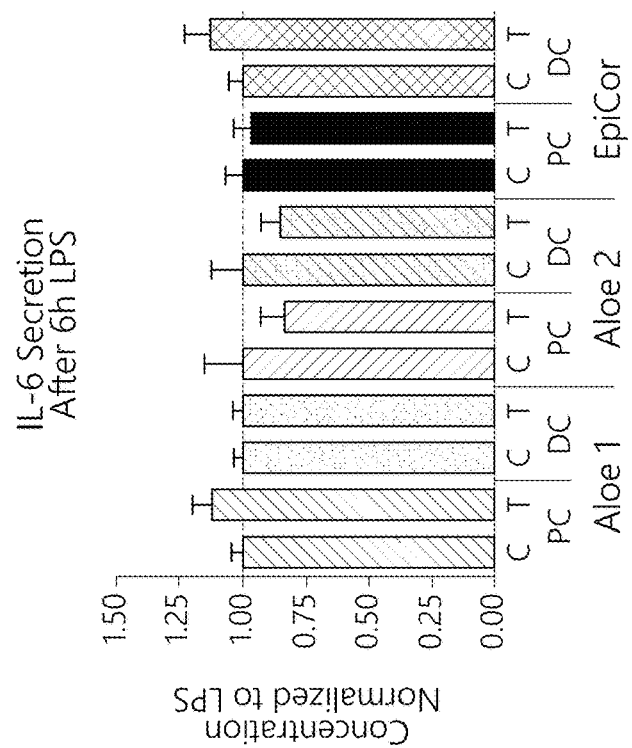
FIGS. 19J-19N shows (FIG. 19J) IL-10, (FIG. 19K) IL-6, (FIG. 19L) IL-8, (FIG. 19M) TNF-α and (FIG. 19N) NF-κB activity on the co-cultures treated with the samples collected from the SHIME fed on Aloe 1 (originally dosed at 0.507 g/L), Aloe 2 (originally dosed at 1.014 g/L) and EpiCor (originally dosed at 1.5 g/L). Cytokines were measured 6 h after LPS treatment of the co-cultures that were first pre-treated with the testing samples for 24 h; ns: not significant. No statistical significances were found for IL-6 and IL-8.
Figure 19J:
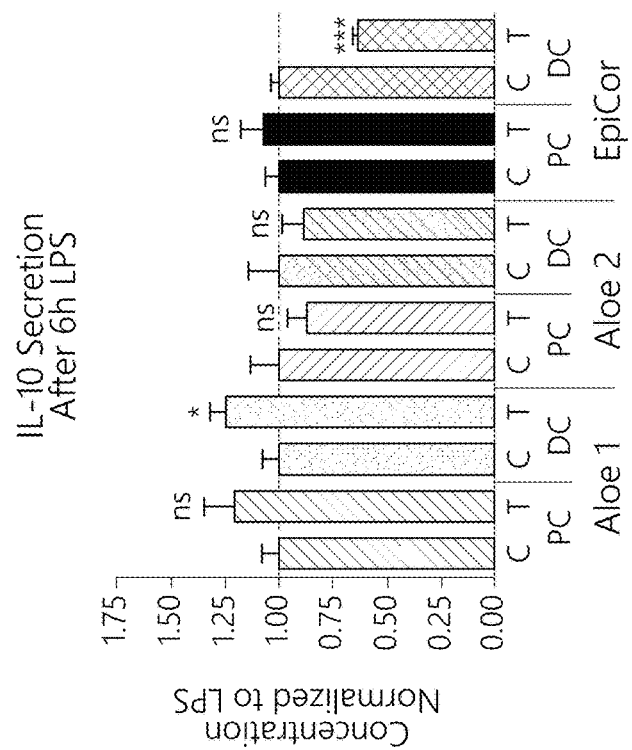
Figures 19L, 19M:
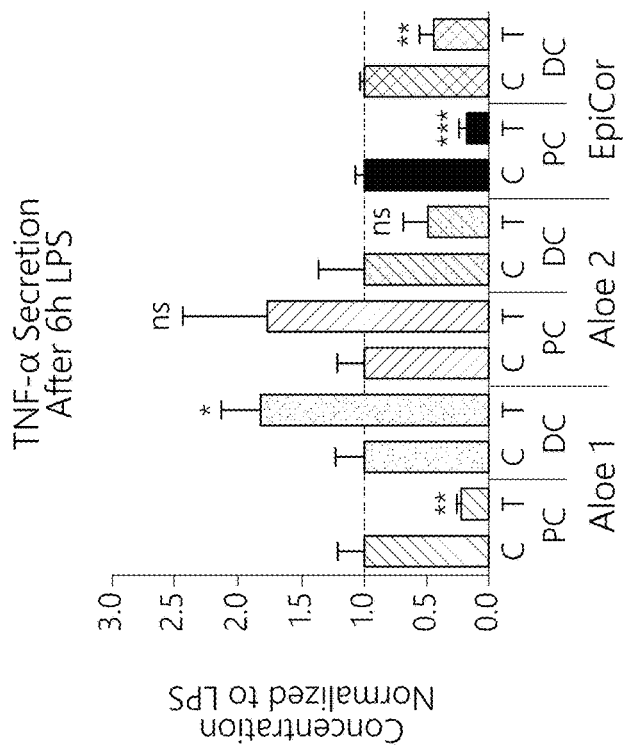
Figure 19N:
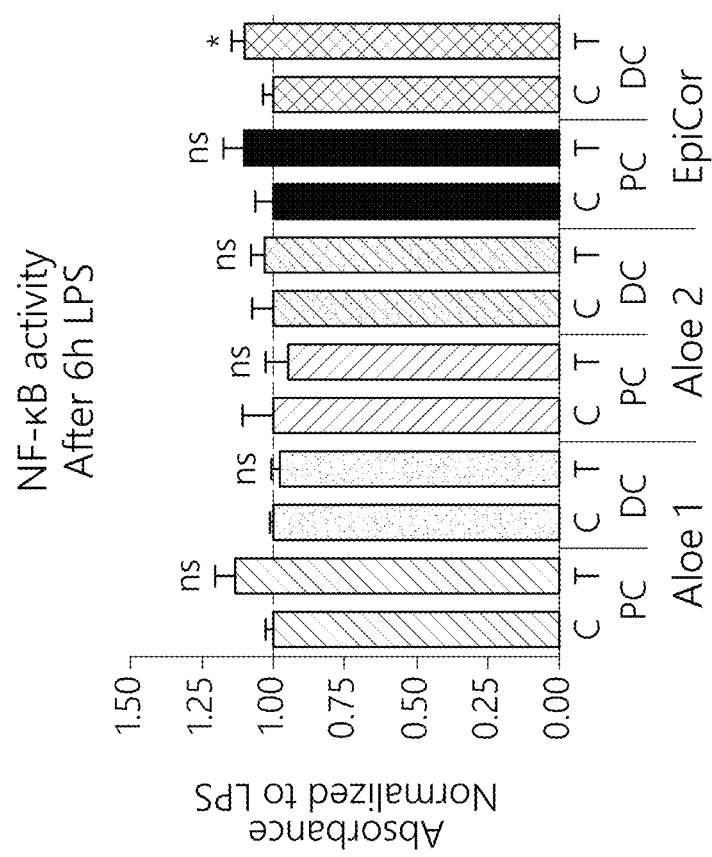

In contrast to the results obtained with the pure products, the fermentation-derived metabolites of Aloe were not able to protect the Caco-2 monolayer from the damage induced by the THP-1 cells; on the contrary, the treatment samples seemed to induce a slight decrease in TEER when compared to the respective control samples; only the sample from the distal colon for Aloe 2 seemed to be the exception (although not significant), as shown in FIGS. 19H to 19I.

The paracellular transport of LY was in agreement with the TEER results for Aloe-derived samples.

In contrast, the metabolites derived from the fermentation of EpiCor did not show an effect on the TEER, but did show an effect on the transport of LY, particularly the sample collected from the distal colon reactor, which showed a decrease in permeability to LY when compared to the respective control.

When evaluating the cytokines production, as shown in FIGS. 19J to 19N, TNF-α seemed to have a more erratic result: it was reduced by Aloe 1_PC and induced by Aloe 1_DC, whereas Aloe 2 showed the opposite (an increase in Aloe 2_PC and a decrease in Aloe 2_DC). In contrast, IL-8 and NF-αB activity are moderately or not affected at all by Aloe-fermentation-derived metabolites.

When considering IL-10 and IL-6, on the one hand, the effects of Aloe-fermentation-derived products on LPS-induced cytokines seemed to be dependent on the colon reactor. On the other hand, the two concentrations seemed to have an almost opposite result: while IL-10 and IL-6 were induced by Aloe 1 by both PC and DC samples, they were reduced by Aloe 2 by both colon samples. In contrast with the unprocessed product, EpiCor-derived metabolites were able to reduce LPS-induced TNF-α levels in the co-cultures, as previously observed.

Figure 20:
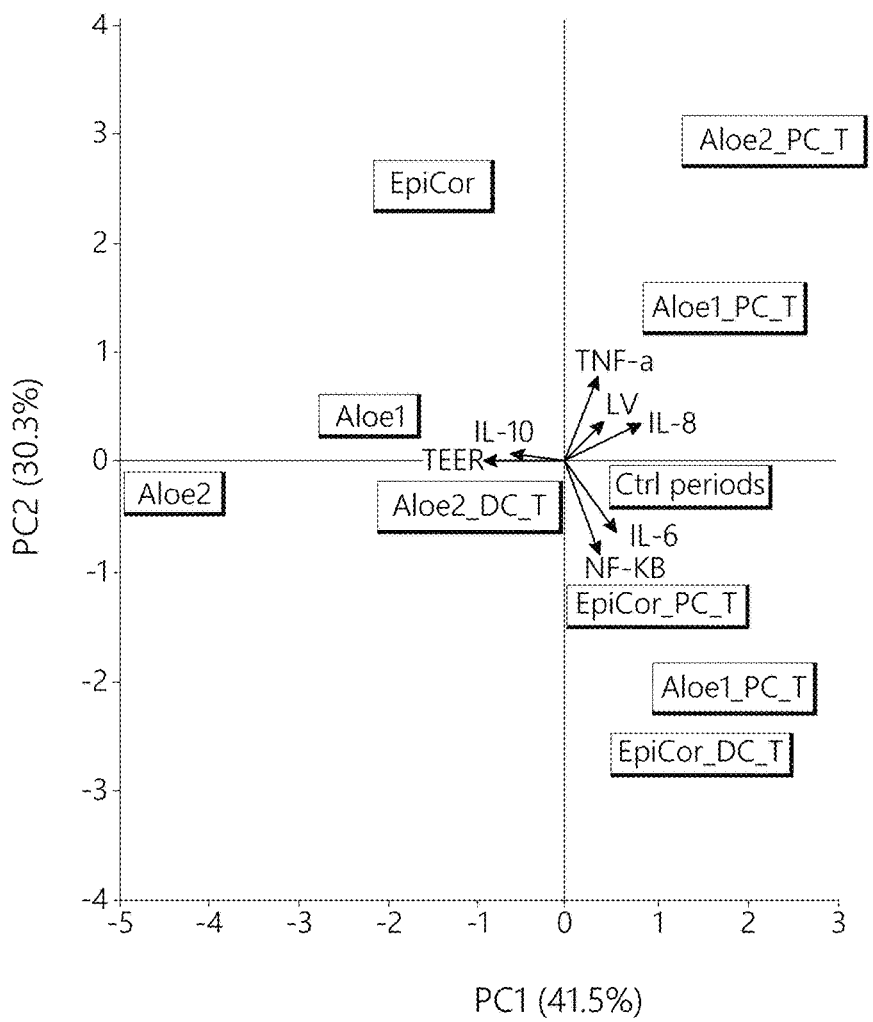
FIG. 20 shows the joint principal component analysis (PCA)/correlation biplot (71.6%).

Finally, in order to investigate the similarities between observations (samples) and the correlation between variables (measurements) a joint PCA/Correlation biplot was made, as shown in FIG. 20. The biplot plotted the variables as vectors and the observations as points.

The data, when reduced to two components, was explained by the first two components by approximately 70%, where the first component accounts for nearly 40% of the variance in the original 7 variables. The variables that mostly contributed to the first component were TEER, IL-8 and IL-10, whereas NF-κB, TNF-α and IL-6 contribute mostly to the second component. The first component mainly separated the unprocessed products from the rest, except for Aloe 2_DC, which groups with Aloe 1 and 2.

The aim of this experiment was to compare 2 doses of Aloe product and a product with demonstrated immune modulating properties (i.e. EpiCor by Embria) with respect to the gut microbial community composition and activity and the modulation of the host gut wall in terms of inflammation and barrier permeability.

All products led to an increase in total SCFA production. More specifically, Aloe led to a higher acetate production in the PC (with 6 servings having a stronger effect as compared to 3), higher propionate in the PC (6 servings) and higher butyrate (both EpiCor and 3 servings of Aloe). Repeated doses of the products were needed to induce these effects.

The administration of the test products had no major impact on the lactate concentration.

All the test products led to a similar increasing trend in ammonium production both in the proximal and the distal colon compartments. This increase was statistically significant for 3 servings of Aloe in the PC and for 6 servings of Aloe and Epicor in the DC.

In presence of all test products the consumption of base was always higher as compared to the acid, indicating that metabolic processes linked to colonic acidification occurred. However, the changes induced by the test products did not lead to a strong imbalance of the microbial metabolism in the different colon sectors.

Aloe (3 servings) led to a slight increase of total bacteria in the PC mainly associated to an increase in Bacteroidetes. The concentration of bifidobacteria showed a transient peak after 2 weeks of treatment. Aloe (6 servings) led to an increase of total bacteria both in the PC and in the DC mainly associated to an increase in Bacteroidetes and in Firmicutes. The concentration of bifidobacteria showed a transient increase both in the PC and DC. Epicor led to a delayed effect on total bacteria in the PC. This increase was linked to a higher concentration of both Bacteroidetes (+0.7 log) and Firmicutes. The concentration of bifidobacteria showed a transient peak after 2 weeks of treatment.

The observed microbial parameters were in line with what was previously observed with EpiCor (using a different donor for the SHIME) and with what was observed in the short-term pre-test conducted with different doses of Aloe product in terms of increased total SCFA production, propionogenic effect and absence of inhibiting effect on the gut microbiota.

The normalized values for all measurements were summarized in FIG. 21, in which the data were translated into gradients of color. When tested unprocessed, higher concentrations of Aloe (1.014 g/L) showed the most interesting results when compared to low concentrations of Aloe (0.507 g/L) and EpiCor (1.5 g/L):

Aloe was able to maintain the TEER (by protecting the Caco-2 cells from the damage induced by THP1 cells), thereby having a positive effect on Caco-2 barrier integrity.

Aloe was also able to increase LPS-induced IL-10 levels (a bona fide anti-inflammatory cytokine), to maintain IL-6 levels and to decrease both LPS-induced IL-8 and TNF-α levels, being the results for the last cytokine the most noticeable, as shown in FIG. 21.

The obtained results were in line with the recognized anti-inflammatory effects of Aloe. However, when fermented, some of these results were no longer apparent, with the exception of Aloe 2_DC, which most closely resembled most the unprocessed Aloe (2) in the overall results. Therefore, these effects are more likely to take place in the small intestine where the product is still in its most intact form.

Example 8

Documentation of Biological Properties of Two Aloe-Based Test Products: An Aloe-Based Whole Leaf (WL) Product and an Aloe-Based Inner Leaf (IL) Product The purpose of this experiment was to compare basic testing results of two aloe-based products, a whole-leaf product and an inner-leaf product, and to gain an understanding of dose responses for the two crude products, as well as in vitro digests thereof, using select antioxidant and anti-inflammatory bioassays.

Initially, it was important to understand whether compounds in test products/fractions enter into living cells, or mediate actions via cellular signaling at the cell membrane level. It was also essential to know the dose response for both types of cellular events for optimizing doses for further bioassays.

The following three tests were performed on the test products in parallel:
1. Antioxidant capacity;
2. Cellular antioxidant protection and bioavailability, using the CAP-e assay;
3. Effect on cellular production of Reactive Oxygen Species (ROS).

The following test products were compared:

| Test Product | Abbreviations | Relevance |
| --- | --- | --- |
| Herbalife Aloe whole leaf juice, filtered, lot #033694 | WL | Compounds immediately available for absorption |
| Herbalife Aloe whole leaf juice, filtered, in vitro digested | WL-IVD | Compounds made available by digestive process |
| Standard dried powder from inner leaf lot #700AQ07VK01 | IL | Compounds immediately available for absorption |
| Standard dried powder from inner leaf, in vitro digested | IL-IVD | Compounds made available by digestive process |
| Phosphate Buffered Saline (PBS) | PBS-IVD | Control |

In preparation for adding the crude powders to cell cultures, the following procedure was followed immediately prior to use on a given test day: A 500 mg portion of each powder was dispersed into 5 mL physiological saline (PBS), and placed on a rocker for an hour to allow aqueous compounds to solubilize into the buffer. After the incubation, solids were removed by centrifugation followed by sterile-filtration through a 0.22 micron filter.

The in vitro digested (IVD) products were prepared as follows: After products were mixed with PBS for 1 hour (described above), human salivary amylase (3.9 µ/mL) was added and products placed at 37° C. for 10 minutes. Hydrochloric acid was then added to lower the pH of samples to 2.0, and porcine pepsin (1.3 mg/mL) added, to mimic the digestive conditions of the stomach. Samples were then placed in a shaker at 37° C. and shaken for 2 hours in order to simulate digestion in the stomach. Following this, the pepsin enzyme was irreversibly inactivated by raising the pH of samples to 7.0 using sodium bicarbonate. Aliquots of the IVD products were kept frozen at −20° C., and one aliquot of each product thawed immediately prior to use on a given test day.

Total Antioxidant Capacity

The products were tested in the Folin-Ciocalteu assay (also known as the Total Antioxidant Capacity assay, or the total phenolics assay). This assay makes use of the Folin-Ciocalteu reagent to measure antioxidants. The assay is performed by adding the Folin-Ciocalteu's phenol reagent to serial dilutions of extract, thoroughly mixing, and incubating for 5 minutes. Sodium carbonate is added, starting a chemical reaction producing a color. The reaction is allowed to continue for 30 minutes at 37° C. Optical absorbance is measured at 765nm in a colorimetric plate reader. Gallic acid is used as a reference standard, and the data reported in Gallic Acid Equivalents per gram product.

Cell-based Antioxidant Protection Assay

The method used allowed assessment of antioxidant potential that was comparable to the ORAC test, but only allowed measurement of antioxidants that were able to cross the lipid bilayer cell membrane, enter the cells, and provide biologically meaningful antioxidant protection under conditions of oxidative stress.

The CAP-e bioassay was specifically developed to work with natural products and ingredients. The method has been used on multiple types of natural products and ingredients, published in the peer-reviewed scientific literature.

The red blood cell (RBC) was used as the model cell type. The RBC is an inert cell type, in contrast to other cell types such as PMN cells. This assay, as shown in FIG. 22, was particularly developed to be able to assess antioxidants from complex natural products in a cell-based system.

Freshly purified human RBC were washed repeatedly in physiological saline, and then exposed to the test products. During the incubation with a test product, any antioxidant compounds able to cross the cell membrane could enter the interior of the RBC. Then the RBC were washed to remove compounds that were not absorbed by the cells, and loaded with the DCF-DA dye, which turned fluorescent upon exposure to reactive oxygen species. Oxidation was triggered by addition of the peroxyl free radical generator AAPH. The fluorescence intensity was evaluated. The low fluorescence intensity of untreated control cells served as a baseline, and RBC treated with AAPH alone served as a positive control for maximum oxidative damage.

If a reduced fluorescence intensity of RBC exposed to a test product was observed and subsequently exposed to AAPH, this indicated that the test product contained antioxidants available to penetrate into the cells and protect them from oxidative damage.

Effect on Free Radical Formation by Inflammatory Cells

Many natural products with antioxidant capacity also reduce the ROS formation in inflammatory cells. However, other products may actually increase the ROS formation, despite antioxidant capacity, and this may indicate an interesting cooperation between support of antimicrobial defense mechanisms and antioxidant capacity.

Figure 23:
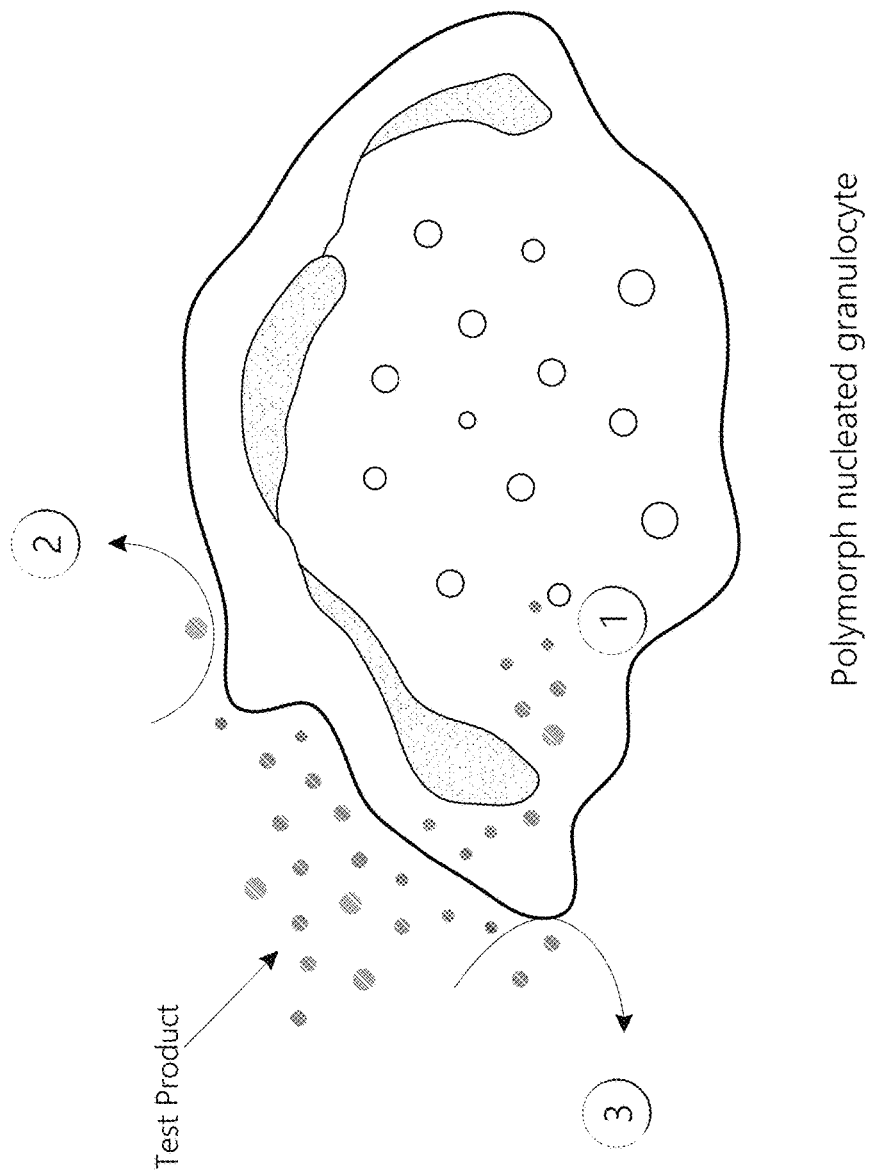
FIG. 23 is a diagram showing that the mechanisms by which natural products may affect PMN cell ROS.

Thus, natural products may affect PMN cell ROS formation by three different mechanisms (as shown in FIG. 23):
1. Neutralizing ROS by direct antioxidant affect;
2. Triggering an anti-inflammatory cellular signal, leading to reduced ROS formation;
3. Triggering an immune reaction, leading to enhanced ROS formation.

Human polymorphonuclear (PMN) cells are used for testing effects of a product on ROS formation. This cell type constitutes approximately 70% of the white blood cells in humans. PMN cells produce high amounts of ROS upon certain inflammatory stimuli.

Freshly purified human PMN were exposed to the test products. During the incubation with a test product, any antioxidant compounds able to cross the cell membrane could enter the interior of the PMN cells, and compounds that trigger a signaling event can do so. Then the cells were washed, loaded with the DCF-DA dye, which turns fluorescent upon exposure to ROS. Formation of ROS was triggered by addition of $H_2O_2$. The fluorescence intensity of the PMN cells was evaluated by flow cytometry. The low fluorescence intensity of untreated control cells served as a baseline and PMN cells treated with $H_2O_2$ alone served as a positive control.

If the fluorescence intensity of PMN cells exposed to an extract, and subsequently exposed to $H_2O_2$, was reduced compared to $H_2O_2$ alone, this indicated that a test product had anti-inflammatory effects.

In contrast, if the fluorescence intensity of PMN cells exposed to a test product was increased compared to $H_2O_2$ alone, this indicated that a test product had pro-inflammatory effects by enhancing this aspect of anti-microbial immune defense mechanisms.

The testing was performed three times on cells from different healthy donors.

Total Antioxidant Capacity

Figure 24:
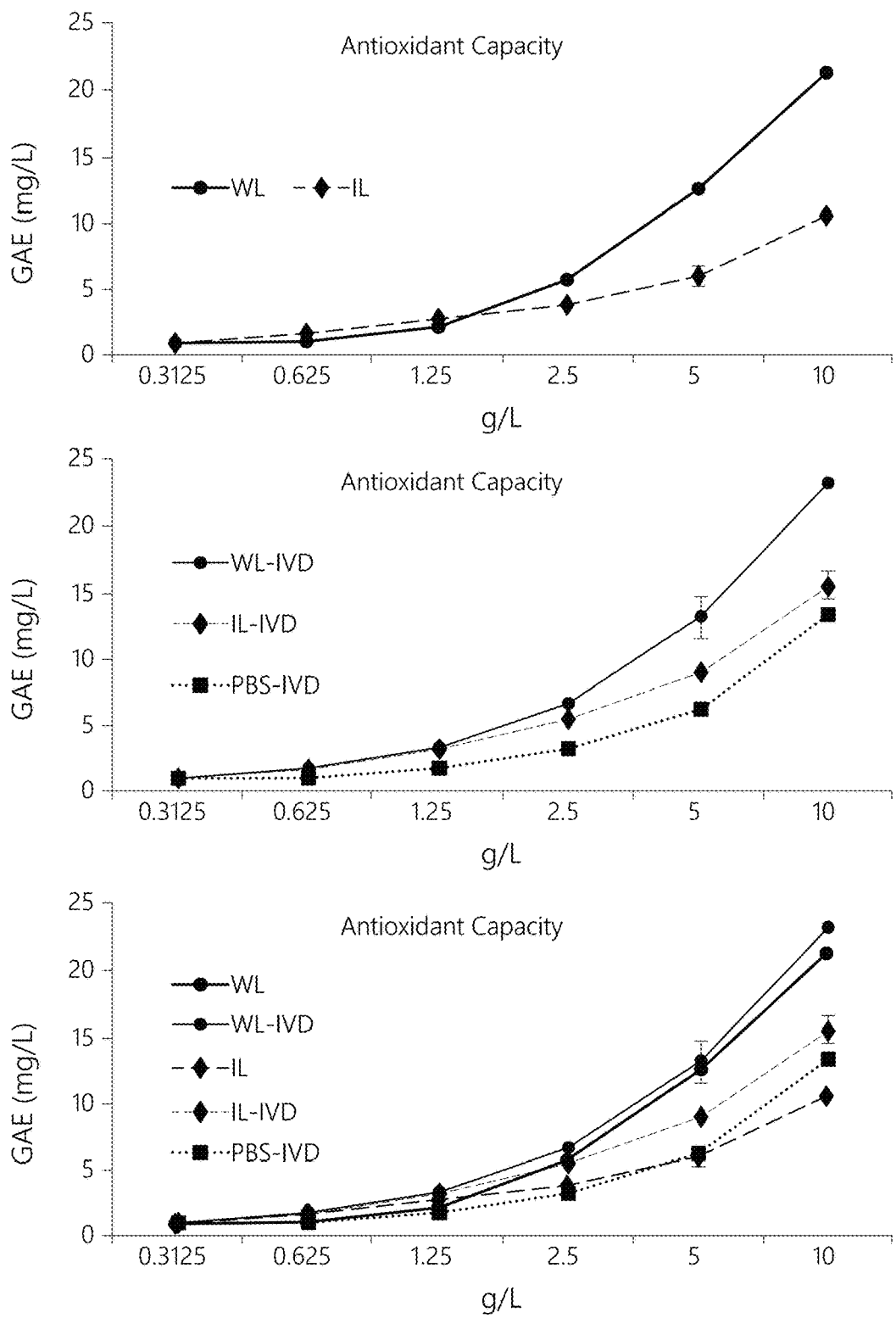
FIG. 24 is a graphical depiction of the total antioxidant capacity of products tested. The top graph shows the crude products. The middle graph shows the products and control taken through the in vitro digestion process. The bottom graph shows all data combined into an overlay graph for reference.

The results in FIG. 24 are shown for the total antioxidant capacity for the two crude products (top graph), followed by the two products taken through the digestive process (middle graph), and an overlay of all test products (bottom graph). The crude products are shown with solid lines, whereas the products taken though the in vitro digestion process (IVD) are shown with dashed lines. The buffer/reagent control for the in vitro digestion is shown as a dotted line.

The whole leaf product (WL) showed approximately two-fold higher antioxidant capacity than the inner leaf product (IL).

When comparing the whole leaf IVD and the inner leaf IVD to each other and the PBS-IVD buffer control, the whole leaf IVD had good antioxidant capacity, whereas the inner leaf IVD product showed very similar results to the PBS-IVD buffer control in this assay.

Cellular Antioxidant Protection Assay

Figure 25:
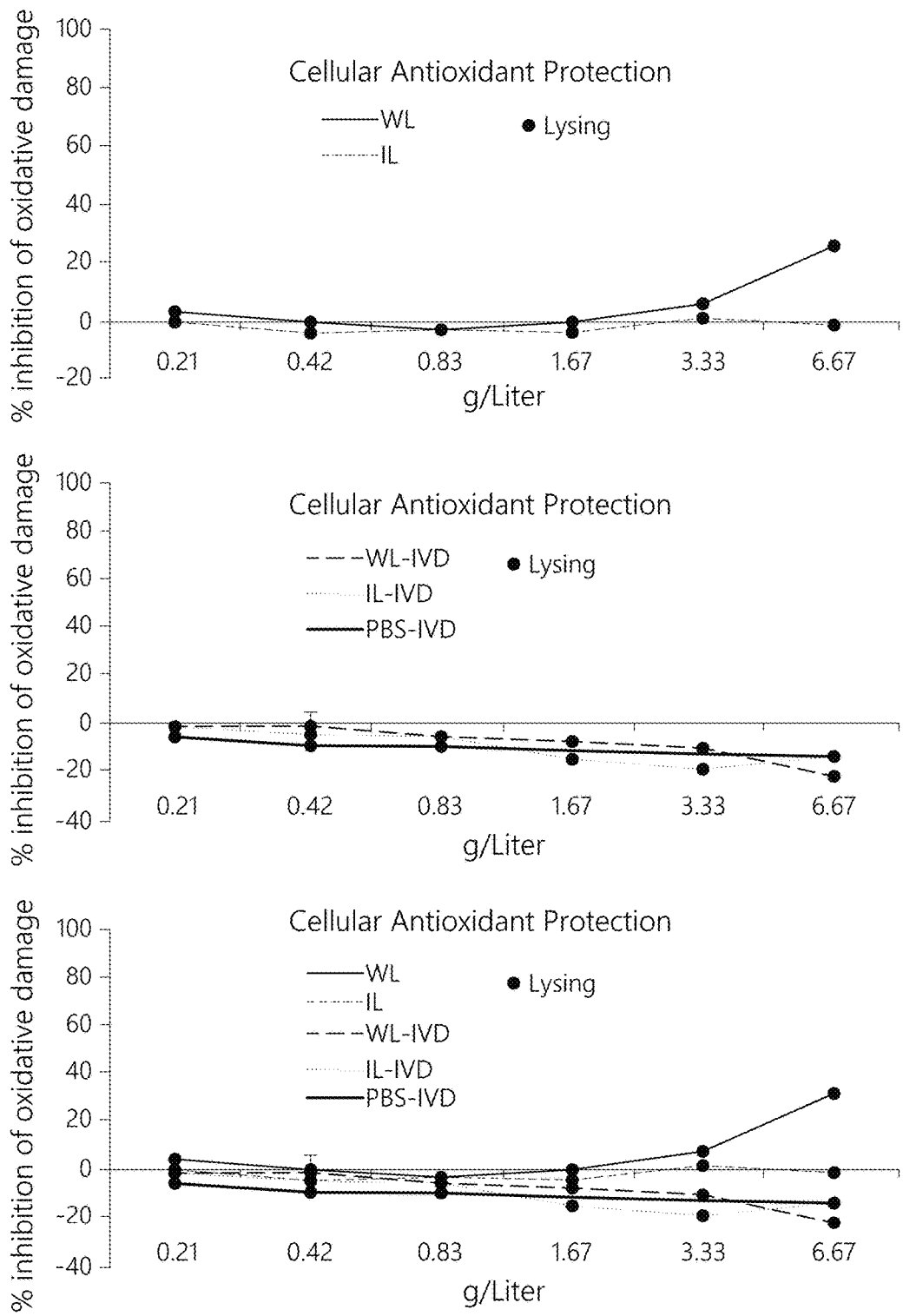
FIG. 25 is a graphical depiction of the cellular antioxidant protection (CAP-e) of the products tested. The top graph shows the crude products. The middle graph shows the products and control taken through the in vitro digestion process. The bottom graph shows all data combined into an overlay graph for reference.

The results in FIG. 25 are shown for the cellular antioxidant protection for the two crude products (top graph), followed by the 2 products taken through the digestive process (middle graph), and an overlay of all products (bottom graph). The crude products are shown with solid lines, whereas the products taken though the in vitro digestion process (IVD) are shown with dashed lines. The buffer/reagent control for the in vitro digestion is shown as a dotted line.

The whole leaf (WL) product showed mild cellular antioxidant protection at the highest doses. However, the cells showed some lysing at those doses.

None of the other products/digest fractions showed cellular antioxidant protection in this assay.

This data served as a crucial foundation for interpreting the mechanisms of action in the ROS assay.

Effect on Free Radical Formation by Inflammatory Cells

In this assay if the fluorescence intensity of PMN cells exposed to an extract, and subsequently exposed to $H_2O_2$, was reduced compared to $H_2O_2$ alone, this indicated that a test product had anti-inflammatory effects.

In contrast, if the fluorescence intensity of PMN cells exposed to a test product was increased compared to $H_2O_2$ alone, this indicated that a test product had pro-inflammatory effects by enhancing this aspect of anti-microbial immune defense mechanisms. Note: WL-IVD induced PMN cell death at higher doses.

Figure 26:
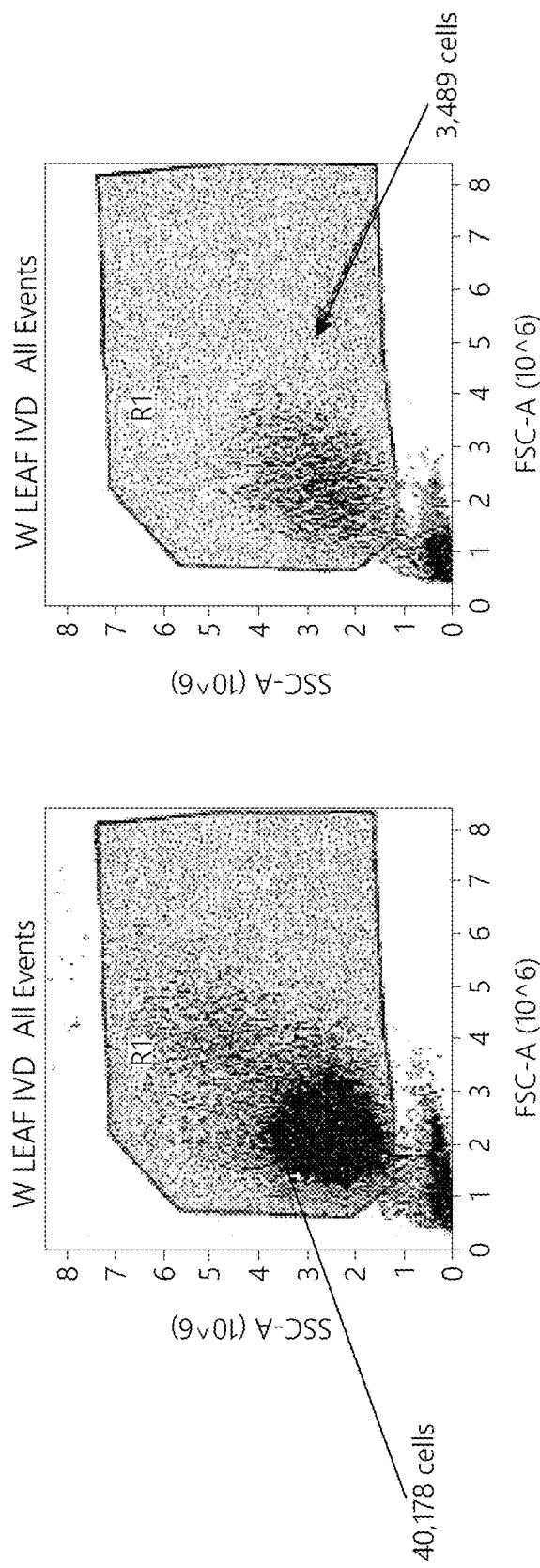
FIG. 26 shows data displays from the Attune acoustic flow cytometer. The dot plots depict relative cellular size along the X-axis, and the relative cellular granularity along the Y-axis. Live and functional PMN cells are positioned in an area that defines the electronic gate for data analysis of ROS formation. The example shown to the left is from a sample of healthy PMN cells, where treatment of the cells by test product did not compromise cellular integrity, and a robust amount of cells were present in the sample. The dot plot to the right shows that PMN cells treated with the highest dose of whole Leaf IVD have undergone cell death, and less than 10% of the cells remained in the area that defines live and functional PMN cells. Even those few remaining cells were likely undergoing cell death and not functioning normally. The data showed that the cells produced high amounts of ROS. Data from this dose of WL IVD is marked by "X" on data graphs in FIG. 27 and FIG. 30.
Figure 27:
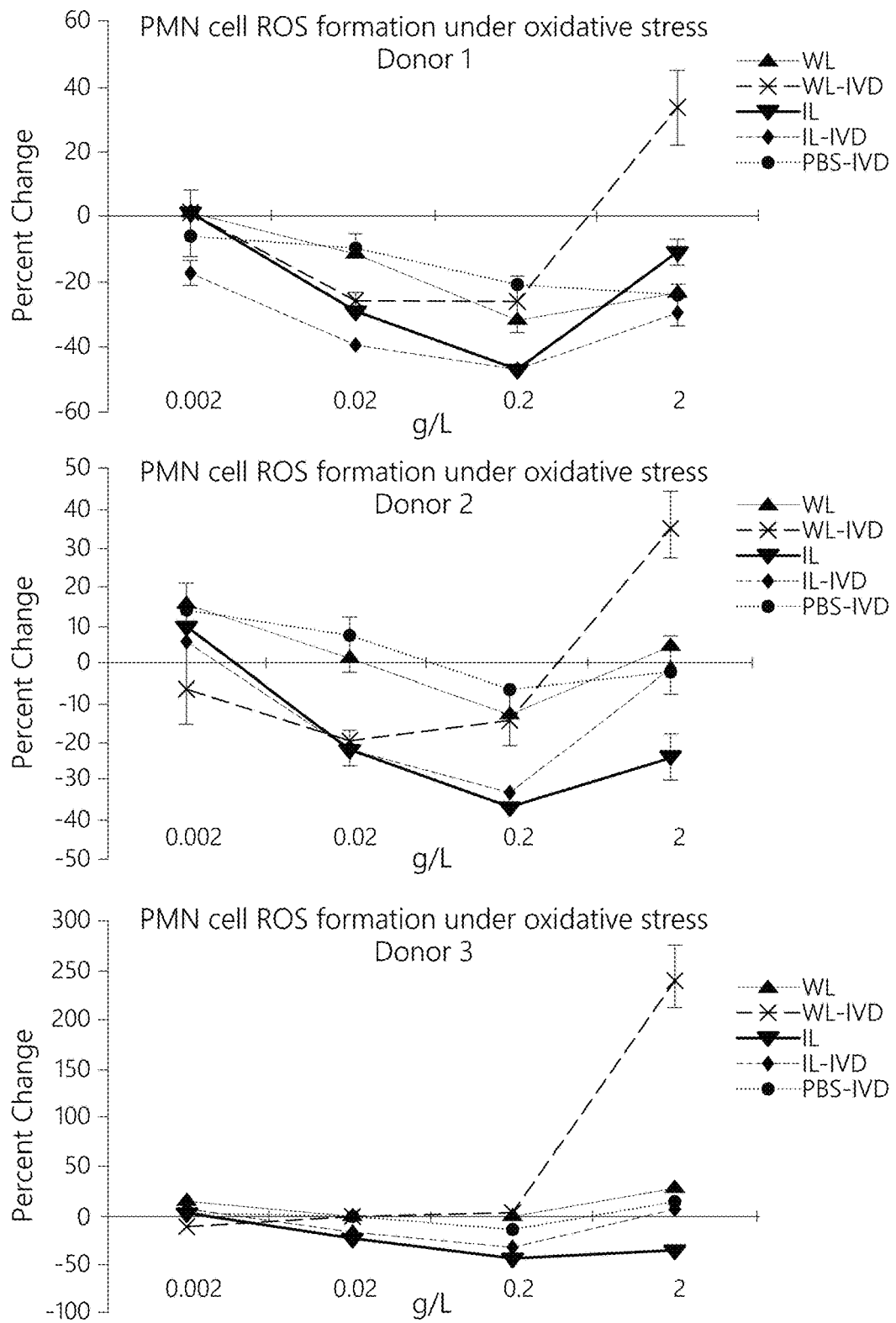
FIG. 27 is a graphical depiction of the reactive oxygen species assay. PMN cells were used to show the effects of products on ROS formation under oxidative stress. These are overlay graphs of products tested using each donor's PMN cells. Similar responses were seen in 2 of the 3 donors tested, where the inner leaf product and its IVD had more robust anti-inflammatory activity than whole leaf and its IVD. Due to the cell death seen in some cultures when exposed to higher doses of certain products (example: WL-IVD), the ROS data from those cultures are not valid, and are indicated by an "X" on those data points in the graphs in FIG. 27.
Figure 28:
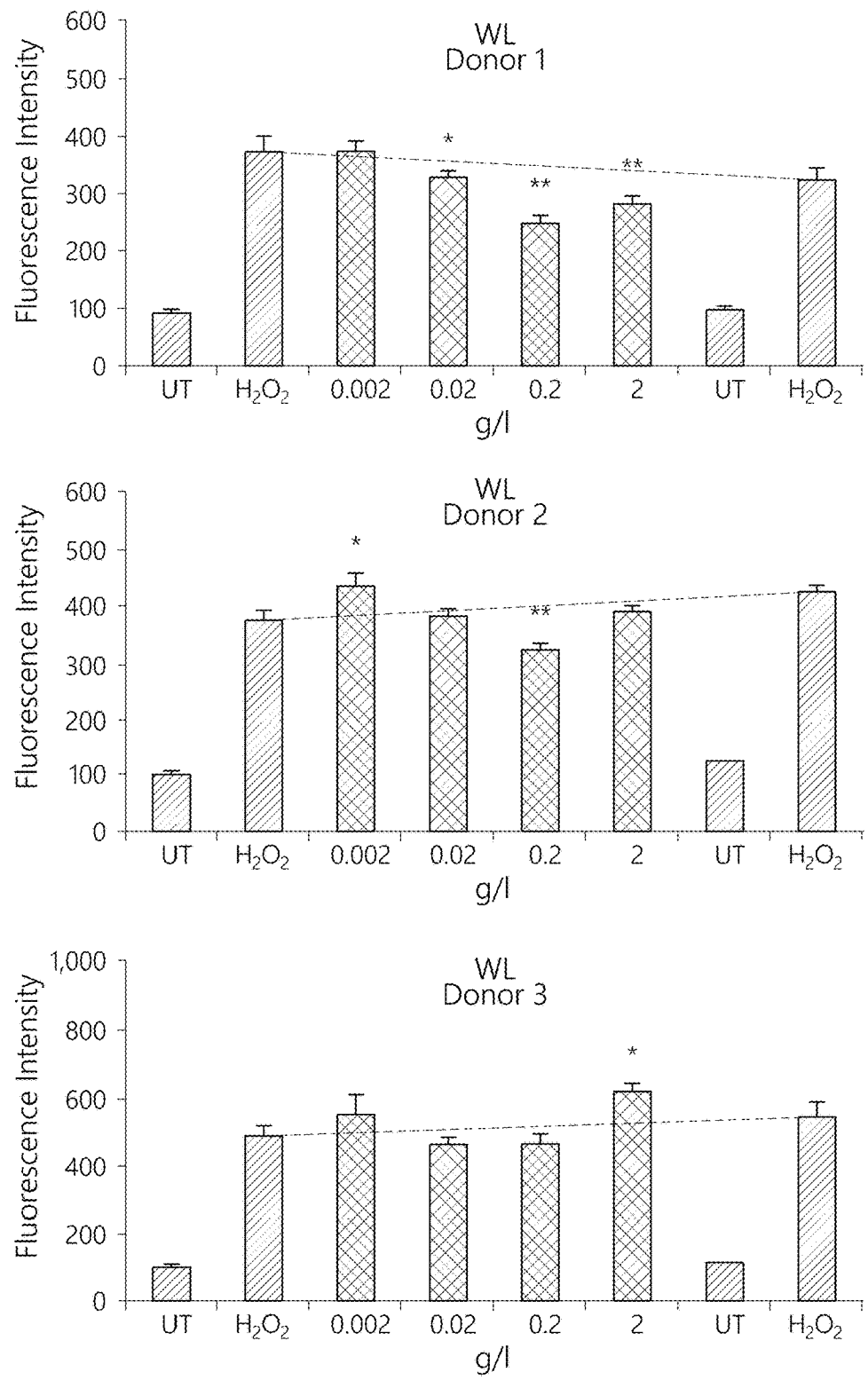
FIG. 28 is a graphical depiction of a Reactive Oxygen Species (ROS) assay using human PMN cells from healthy donors under oxidative stress. The bar graphs show intracellular ROS formation in cells exposed to the whole leaf product, compared to untreated (UT) control cells and H2O2-treated (H2O2) positive control cultures. When a test product triggered an increase or decrease of ROS formation that was significantly different from the H2O2 controls, it is indicated by *p<0.05, **p<0.01. The thin line above the bar graphs indicates the within-assay consistency over time for the $H_2O_2$ controls run before (left) and after (right) all product samples.
Figure 29:
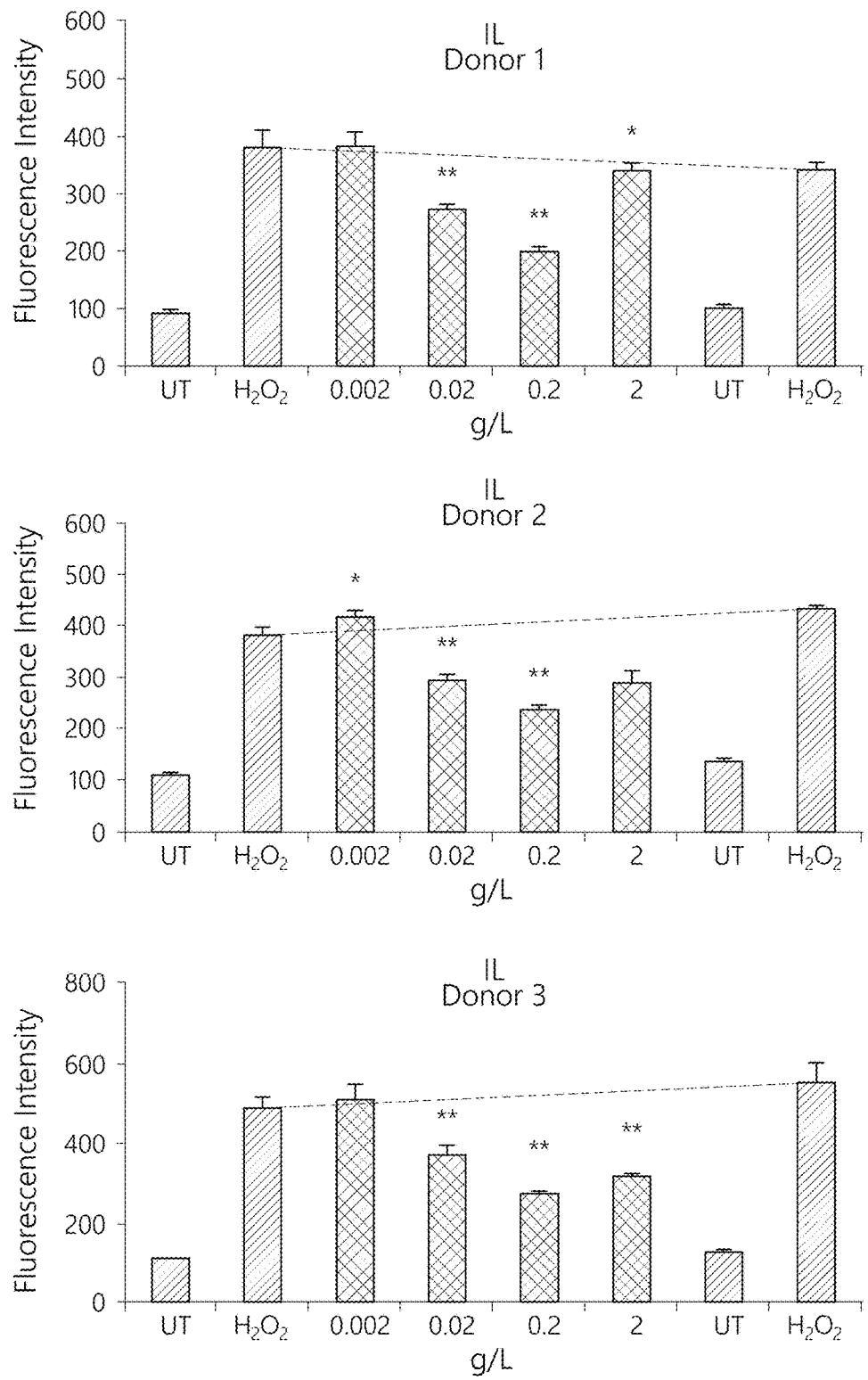
FIG. 29 is a graphical depiction of a Reactive Oxygen Species (ROS) assay using human PMN cells from healthy donors under oxidative stress. The bar graphs show intracellular ROS formation in cells exposed to the inner leaf product, compared to untreated (UT) control cells and $H_2O_2$-treated ($H_2O_2$) positive control cultures. When a test product triggered an increase or decrease of ROS formation that was significantly different from the H2O2 controls, it is indicated by *p<0.05, **p<0.01. The thin line above the bar graphs indicates the within-assay consistency over time for the $H_2O_2$ controls run before (left) and after (right) all product samples.
Figure 30:
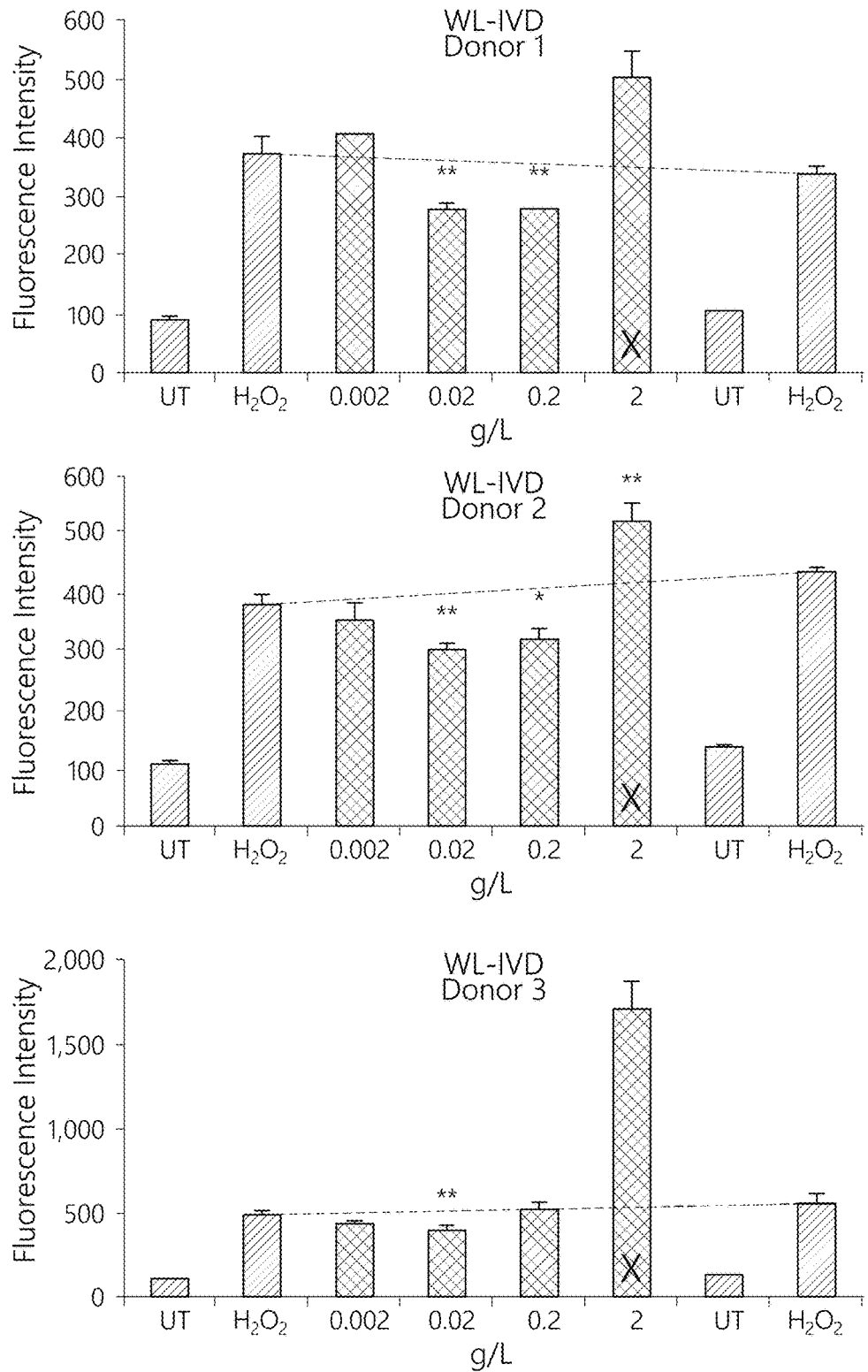
FIG. 30 is a graphical depiction of a Reactive Oxygen Species (ROS) assay using human PMN cells from healthy donors under oxidative stress. The bar graphs show intracellular ROS formation in cells exposed to the digested whole leaf product, compared to untreated (UT) control cells and $H_2O_2$-treated ($H_2O_2$) positive control cultures. When a test product triggered an increase or decrease of ROS formation that was significantly different from the H2O2 controls, it is indicated by *p<0.05, **p<0.01. The thin line on the bar graphs indicates the within-assay consistency over time for the $H_2O_2$ controls run before (left) and after (right) all product samples.
Figure 31:
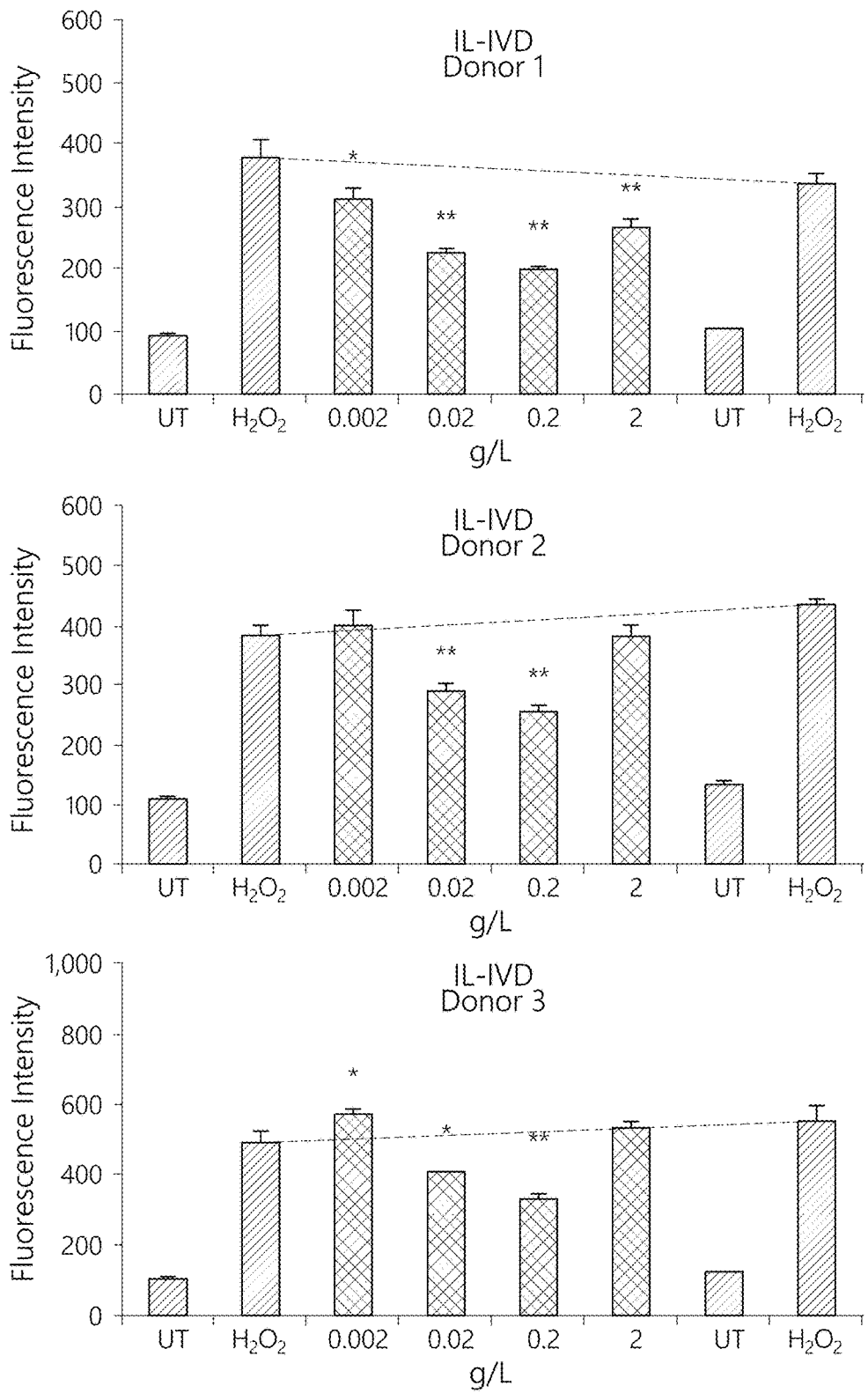
FIG. 31 is a graphical depiction of a Reactive Oxygen Species (ROS) assay using human PMN cells from healthy donors under oxidative stress. The bar graphs show intracellular ROS formation in cells exposed to the digested inner leaf product, compared to untreated (UT) control cells and $H_2O_2$-treated ($H_2O_2$) positive control cultures. When a test product triggered an increase or decrease of ROS formation that was significantly different from the $H_2O_2$ controls, it is indicated by *p<0.05, **p<0.01. The thin line indicates the within-assay consistency over time for the $H_2O_2$ control.
Figure 32:
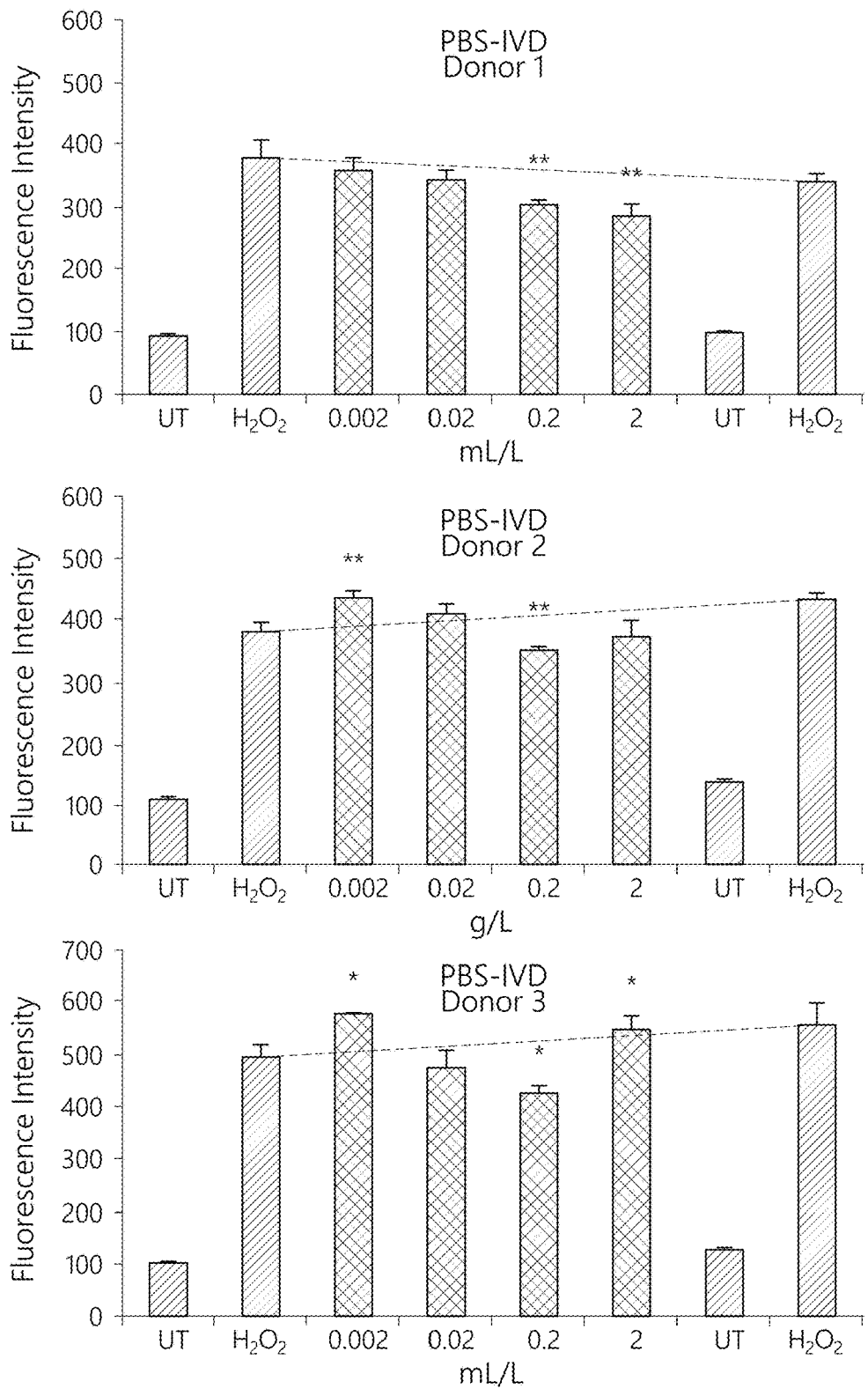
FIG. 32 is a graphical depiction of a Reactive Oxygen Species (ROS) assay using human PMN cells from healthy donors under oxidative stress. The bar graphs show intracellular ROS formation in cells exposed to the digestion buffer control, compared to untreated (UT) control cells and $H_2O_2$-treated ($H_2O_2$) positive control cultures. When a test product triggered an increase or decrease of ROS formation that was significantly different from the $H_2O_2$ controls, it is indicated by *p<0.05, **p<0.01. The thin line indicates the within-assay consistency over time for the $H_2O_2$ controls run before (left) and after (right) all product samples.

Some degree of cell death was seen in some cultures when exposed to higher doses of certain products (example WL-IVD 2 g/L). FIG. 26 shows examples of flow cytometry histograms of samples with good PMN cell viability versus poor viability (increased cell death). The ROS data from cultures with extensive cell death are not valid, and are indicated by an "X" for those data points in the data graphs in FIG. 27 and FIG. 30.

Total Antioxidant Capacity

The whole leaf (WL) product showed higher antioxidant capacity than the inner leaf (IL) product, both in its crude form and its digested form.

The inner leaf (IL) product showed only approximately half of the antioxidant capacity as the whole leaf (WL) product; this antioxidant capacity disappeared when digested.

Cellular Antioxidant Protection Assay

The results of the CAP-e assay showed that only the whole leaf (WL) crude product contained antioxidants that were able to cross the lipid bilayer cell membrane, enter the cells, and provide biologically meaningful antioxidant protection under conditions of oxidative stress.

Neither the inner leaf product nor the digested fractions of either product contained antioxidants capable of providing cellular antioxidant protection.

Effect on Free Radical Formation by Inflammatory Cells

As described in the diagram in FIG. 23, immune cells can receive both activating and inhibiting signals from complex natural products, and often a bi-phasic dose response is seen where potent anti-inflammatory compounds are only allowed to show a response at lower doses where immune activating substances (typically active at a different dose range) have been more diluted and are no longer over-riding the anti-inflammatory signals.

Both the whole leaf (WL) and inner leaf (IL) products showed this U-shaped dose response in cell cultures from two out of the three healthy blood donors. The anti-inflammatory effects of IL were stronger than WL; this may either be due to higher levels of anti-inflammatory compounds in IL or higher levels of immune activating compounds in WL.

Notably, the WL IVD showed more potent anti-inflammatory response than WL crude in cell cultures from all three donors.

Example 9

Evaluation of the Effect of Various Aloe Compositions on LPS-stimulated Cytokine Expression in PBMCs The purpose of this experiment was to evaluate an anti-inflammatory and immune modulatory effect of decolorized *aloe vera* leaf juice, *aloe vera* inner leaf juice concentrate, and their fractions that contain a high content of polysaccharides (i.e., acemannan).

The following products were tested:

| Test Product | Abbreviations | Polysaccharide (PS) content and Molecular Weight Peaks in GPC chromatogram |
|---|---|---|
| Aloe whole leaf juice Concentrate, filtered, | Decolorized aloe vera leaf juice | 4.3%, ~150 kDa |
| Aloe inner leaf juice, filtered, | Aloe vera inner leaf juice concentrate | 8.8%, ~150 kDa |
| Dry inner leaf gel | Dry inner leaf gel | 10.5%, ~900 kDa |
| Aloe whole leaf juice, filtered, PS-enriched | Decolorized aloe vera leaf juice PS | 55.9%, 165 kDa |
| Aloe inner leaf juice, filtered, PS-enriched | Aloe vera inner leaf juice concentrate PS | 82%, 695, 216, 37 kDs |

Human peripheral blood mononuclear cells (PBMCs) from a healthy male were used to test the effect of the above aloe materials on the expression of various cytokines stimulated by 50 pg/ml of lipopolysaccharide (LPS). PBMCs are the populations of immune cells that include lymphocytes (T cells, B cells, and NK cells), monocytes, and dendritic cells. In humans, the frequencies of each of these sub-populations vary among individuals.

A cytokine assay was performed as follows. Each aloe material was diluted in culture media and added to PBMC to a final concentration of 1 μg to 100 μg/ml. After incubation for 1 hour at 37° C., some cells were treated with 50 pg/ml of LPS, a pro-inflammatory stimulus, whereas the other cells continued to be cultured in the absence of LPS. After 24 hours of incubation, the supernatants were harvested and analyzed for cytokines(IL-1β, IL-6, MIP-1α, TNF-α, IL-8, and IL-10). The control was either LPS when testing aloe preparations for anti-inflammatory activity or culture medium when testing aloe preparation for direct effect on PBMC. Each value was the average of duplicate readouts per cytokine tested.

Effect of Aloe Composition on Inflammatory LPS Stimulation of Cytokine Secretion in PBMCs The bar graphs in FIGS. 33A(I) to 33C(V) show a significant change in LPS-stimulated expression of cytokines which was caused by the treatment of PBMCs with the aloe test materials, decolorized *aloe vera* leaf juice (Aloe 100×) and polysaccharide (PS)-enriched preparations (Aloe 100× PS and Aloe 200× PS) made from decolorized *aloe vera* leaf juice and *aloe vera* inner leaf juice concentrate, respectively.

Decolorized *aloe vera* leaf juice and its polysaccharide-enriched preparation (Aloe 100× PS) decreased LPS-stimulated expression of both MIP-1α and TNF-α, indicating that the aloe materials had anti-inflammatory effect.

Polysaccharide-enriched preparation (Aloe 200× PS) made from *aloe vera* inner leaf juice concentrate decreased LPS-stimulated expression of MIP-1α and TNF-α, and increased the levels of IL-10, indicating that the aloe material had potent anti-inflammatory effect.

Effect of Aloe Composition on Cytokine Secretion in PBMCs

The bar graphs in FIGS. 34A-34B show a significant change in the steady-state expression of cytokines which was caused by the treatment of PBMCs with the aloe test materials, decolorized *aloe vera* leaf juice (Aloe 100×) and polysaccharide-enriched preparations (Aloe 100× PS and Aloe 200× PS) made from decolorized *aloe vera* leaf juice and *aloe vera* inner leaf juice concentrate, respectively.

In the absence of external pro-inflammatory stimulus, a fraction (Aloe 100× PS) of decolorized *aloe vera* leaf juice that contained a high content of polysaccharide (i.e., acemannan) significantly elevated the steady-state expression of both pro-inflammatory (IL-1β, TNF-α, IL-6, MIP-1α) and anti-inflammatory (IL-10) cytokines, indicating that the aloe material had an immune modulatory effect.

In the absence of external pro-inflammatory stimulus, a fraction (Aloe 200× PS) of *aloe vera* inner leaf juice concentrate that contained a high content of polysaccharide (i.e., acemannan) significantly elevated the steady-state expression of both pro-inflammatory (IL-1β, TNF-α, IL-6, MIP-1α) and anti-inflammatory (IL-10) cytokines, indicating that the aloe material had an immune modulatory effect.

Administration of decolorized *aloe vera* leaf juice directly activated NK and NKT cells, indicating that the aloe material had an immune modulatory effect even in the absence of any stimulant (for example, LPS) not only on innate immune responses to pathologic microorganisms such as bacteria and viruses and to abnormal cells such as cancer cells arising in the body, but also on the adaptive immune responses to autoimmune diseases such as diabetes, atherosclerosis, and cancer.

Effect of Decolorized *Aloe vera* Leaf Juice on Immune Homeostasis

Administration of decolorized *aloe vera* leaf juice led to the differentiation of anti-inflammatory tolerogenic DCs in the presence of LPS such that their interaction with CD4 T cells led to a significantly elevated production of anti-inflammatory Th2 cytokines such as IL-10 and IL-5 and to a significantly reduced production of inflammatory IFN-γ, a Th1 cytokine. These results indicate that human consumption of *aloe vera* leaf juice concentrate could enhance an immune homeostasis through peripheral tolerance in the gastrointestinal gut mucosa.

Administration of decolorized *aloe vera* leaf juice significantly negated the suppressive effect of LPS on the arginase activity of LPS-activated macrophages, indicating the aloe composition could promote the switching or polarization of inflammatory M1 macrophage into anti-inflammatory M2 macrophages.

Example 10

Evaluation of Biologically-relevant Antioxidant and Immune-modulatory Effects of Decolorized *Aloe vera* Leaf and Inner Leaf Preparations Using a Variety of In Vitro Techniques Antioxidant activity of decolorized leaf (L) and inner-leaf (IL) *aloe vera* preparations were assessed for total antioxidant capacity by the Folin-Ciocalteu method and for cellular antioxidant protection using human erythrocytes. Direct immune-modulatory effects were assessed by treating human peripheral blood mononuclear cells (PBMCs) from three healthy donors with each *aloe vera* preparation for 24 hours, followed by multi-parameter flow-cytometry, which evaluated the activation status (i.e., expression of CD25 and CD69) of various immune cell populations [natural killer (NK) cells (CD3−/CD56+), NKT cells (CD3+/CD56+), and T lymphocytes (CD3+/CD56−)] that were gated by double-staining with monoclonal antibodies specific for CD3 and CD56. A cytokine panel was used to measure the levels of pro- and anti-inflammatory cytokines in the supernatants of the PBMC culture. In order to investigate any anti-inflammatory effects of each *aloe vera* preparation, similar assay methods were used except that PBMCs were pre-treated with the *aloe vera* preparation and then stimulated by either lipopolysaccharide (LPS) or polyinosinic:polycytidylic (poly I:C) acid to mimic bacterial and viral insult, respectively.

L showed higher total antioxidant capacity than IL. L showed antioxidant protection in the cell-based assay. L showed significant unstimulated and LPS and poly I:C stimulated immune-modulatory activity, including increases in immune-cell activation and levels of cytokines compared to IL. The decolorized *aloe vera* leaf preparation showed higher antioxidant and immune-modulatory activity than the inner-leaf preparation.

The foregoing description details certain embodiments of the compositions and methods disclosed herein. It will be appreciated, however, that no matter how detailed the foregoing appears in text, the compositions and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments. The above description discloses several compositions, methods and materials of the present invention. This invention is susceptible to modifications in the compositions, methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. Applicant reserves the right to submit claims directed to combinations and sub-combinations of the disclosed inventions that are believed to be novel and non-obvious. Inventions embodied in other combinations and sub-combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

What is claimed is:

1. A method for inducing a beneficial effect on a human microbiome, the method comprising:
   administering a composition to the gastrointestinal system of a human, the composition comprising decolorized *aloe vera* juice and one or more excipients,
   wherein the *aloe vera* comprises an effective amount to result in a concentration from about 0.507 g/L to about 1.014 g/L of the composition upon administration to the gastrointestinal system of the human, and wherein the beneficial effect is selected from the group consisting of an increased production of short chain fatty acids in the proximal colon, an increased total microbial population in the proximal colon, an increased production of acetic acid in the proximal colon, an increased production of propionic acid in the proximal colon, an increased population of the total bacteria in the proximal colon, an increased population of the transient concentration of bifidobacteria in the proximal colon, antioxidant protection within cells exposed to free radicals, activation of natural killer cells, activation of natural killer T cells, an increase in the production of Th2-type cytokines, a decrease in IFN-γ, promotion of M1 macrophages into M2 macrophages, and repair of injury to a monolayer of Caco-2 cells.

2. The method of claim 1, wherein the beneficial effect on the human microbiome is an increased production of short chain fatty acids in the proximal colon.

3. The method of claim 1, wherein the beneficial effect on the human microbiome is repair of injury to a monolayer of Caco-2 cells.

4. The method of claim 1, wherein the beneficial effect on the human microbiome is antioxidant protection within cells exposed to free radicals.

5. The method of claim 1, wherein the beneficial effect on the human microbiome is selected from the group consisting of activation of natural killer cells, activation of natural killer T cells, and an increase in the production of Th2-type cytokines.

6. The method of claim 5, wherein the Th2-type cytokines are IL-10 or IL-5.

7. The method of claim 1, wherein the beneficial effect on the human microbiome is a decrease in IFN-γ or promotion of M1 macrophages into M2 macrophages.

8. The method of claim 1, wherein the beneficial effect on the human microbiome is an increased total microbial population in the proximal colon.

9. The method of claim 1, wherein the beneficial effect on the human microbiome is an increased production of acetic acid in the proximal colon.

10. The method of claim 1, wherein the beneficial effect on the human microbiome is an increased production of propionic acid in the proximal colon.

11. The method of claim 1, wherein the beneficial effect on the human microbiome is an increased production of total bacteria in the proximal colon.

12. The method of claim 1, wherein the beneficial effect on the human microbiome is an increased production of the transient concentration of bifidobacteria in the proximal colon.

13. The method of claim 3, wherein the injury to a monolayer of Caco-2 cells is injury caused by THP1 cells.

14. The method of claim 1, wherein the composition further comprises an acidity modifier selected from the group consisting of citric acid salt, malic acid salt, acetic acid, acetic acid salt, lactic acid, lactic acid salt, tartaric acid, tartaric acid salt, formic acid, formic acid salt, propionic acid, propionic acid salt, butyric acid, butyric acid salt, valeric acid, valeric acid salt, phosphoric acid, and phosphoric acid salt.

15. The method of claim 1, wherein the one or more excipients are selected from the group consisting of sorbic acid, sorbic acid salt, benzoic acid, benzoic acid salt, lactic acid, lactic acid salt, citric acid salt, malic acid salt, acetic acid, acetic acid salt, tartaric acid, tartaric acid salt, rosemary extract, lovage extract, chitosan, sage essential oil, thymol oil nisin, e-polylysine, grape seed extract, and goji berry extract.

16. The method of claim 1, wherein the one or more excipients are selected from the group consisting of honey, fructose, dextrose, and maltodextrin.

17. The method of claim 1, wherein the one or more excipients are selected from the group consisting of cellulose powder, modified starch, microcrystalline cellulose, magnesium stearate, stearic acid, sodium croscarmellose, calcium carbonate, and dicalcium phosphate.

18. The method of claim 1, wherein the *aloe vera* juice comprises not more than about 10 ppm aloin.

19. The method of claim 1, wherein the *aloe vera* juice comprises at least about 5% acetylated acemannan.

* * * * *